United States Patent [19]

Yasumura et al.

[11] Patent Number: 5,160,735
[45] Date of Patent: Nov. 3, 1992

[54] PLASMINOGEN ACTIVATOR

[75] Inventors: Shigeyoshi Yasumura, Tokyo, Japan; Tatsunari Nishi, Los Angeles, Calif.; Seiga Ito, Kanagawa, Japan

[73] Assignee: Kyowa Hakko Kogyo Co. Ltd., Tokyo, Japan

[21] Appl. No.: 538,270

[22] Filed: Jun. 14, 1990

[30] Foreign Application Priority Data

Jun. 19, 1989 [JP] Japan ................. 1-156302

[51] Int. Cl.⁵ .................... A61K 37/54; C12N 9/72
[52] U.S. Cl. ...................... 424/94.63; 435/215
[58] Field of Search ......... 435/212, 215, 69.1, 435/172.3, 320.1; 935/27; 924/94.63; 536/27

[56] References Cited

FOREIGN PATENT DOCUMENTS 0200451 11/1986 European Pat. Off. .
0210279  2/1987 European Pat. Off. .
 312942  4/1989 European Pat. Off. .
 370205  5/1990 European Pat. Off. .

OTHER PUBLICATIONS

Schechter et al., Biochem. & Biophys. Res. Comm., vol. 27 No. 2 pp. 157–162 (1967).
Poszgay et al., Eur. J. Biochem., vol. 115, pp. 491–495 (1981).
Chang, Eur. J. Biochem., vol. 151, pp. 217–224 (1985).

Primary Examiner—Richard A. Schwartz
Assistant Examiner—Nancy T. Vogel
Attorney, Agent, or Firm—Nixon & Vanderhye

[57] ABSTRACT

A novel plasminogen activator which is identical in peptide sequence to naturally occurring human prourokinase except that the 155th amino acid counting from the N-terminal amino acid (serine) is other than the 155th amino acid (proline) of naturally occurring human prourokinase, optionally with the addition of methionine at the N terminus.

6 Claims, 47 Drawing Sheets

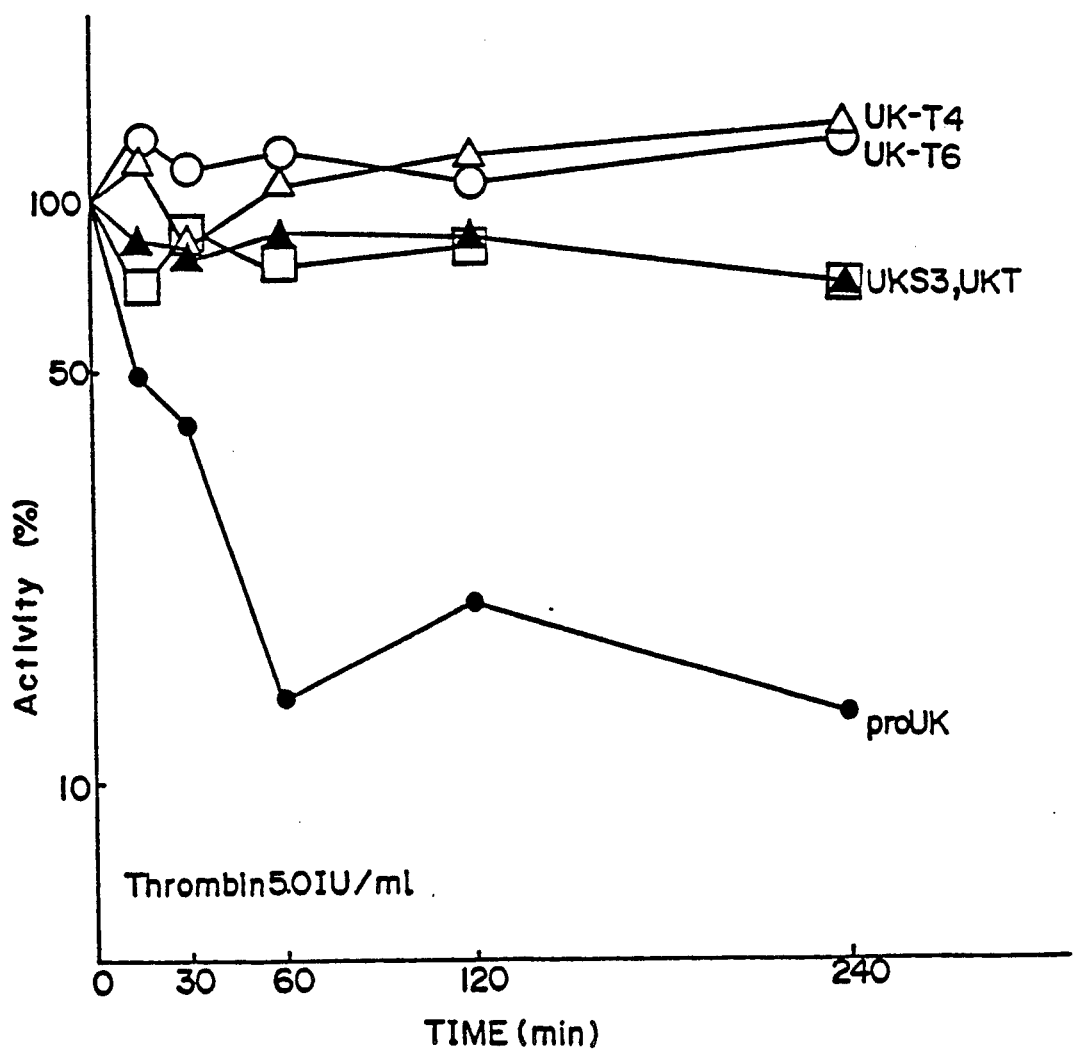
FIG. 7-(1)

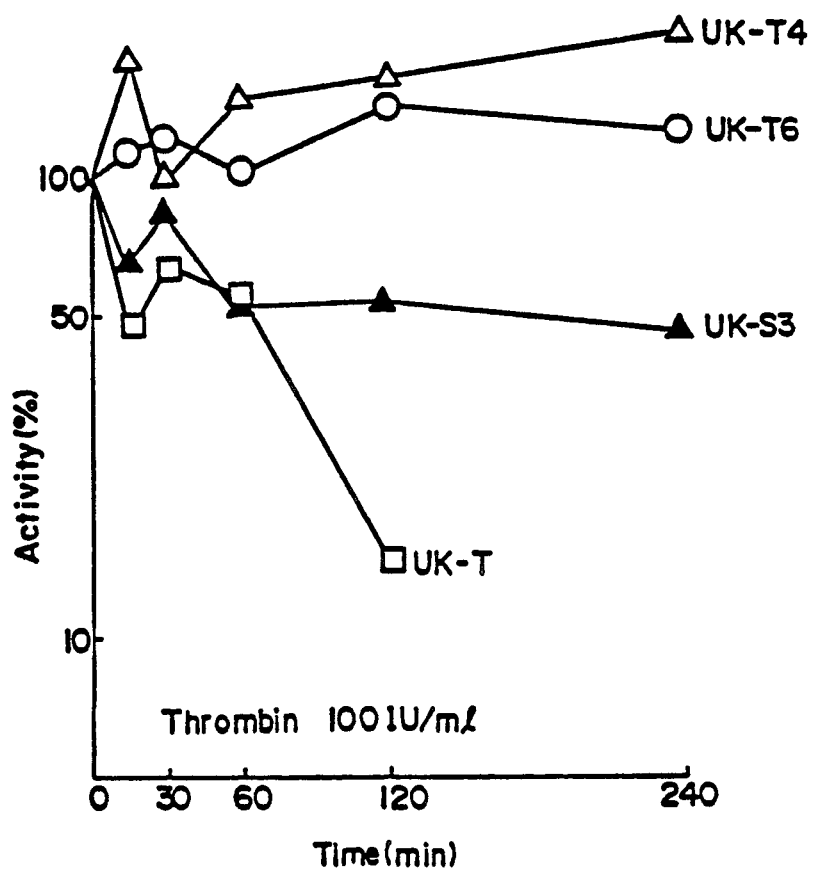
FIG. 7-(2)

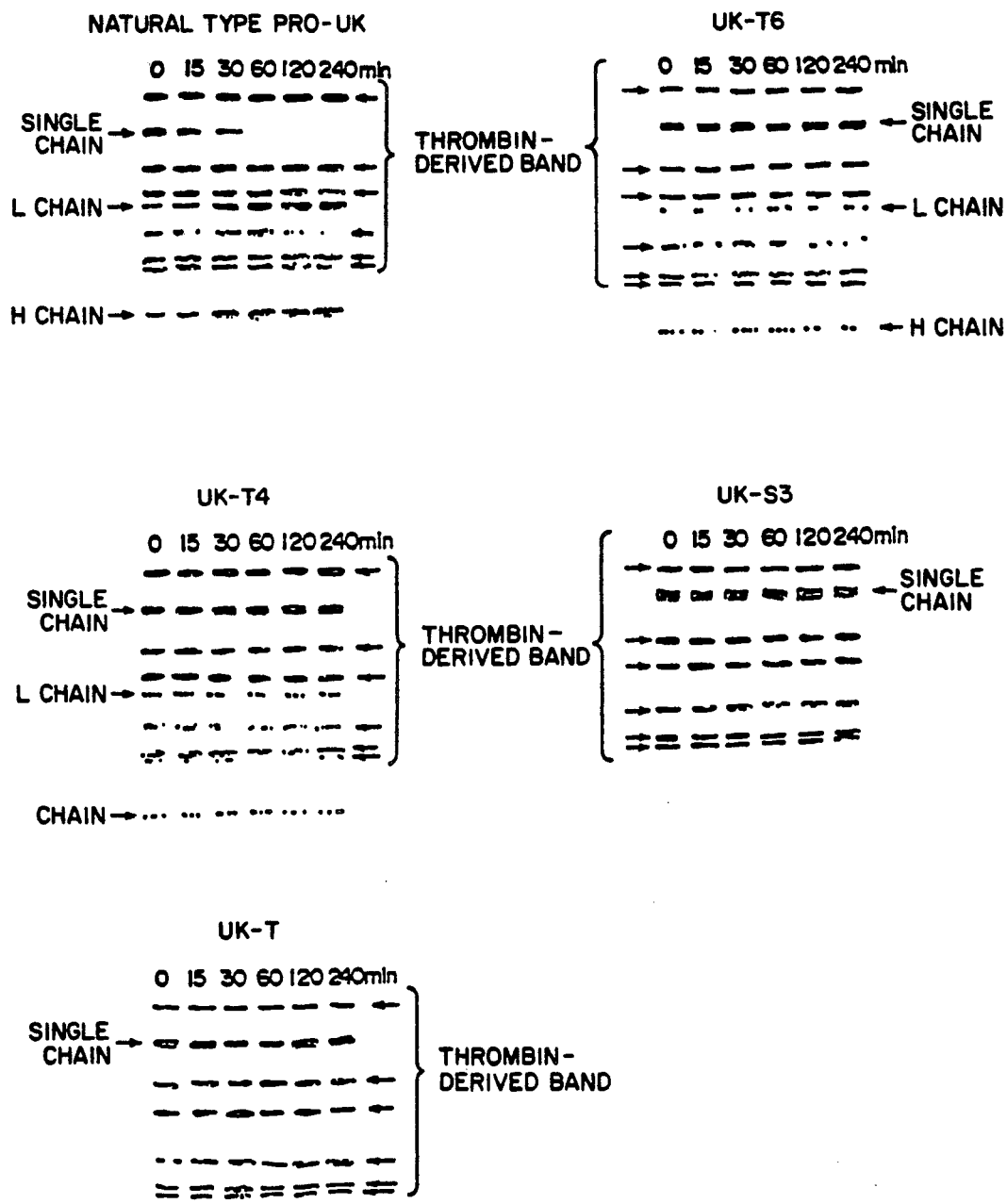
FIG. 7-(3)

FIG. 8-(1)
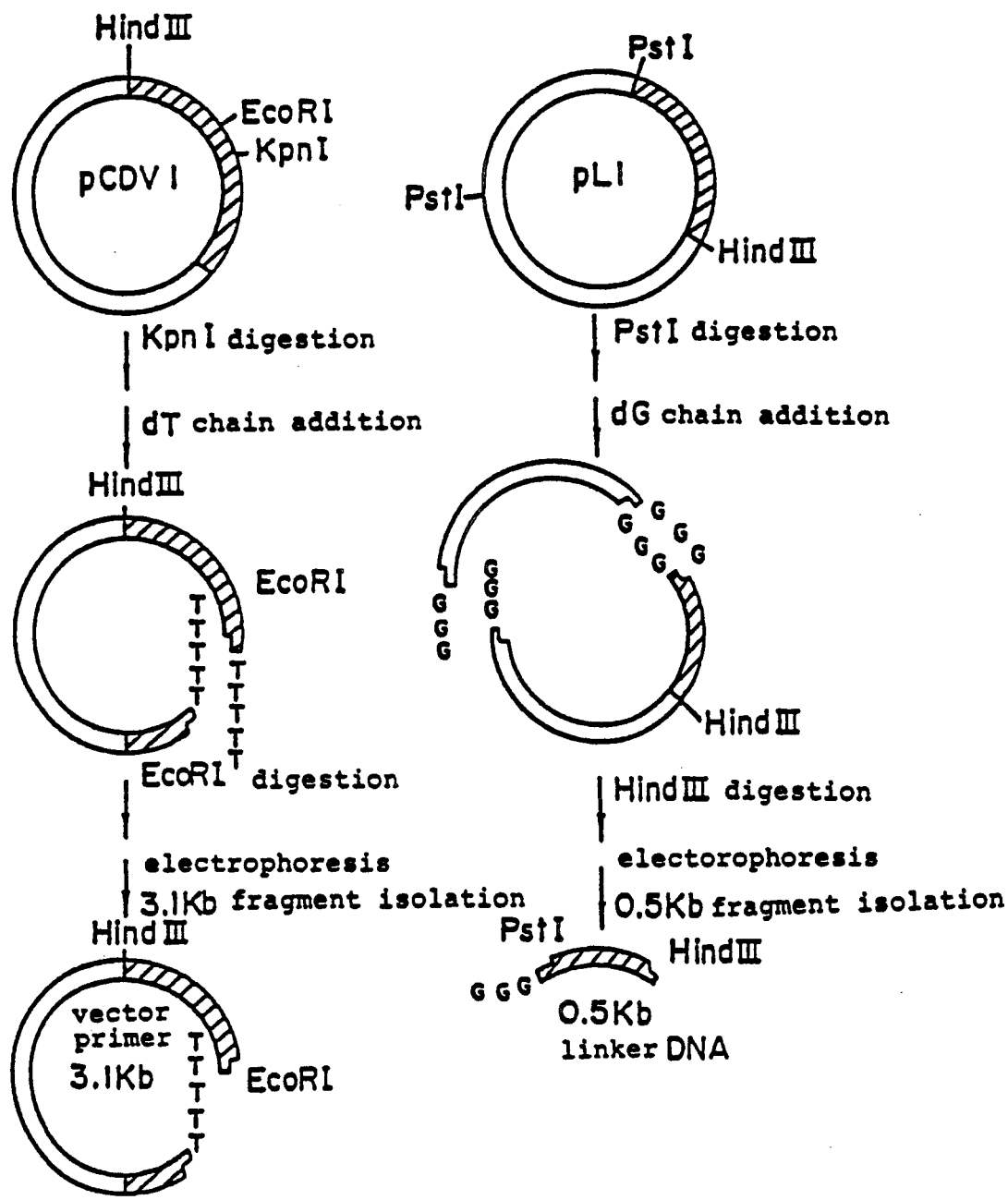

FIG. 8-(2)
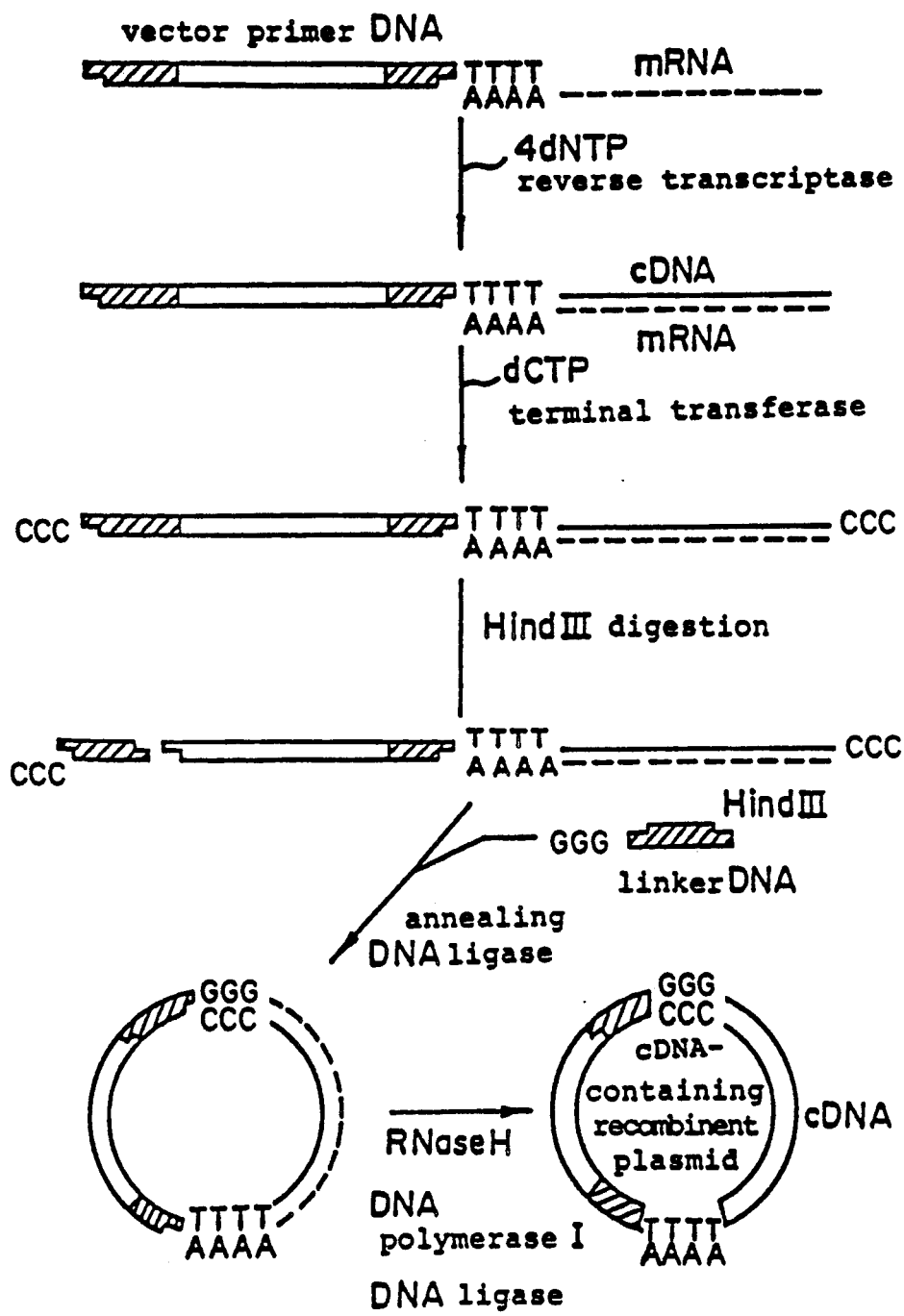

FIG. 21
p ACTGTGACGTCCCCAGCTGTTCTGAAGGAAATGCA
TGACACTGCAGGGGTCGACAAGACTTCCTTT p
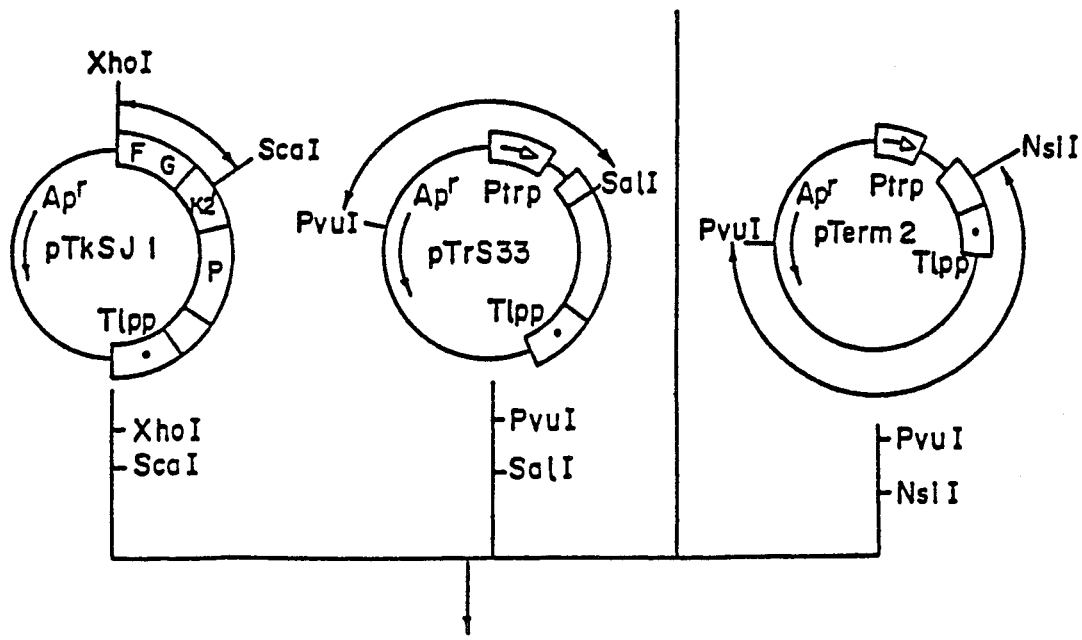
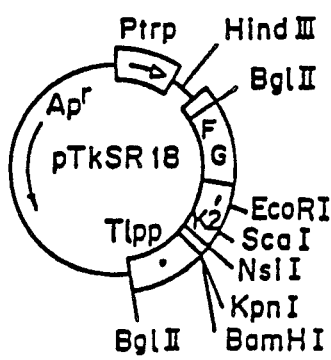

FIG. 22
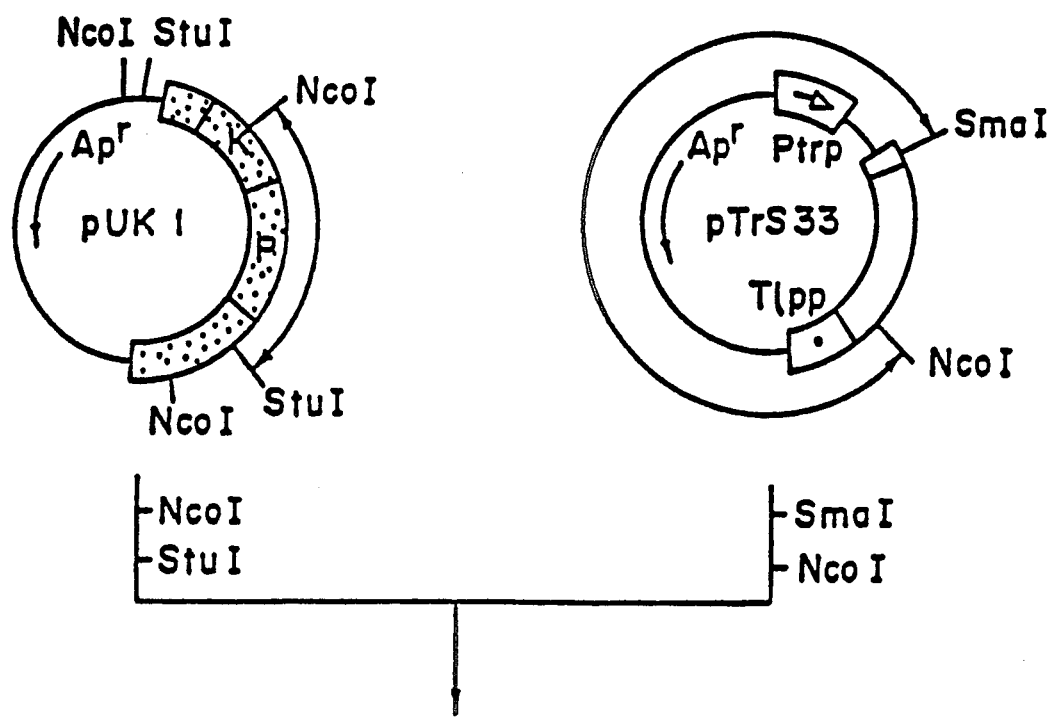
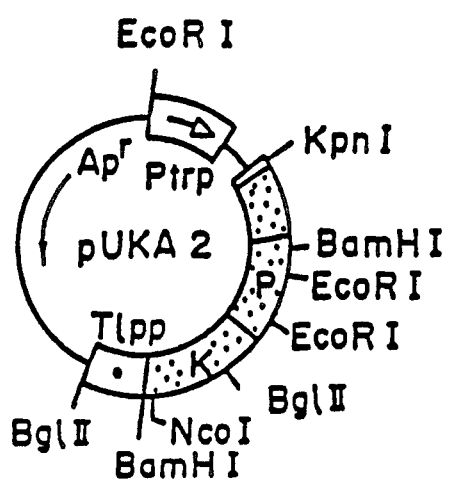

FIG. 31
p AGCTTGAGATCCTACAGGAGTCCAGGGCTGGAGAGAAAACCTCTGCG
    ACTCTAGGATGTCCTCAGGTCCCGACCTCTCTTTTGGAGACGCTCCTTTp
pAGGAAAGGGAAGGAGCAAGCCGTGAATTTAAGGGACGCTGTGAAGCAAT
   CCCTTCCTCGTTCGGCACTTAAATTCCCTGCGACACTTCGTTAGTACp
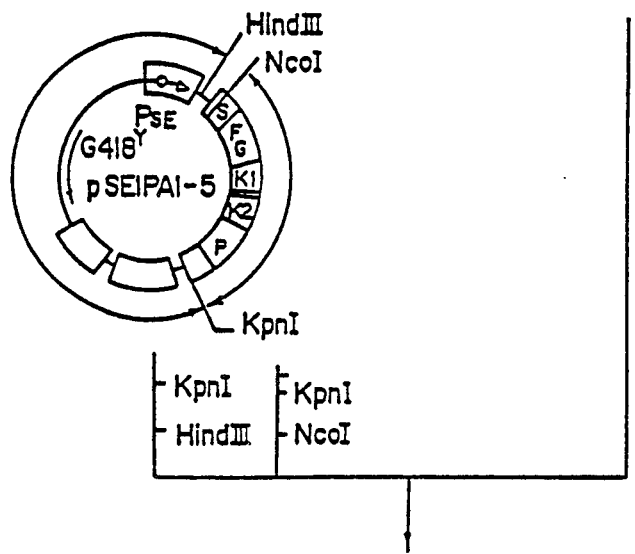
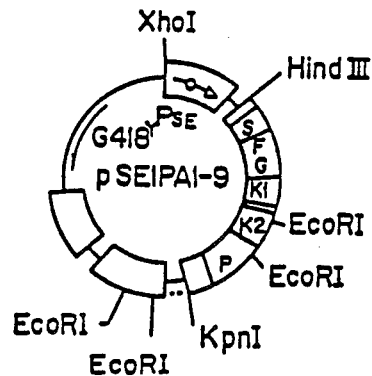

FIG. 32
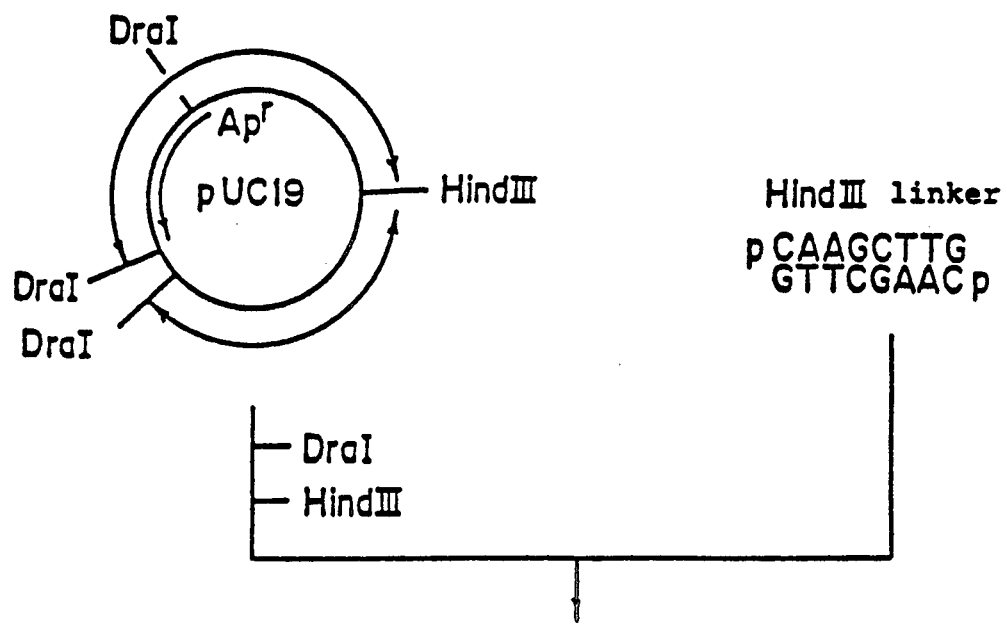
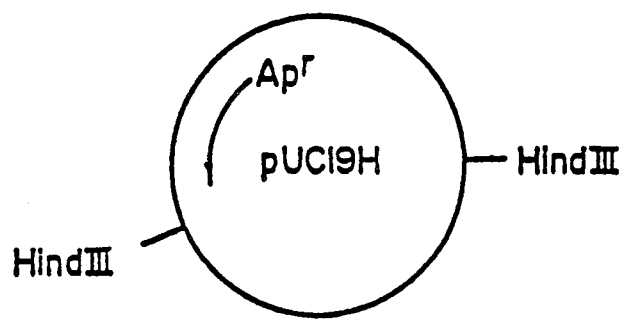

FIG. 40

```
           10        20        30        40        50        60        70
AGCAATGAACTTCATCAAGTTCCATCGAACTGTGACTGTCTAAATGGAGGAACATGTGTGTCCAACAAGTACTTC
SerAsnGluLeuHisGlnValProSerAsnCysAspCysLeuAsnGlyGlyThrCysValSerAsnLysTyrPhe 85        95       105       115       125       135       145
TCCAACATTCACTGGTGCAACTGCCCAAAGAAATTCGGAGGGCAGCACTGTGAAATAGATAAGTCAAAAACCTGC
SerAsnIleHisTrpCysAsnCysProLysLysPheGlyGlyGlnHisCysGluIleAspLysSerLysThrCys 160       170       180       190       200       210       220
TATGAGGGGAATGGTCACTTTTACCGAGGAAAGGCCAGCACTGACACCATGGGCCGGCCCTGCCTGCCCTGGAAC
TyrGluGlyAsnGlyHisPheTyrArgGlyLysAlaSerThrAspThrMetGlyArgProCysLeuProTrpAsn 235       245       255       265       275       285       295
TCTGCCACTGTCCTTCAGCAAACGTACCATGCCCACAGATCTGATGCTCTTCAGCTGGGCCTGGGGAAACATAAT
SerAlaThrValLeuGlnGlnThrTyrHisAlaHisArgSerAspAlaLeuGlnLeuGlyLeuGlyLysHisAsn 310       320       330       340       350       360       370
TACTGCAGGAACCCAGACAACCGGAGGCGACCCTGGTGCTATGTGCAGGTGGGCCTAAAGCCGCTTGTCCAAGAG
TyrCysArgAsnProAspAsnArgArgArgProTrpCysTyrValGlnValGlyLeuLysProLeuValGlnGlu 385       395       405       415       425       435       445
TGCATGGTGCATGACTGCGCAGATGGAAAAAAGCCCTCCTCTCCTCCAGAAGAATTAAAATTTCAGTGTGGCCAA
CysMetValHisAspCysAlaAspGlyLysLysProSerSerProProGluGluLeuLysPheGlnCysGlyGln 460       470       480       490       500       510       520
AAGACCTTAAGGACGCGTTTTAAGATTATTGGAGGAGAATTCACCACCATCGAGAACCAGCCCTGGTTTGCGGCC
LysThrLeuArgThrArgPheLysIleIleGlyGlyGluPheThrThrIleGluAsnGlnProTrpPheAlaAla 535       545       555       565       575       585       595
ATCTACAGGAGGCACCGGGGGGGCTCTGTCACCTACGTGTGTGGAGGCAGCCTCATCAGCCCTTGCTGGGTGATC
IleTyrArgArgHisArgGlyGlySerValThrTyrValCysGlyGlySerLeuIleSerProCysTrpValIle 610       620       630       640       650       660       670
AGCGCCACACACTGCTTCATTGATTACCCAAAGAAGGAGGACTACATCGTCTACCTGGGTCGCTCAAGGCTTAAC
SerAlaThrHisCysPheIleAspTyrProLysLysGluAspTyrIleValTyrLeuGlyArgSerArgLeuAsn 685       695       705       715       725       735       745
TCCAACACGCAAGGGGAGATGAAGTTTGAGGTGGAAAACCTCATCCTACACAAGGACTACAGCGCTGACACGCTT
SerAsnThrGlnGlyGluMetLysPheGluValGluAsnLeuIleLeuHisLysAspTyrSerAlaAspThrLeu 760       770       780       790       800       810       820
GCTCACCACAATGACATTGCCTTGCTGAAGATCCGTTCCAAGGAGGGCAGGTGTGCGCAGCCATCCCGGACTATA
AlaHisHisAsnAspIleAlaLeuLeuLysIleArgSerLysGluGlyArgCysAlaGlnProSerArgThrIle 835       845       855       865       875       885       895
CAGACCATCTGCCTGCCCTCGATGTATAACGATCCCCAGTTTGGCACAAGCTGTGAGATCACTGGCTTTGGAAAA
GlnThrIleCysLeuProSerMetTyrAsnAspProGlnPheGlyThrSerCysGluIleThrGlyPheGlyLys 910       920       930       940       950       960       970
GAGAATTCTACCGACTATCTCTATCCGGAGCAGCTGAAAATGACTGTTGTGAAGCTGATTTCCCACCGGGAGTGT
GluAsnSerThrAspTyrLeuTyrProGluGlnLeuLysMetThrValValLysLeuIleSerHisArgGluCys 985       995      1005      1015      1025      1035      1045
CAGCAGCCCCACTACTACGGCTCTGAAGTCACCACCAAAATGCTGTGTGCTGCTGACCCACAGTGGAAAACAGAT
GlnGlnProHisTyrTyrGlySerGluValThrThrLysMetLeuCysAlaAlaAspProGlnTrpLysThrAsp 1060      1070      1080      1090      1100      1110      1120
TCCTGCCAGGGAGACTCAGGGGGACCCCTCGTCTGTTCCCTCCAAGGCCGCATGACTTTGACTGGAATTGTGAGC
SerCysGlnGlyAspSerGlyGlyProLeuValCysSerLeuGlnGlyArgMetThrLeuThrGlyIleValSer 1135      1145      1155      1165      1175      1185      1195
TGGGGCCGTGGATGTGCCCTGAAGGACAAGCCAGGCGTCTACACGAGAGTCTCACACTTCTTACCCTGGATCCGC
TrpGlyArgGlyCysAlaLeuLysAspLysProGlyValTyrThrArgValSerHisPheLeuProTrpIleArg 1210      1220      1230
AGTCACACCAAGGAAGAGAATGGCCTGGCCCTCTGA
SerHisThrLysGluGluAsnGlyLeuAlaLeu***
```

FIG. 41

```
          10        20        30        40        50        60        70
AGCAATGAACTTCATCAAGTTCCATCGAACTGTGACTGTCTAAATGGAGGAACATGTGTGTCCAACAAGTACTTC
SerAsnGluLeuHisGlnValProSerAsnCysAspCysLeuAsnGlyGlyThrCysValSerAsnLysTyrPhe 85        95       105       115       125       135       145
TCCAACATTCACTGGTGCAACTGCCCAAAGAAATTCGGAGGGCAGCACTGTGAAATAGATAAGTCAAAAACCTGC
SerAsnIleHisTrpCysAsnCysProLysLysPheGlyGlyGlnHisCysGluIleAspLysSerLysThrCys 160       170       180       190       200       210       220
TATGAGGGGAATGGTCACTTTTACCGAGGAAAGGCCAGCACTGACACCATGGGCCGGCCCTGCCTGCCCTGGAAC
TyrGluGlyAsnGlyHisPheTyrArgGlyLysAlaSerThrAspThrMetGlyArgProCysLeuProTrpAsn 235       245       255       265       275       285       295
TCTGCCACTGTCCTTCAGCAAACGTACCATGCCCACAGATCTGATGCTCTTCAGCTGGGCCTGGGGAAACATAAT
SerAlaThrValLeuGlnGlnThrTyrHisAlaHisArgSerAspAlaLeuGlnLeuGlyLeuGlyLysHisAsn 310       320       330       340       350       360       370
TACTGCAGGAACCCAGACAACCGGAGGCGACCCTGGTGCTATGTGCAGGTGGGCCTAAAGCCGCTTGTCCAAGAG
TyrCysArgAsnProAspAsnArgArgArgProTrpCysTyrValGlnValGlyLeuLysProLeuValGlnGlu 385       395       405       415       425       435       445
TGCATGGTGCATGACTGCGCAGATGGAAAAAAGCCCTCCTCTCCTCCAGAAGAATTAAAATTTCAGTGTGGCCAA
CysMetValHisAspCysAlaAspGlyLysLysProSerSerProProGluGluLeuLysPheGlnCysGlyGln 460       470       480       490       500       510       520
AAGACTAGTCGAACGCGTTTTAAGATTATTGGGGGAGAATTCACCACCATCGAGAACCAGCCCTGGTTTGCGGCC
LysThrSerArgThrArgPheLysIleIleGlyGlyGluPheThrThrIleGluAsnGlnProTrpPheAlaAla 535       545       555       565       575       585       595
ATCTACAGGAGGCACCGGGGGGGCTCTGTCACCTACGTGTGTGGAGGCAGCCTCATCAGCCCTTGCTGGGTGATC
IleTyrArgArgHisArgGlyGlySerValThrTyrValCysGlyGlySerLeuIleSerProCysTrpValIle 610       620       630       640       650       660       670
AGCGCCACACACTGCTTCATTGATTACCCAAAGAAGGAGGACTACATCGTCTACCTGGGTCGCTCAAGGCTTAAC
SerAlaThrHisCysPheIleAspTyrProLysLysGluAspTyrIleValTyrLeuGlyArgSerArgLeuAsn 685       695       705       715       725       735       745
TCCAACACGCAAGGGGAGATGAAGTTTGAGGTGGAAAAACCTCATCCTACACAAGGACTACAGCGCTGACACGCTT
SerAsnThrGlnGlyGluMetLysPheGluValGluAsnLeuIleLeuHisLysAspTyrSerAlaAspThrLeu 760       770       780       790       800       810       820
GCTCACCACAATGACATTGCCTTGCTGAAGATCCGTTCCAAGGAGGGCAGGTGTGCGCAGCCATCCCGGACTATA
AlaHisHisAsnAspIleAlaLeuLeuLysIleArgSerLysGluGlyArgCysAlaGlnProSerArgThrIle 835       845       855       865       875       885       895
CAGACCATCTGCCTGCCCTCGATGTATAACGATCCCCAGTTTGGCACAAGCTGTGAGATCACTGGCTTTGGAAAA
GlnThrIleCysLeuProSerMetTyrAsnAspProGlnPheGlyThrSerCysGluIleThrGlyPheGlyLys 910       920       930       940       950       960       970
GAGAATTCTACCGACTATCTCTATCCGGAGCAGCTGAAAATGACTGTTGTGAAGCTGATTTCCCACCGGGAGTGT
GluAsnSerThrAspTyrLeuTyrProGluGlnLeuLysMetThrValValLysLeuIleSerHisArgGluCys 985       995      1005      1015      1025      1035      1045
CAGCAGCCCCACTACTACGGCTCTGAAGTCACCACCAAAATGCTGTGTGCTGCTGACCCACAGTGGAAAACAGAT
GlnGlnProHisTyrTyrGlySerGluValThrThrLysMetLeuCysAlaAlaAspProGlnTrpLysThrAsp 1060      1070      1080      1090      1100      1110      1120
TCCTGCCAGGGAGACTCAGGGGGACCCCTCGTCTGTTCCCTCCAAGGCCGGATGACTTTGACTGGAATTGTGAGC
SerCysGlnGlyAspSerGlyGlyProLeuValCysSerLeuGlnGlyArgMetThrLeuThrGlyIleValSer 1135      1145      1155      1165      1175      1185      1195
TGGGGCCGTGGATGTGCCCTGAAGGACAAGCCAGGCGTCTACACGAGAGTCTCACACTTCTTACCCTGGATCCGC
TrpGlyArgGlyCysAlaLeuLysAspLysProGlyValTyrThrArgValSerHisPheLeuProTrpIleArg 1210      1220      1230
AGTCACACCAAGGAAGAGAATGGCCTGGCCCTCTGA
SerHisThrLysGluGluAsnGlyLeuAlaLeu***
```

FIG. 42

```
          10        20        30        40        50        60        70
AGCAATGAACTTCATCAAGTTCCATCGAACTGTGACTGTCTAAATGGAGGAACATGTGTGTCCAACAAGTACTTC
SerAsnGluLeuHisGlnValProSerAsnCysAspCysLeuAsnGlyGlyThrCysValSerAsnLysTyrPhe 85        95       105       115       125       135       145
TCCAACATTCACTGGTGCAACTGCCCAAAGAAATTCGGAGGGCAGCACTGTGAAATAGATAAGTCAAAAACCTGC
SerAsnIleHisTrpCysAsnCysProLysLysPheGlyGlyGlnHisCysGluIleAspLysSerLysThrCys 160       170       180       190       200       210       220
TATGAGGGGAATGGTCACTTTTACCGAGGAAAGGCCAGCACTGACACCATGGGCCGGCCCTGCCTGCCCTGGAAC
TyrGluGlyAsnGlyHisPheTyrArgGlyLysAlaSerThrAspThrMetGlyArgProCysLeuProTrpAsn 235       245       255       265       275       285       295
TCTGCCACTGTCCTTCAGCAAACGTACCATGCCCACAGATCTGATGCTCTTCAGCTGGGCCTGGGGAAACATAAT
SerAlaThrValLeuGlnGlnThrTyrHisAlaHisArgSerAspAlaLeuGlnLeuGlyLeuGlyLysHisAsn 310       320       330       340       350       360       370
TACTGCAGGAACCCAGACAACCGGAGGCGACCCTGGTGCTATGTGCAGGTGGGCCTAAAGCCGCTTGTCCAAGAG
TyrCysArgAsnProAspAsnArgArgArgProTrpCysTyrValGlnValGlyLeuLysProLeuValGlnGlu 385       395       405       415       425       435       445
TGCATGGTGCATGACTGCGCAGATGGAAAAAAGCCCTCCTCTCCTCCAGAAGAATTAAAATTTCAGTGTGGCCAA
CysMetValHisAspCysAlaAspGlyLysLysProSerSerProProGluGluLeuLysPheGlnCysGlyGln 460       470       480       490       500       510       520
AAGACTAATCGAACGCGTTTTAAGATTATTGGGGGAGAATTCACCACCATCGAGAACCAGCCCTGGTTTGCGGCC
LysThrAsnArgThrArgPheLysIleIleGlyGlyGluPheThrThrIleGluAsnGlnProTrpPheAlaAla 535       545       555       565       575       585       595
ATCTACAGGAGGCACCGGGGGGGCTCTGTCACCTACGTGTGTGGAGGCAGCCTCATCAGCCCTTGCTGGGTGATC
IleTyrArgArgHisArgGlyGlySerValThrTyrValCysGlyGlySerLeuIleSerProCysTrpValIle 610       620       630       640       650       660       670
AGCGCCACACACTGCTTCATTGATTACCCAAAGAAGGAGGACTACATCGTCTACCTGGGTCGCTCAAGGCTTAAC
SerAlaThrHisCysPheIleAspTyrProLysLysGluAspTyrIleValTyrLeuGlyArgSerArgLeuAsn 685       695       705       715       725       735       745
TCCAACACGCAAGGGGAGATGAAGTTTGAGGTGGAAAAACCTCATCCTACACAAGGACTACAGCGCTGACACGCTT
SerAsnThrGlnGlyGluMetLysPheGluValGluAsnLeuIleLeuHisLysAspTyrSerAlaAspThrLeu 760       770       780       790       800       810       820
GCTCACCACAATGACATTGCCTTGCTGAAGATCCGTTCCAAGGAGGGCAGGTGTGCGCAGCCATCCCGGACTATA
AlaHisHisAsnAspIleAlaLeuLeuLysIleArgSerLysGluGlyArgCysAlaGlnProSerArgThrIle 835       845       855       865       875       885       895
CAGACCATCTGCCTGCCCTCGATGTATAACGATCCCCAGTTTGGCACAAGCTGTGAGATCACTGGCTTTGGAAAA
GlnThrIleCysLeuProSerMetTyrAsnAspProGlnPheGlyThrSerCysGluIleThrGlyPheGlyLys 910       920       930       940       950       960       970
GAGAATTCTACCGACTATCTCTATCCGGAGCAGCTGAAAATGACTGTTGTGAAGCTGATTTCCCACCGGGAGTGT
GluAsnSerThrAspTyrLeuTyrProGluGlnLeuLysMetThrValValLysLeuIleSerHisArgGluCys 985       995      1005      1015      1025      1035      1045
CAGCAGCCCCACTACTACGGCTCTGAAGTCACCACCAAAATGCTGTGTGCTGCTGACCCACAGTGGAAAACAGAT
GlnGlnProHisTyrTyrGlySerGluValThrThrLysMetLeuCysAlaAlaAspProGlnTrpLysThrAsp 1060      1070      1080      1090      1100      1110      1120
TCCTGCCAGGGAGACTCAGGGGGACCCCTCGTCTGTTCCCTCCAAGGCCGCATGACTTTGACTGGAATTGTGAGC
SerCysGlnGlyAspSerGlyGlyProLeuValCysSerLeuGlnGlyArgMetThrLeuThrGlyIleValSer 1135      1145      1155      1165      1175      1185      1195
TGGGGCCGTGGATGTGCCCTGAAGGACAAGCCAGGCGTCTACACGAGAGTCTCACACTTCTTACCCTGGATCCGC
TrpGlyArgGlyCysAlaLeuLysAspLysProGlyValTyrThrArgValSerHisPheLeuProTrpIleArg 1210      1220      1230
AGTCACACCAAGGAAGAGAATGGCCTGGCCCTCTGA
SerHisThrLysGluGluAsnGlyLeuAlaLeu***
```

FIG. 43-(I)

```
        10        20        30        40        50        60        70
ATGAGAGCCCTGCTGGCGCGCCTGCTTCTCTGCGTCCTGGTCGTGAGCGACTCCAAAGGCAGCAATGAACTTCAT
MetArgAlaLeuLeuAlaArgLeuLeuLeuCysValLeuValValSerAspSerLysGlySerAsnGluLeuHis
└→ signal peptide                                    ←─┴─→ growth factor
        85        95       105       115       125       135       145 domain
CAAGTTCCATCGAACTGTGACTGTCTAAATGGAGGAACATGTGTGTCCAACAAGTACTTCTCCAACATTCACTGG
GlnValProSerAsnCysAspCysLeuAsnGlyGlyThrCysValSerAsnLysTyrPheSerAsnIleHisTrp 160       170       180       190       200       210       220
TGCAACTGCCCCAAAGAAATTCGGAGGGCAGCACTGTGAAATAGATAAGTCAAAAACCTGCTATGAGGGGAATGGT
CysAsnCysProLysLysPheGlyGlyGlnHisCysGluIleAspLysSerLysThrCysTyrGluGlyAsnGly
                                                                 ←─┴─→ Kringle domain
       235       245       255       265      275.       285       295
CACTTTTACCGAGGAAAGGCCAGCACTGACACCATGGGCCGGCCCTGCCTGCCCTGGAACTCTGCCACTGTCCTT
HisPheTyrArgGlyLysAlaSerThrAspThrMetGlyArgProCysLeuProTrpAsnSerAlaThrValLeu 310       320       330       340       350       360       370
CAGCAAACGTACCATGCCCACAGATCTGATGCTCTTCAGCTGGGCCTGGGGAAACATAATTACTGCAGGAACCCA
GlnGlnThrTyrHisAlaHisArgSerAspAlaLeuGlnLeuGlyLeuGlyLysHisAsnTyrCysArgAsnPro 385       395       405       415       425       435       445
GACAACCGGAGGCGACCCTGGTGCTATGTGCAGGTGGGCCTAAAGCCGCTTGTCCAAGAGTGCATGGTGCATGAC
AspAsnArgArgArgProTrpCysTyrValGlnValGlyLeuLysProLeuValGlnGluCysMetValHisAsp 460       470       480       490       500       510       520
TGCGCAGATGGAAAAAAGCCCTCCTCTCCTCCAGAAGAATTAAAATTTCAGTGTGGCCAAAAGACTCTGAGGCCC
CysAlaAspGlyLysLysProSerSerProProGluGluLeuLysPheGlnCysGlyGlnLysThrLeuArgPro
            ←─┴─→ protease domain
       535       545       555       565       575       585       595
CGCTTTAAGATTATTGGGGGAGAATTCACCACCATCGAGAACCAGCCCTGGTTTGCGGCCATCTACAGGAGGCAC
ArgPheLysIleIleGlyGlyGluPheThrThrIleGluAsnGlnProTrpPheAlaAlaIleTyrArgArgHis 610       620       630       640       650       660       670
CGGGGGGGCTCTGTCACCTACGTGTGTGGAGGCAGCCTCATCAGCCCTTGCTGGGTGATCAGCGCCACACACTGC
ArgGlyGlySerValThrTyrValCysGlyGlySerLeuIleSerProCysTrpValIleSerAlaThrHisCys 685       695       705       715       725       735       745
TTCATTGATTACCCAAAGAAGGAGGACTACATCGTCTACCTGGGTCGCTCAAGGCTTAACTCCAACACGCAAGGG
PheIleAspTyrProLysLysGluAspTyrIleValTyrLeuGlyArgSerArgLeuAsnSerAsnThrGlnGly 760       770       780       790       800       810       820
GAGATGAAGTTTGAGGTGGAAAACCTCATCCTACACAAGGACTACAGCGCTGACACGCTTGCTCACCACAATGAC
GluMetLysPheGluValGluAsnLeuIleLeuHisLysAspTyrSerAlaAspThrLeuAlaHisHisAsnAsp
```

FIG. 43-(2)

```
           835       845       855       865       875       885       895
ATTGCCTTGCTGAAGATCCGTTCCAAGGAGGGCAGGTGTGCGCAGCCATCCCGGACTATACAGACCATCTGCCTG
IleAlaLeuLeuLysIleArgSerLysGluGlyArgCysAlaGlnProSerArgThrIleGlnThrIleCysLeu 910       920       930       940       950       960       970
CCCTCGATGTATAACGATCCCCAGTTTGGCACAAGCTGTGAGATCACTGGCTTTGGAAAAGAGAATTCTACCGAC
ProSerMetTyrAsnAspProGlnPheGlyThrSerCysGluIleThrGlyPheGlyLysGluAsnSerThrAsp 985       995      1005      1015      1025      1035      1045
TATCTCTATCCGGAGCAGCTGAAAATGACTGTTGTGAAGCTGATTTCCCACCGGGAGTGTCAGCAGCCCCACTAC
TyrLeuTyrProGluGlnLeuLysMetThrValValLysLeuIleSerHisArgGluCysGlnGlnProHisTyr 1060      1070      1080      1090      1100      1110      1120
TACGGCTCTGAAGTCACCACCAAAATGCTGTGTGCTGCTGACCCACAGTGGAAAACAGATTCCTGCCAGGGAGAC
TyrGlySerGluValThrThrLysMetLeuCysAlaAlaAspProGlnTrpLysThrAspSerCysGlnGlyAsp 1135      1145      1155      1165      1175      1185      1195
TCAGGGGGACCCCTCGTCTGTTCCCTCCAAGGCCGCATGACTTTGACTGGAATTGTGAGCTGGGGCCGTGGATGT
SerGlyGlyProLeuValCysSerLeuGlnGlyArgMetThrLeuThrGlyIleValSerTrpGlyArgGlyCys 1210      1220      1230      1240      1250      1260      1270
GCCCTGAAGGACAAGCCAGGCGTCTACACGAGAGTCTCACACTTCTTACCCTGGATCCGCAGTCACACCAAGGAA
AlaLeuLysAspLysProGlyValTyrThrArgValSerHisPheLeuProTrpIleArgSerHisThrLysGlu 1285      1295
GAGAATGGCCTGGCCCTCTGA
GluAsnGlyLeuAlaLeu***
```

PLASMINOGEN ACTIVATOR

FIELD OF THE INVENTION

This invention relates to a novel plasminogen activator constructed by using recombinant DNA technology, a deoxyribonucleic acid (DNA) coding for the activator, a recombinant plasmid containing the DNA, a microbial or animal cell transformed with the recombinant plasmid, and a method of producing the plasminogen activator using said microbial or animal cell.

The novel plasminogen activator according to the invention is stable against the protease (thrombin) which cleaves the urokinase type plasminogen activator into an inactive double-chain structure. Therefore, it can be readily recovered and purified to a pure form. This novel plasminogen activator has an increased specific activity, is stable and has good thrombolytic activity. Accordingly, the novel plasminogen activator according to the invention can expectedly be used as a therapeutic agent for the treatment and/or prevention of cerebral thrombosis and myocardial infarction, among others.

BACKGROUND OF THE INVENTION

Urokinase (UK), streptokinase (SK) and tissue plasminogen activator (t-PA) are currently used as thrombolytic agents.

The primary structure of human urokinase has been described by Heynecker et al. (JP-A-59-51300, the term "JP-A" used herein means "an unexamined published Japanese patent application") and the folded structure thereof has been described as well as shown in FIG. 1. This folded structure, which has been proposed based on homology to other proteins, can be divided into the following three domains. The first domain on the N-terminal side is a domain homologous to epidermal growth factor. Hereinafter, this domain is referred to as "growth factor domain". The second domain is the so-called "kringle domain". The third domain at the C terminal is the so-called serine protease domain. Hereinafter, the third domain is referred to as "protease domain".

Human urokinase occurs in two forms, a single-chain form and a double-chain form. The single chain form of UK is called prourokinase (hereinafter referred to as "pro-UK") and, in such a structure, it has no thrombolytic activity. Only upon cleavage by plasmin into a double-chain structure, can it exhibit thrombolytic activity. However, when pro-UK is cleaved by thrombin, which cleaves pro-UK at a site two amino acids upstream from the plasmin cleavage site, the resulting double-chain structure has no thrombolytic activity any longer [Ichinose et al., J. Biol. Chem., 261, 3486 (1986)]. Thus, after administration into the blood, pro-UK is cleaved by thrombin which is present in the blood into an inactive double-chain structure. Furthermore, if the purification process for pro-UK is contaminated by a thrombin-like protease, the protease will possibly cleave pro-UK into an inactive double-chain structure.

To prevent pro-UK from being cleaved by a thrombin-like protease, a pro-UK derivative resulting from the introduction of a substitute amino acid into the thrombin cleavage site at position $P_1$ or $P_1'$, has been proposed (EP-A-0200451 and JP-A-62-143686).

However, since the thrombin cleavage site is separated by only two amino acids from the plasmin cleavage site, the substitute amino acid introduced in the vicinity of the plasmin cleavage site namely at $P_3$ to $P_1'$, simultaneously makes it difficult for plasmin cleavage to occur, hence the conversion of the pro-UK derivative obtained into an active form becomes difficult and a decreased specific activity results. In fact, with the pro-UK derivative mentioned above, in which the position of amino acid substitution is $P_3$ or $P_2$ relative to the plasmin cleavage site, a decrease in susceptibility to plasmin, hence a decrease in specific activity, has been observed.

As regards the numbering of the amino acid residues of the substrate peptide to be cleaved, the peptide bond to be cleaved is represented by $-P_1-P_1'-$ and the amino acids on the carboxyl side to the peptide bond to be cleaved are given position codes $P_1, P_2, P_3, P_4$ etc. from the amino acid constituting the carboxyl side of said peptide bond toward the amino terminus. The amino acids on the amino side of this bond are given position codes $P_1', P_2', P_3', P_4'$ etc. from the amino acid constituting the amino side of said peptide bond toward the carboxyl terminus.

It is an object of the invention to develop a novel pro-UK derivative which is stable against any thrombin-like protease capable of inactivating pro-UK and shows no substantial decrease in specific activity.

Heretofore, reports have been published on the construction of pro-UK derivatives, which are more or less resistant to cleavage by thrombin, by introducing a substitute amino acid in position $P_1$ with respect to the thrombin cleavage site (position $P_3$ with respect to the plasmin cleavage site; 156th amino acid of mature pro-UK) or position $P_1'$ with respect to the thrombin cleavage site ($P_2$ with respect to the plasmin cleavage site; 157th amino acid of mature pro-UK). However, since the position of amino acid substitution in these derivatives is only two or three amino acids away from the plasmin cleavage site, the pro-UK derivatives may possibly have a decreased specific activity as a result of a decrease in susceptibility to plasmin. In fact, the present inventors have confirmed that amino acid substitution in mature pro-UK at position 157 ($P_2$ with respect to the plasmin cleavage site) results in a decrease in specific activity. Furthermore, in the case of amino acid substitution at position 157, it has been found that there is another problem in addition to specific activity decrease. Namely, the resistance of the pro-UK derivatives to thrombin is still unsatisfactory.

SUMMARY OF THE INVENTION

In an attempt to solve such problems, the present inventors made a novel amino acid substitution in a unique site, that is in position 155 [proline (Pro)] of mature pro-UK. As a result, it was surprisingly found that the pro-UK derivatives obtained by amino acid substitution in position 155 are completely resistant to thrombin and, in addition, have an increased specific activity as compared with naturally occurring pro-UK.

The present invention provides a novel plasminogen activator of the human prourokinase type which is characterized in that the 155th [from the N terminus serine of mature human prourokinase] amino acid residue proline has been replaced by another amino acid residue. The invention further provides a DNA coding for the peptide constituting this activator, a recombinant plasmid with this DNA inserted in it, a microbial or animal cell transformed with this plasmid, and a method of producing this plasminogen activator which uses this microbial or animal cell.

BRIEF DESCRIPTION OF THE DRAWINGS

FIG. 7 (1) and (2) illustrate the levels of resistance of various pro-UK derivatives to thrombin in comparison with that of naturally occurring pro-UK to thrombin, the mark ○ being for naturally occurring pro-UK, ○ for the pro-UK derivative UK-T6, Δ for the pro-UK derivative UK-T4, Δ for the pro-UK derivative UK-S3 and □ for the pro-UK derivative UK-T. In (1) and (2), the thrombin concentrations are 5.0 IU/ml and 100 IU/ml, respectively.

FIG. 7 (3) illustrates the results of SDS-polyacrylamide gel electrophoresis of naturally occurring pro-UK and various pro-UK derivatives after treatment with 5.0 IU/ml of thrombin, comparatively showing the digestion of each single-chain polypeptide with time.

FIG. (8-1 8-2) illustrates the scheme for the synthesis of cDNA by the Okayama-Berg method and the construction of a recombinant plasmid DNA containing said cDNA.

Figure 9:
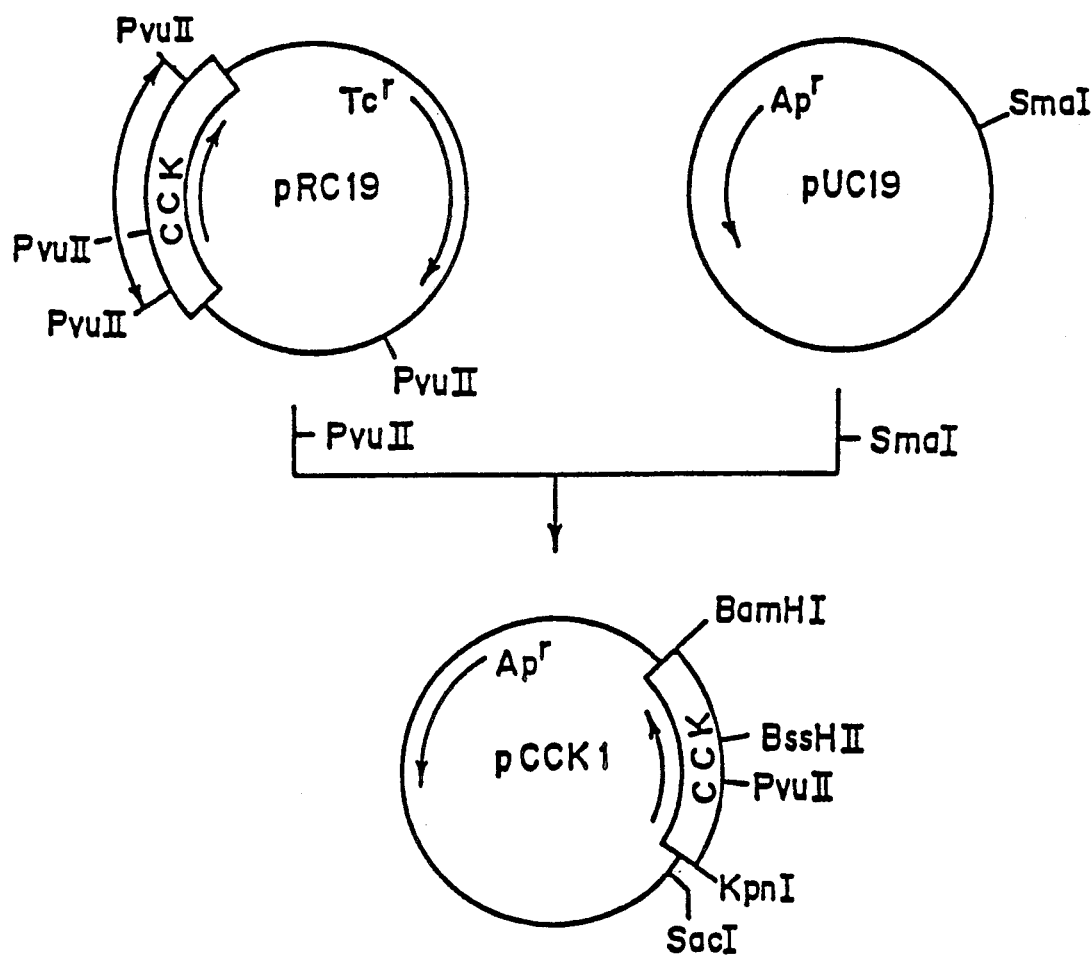

FIG. 9 illustrates the construction scheme for the plasmid DNA pCCK1.

Figure 10:
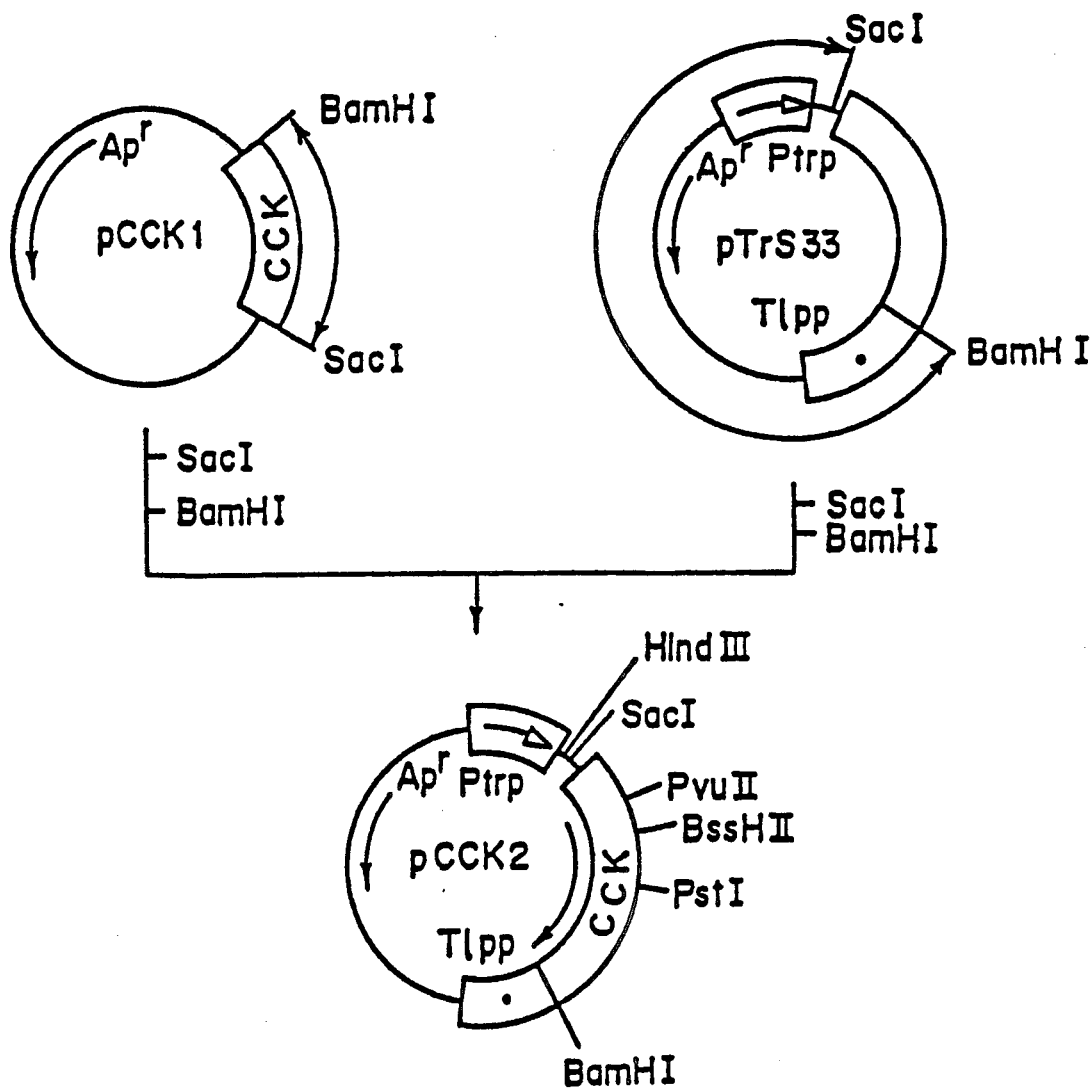

FIG. 10 illustrates the construction scheme for the plasmid pCCK2.

Figure 11:
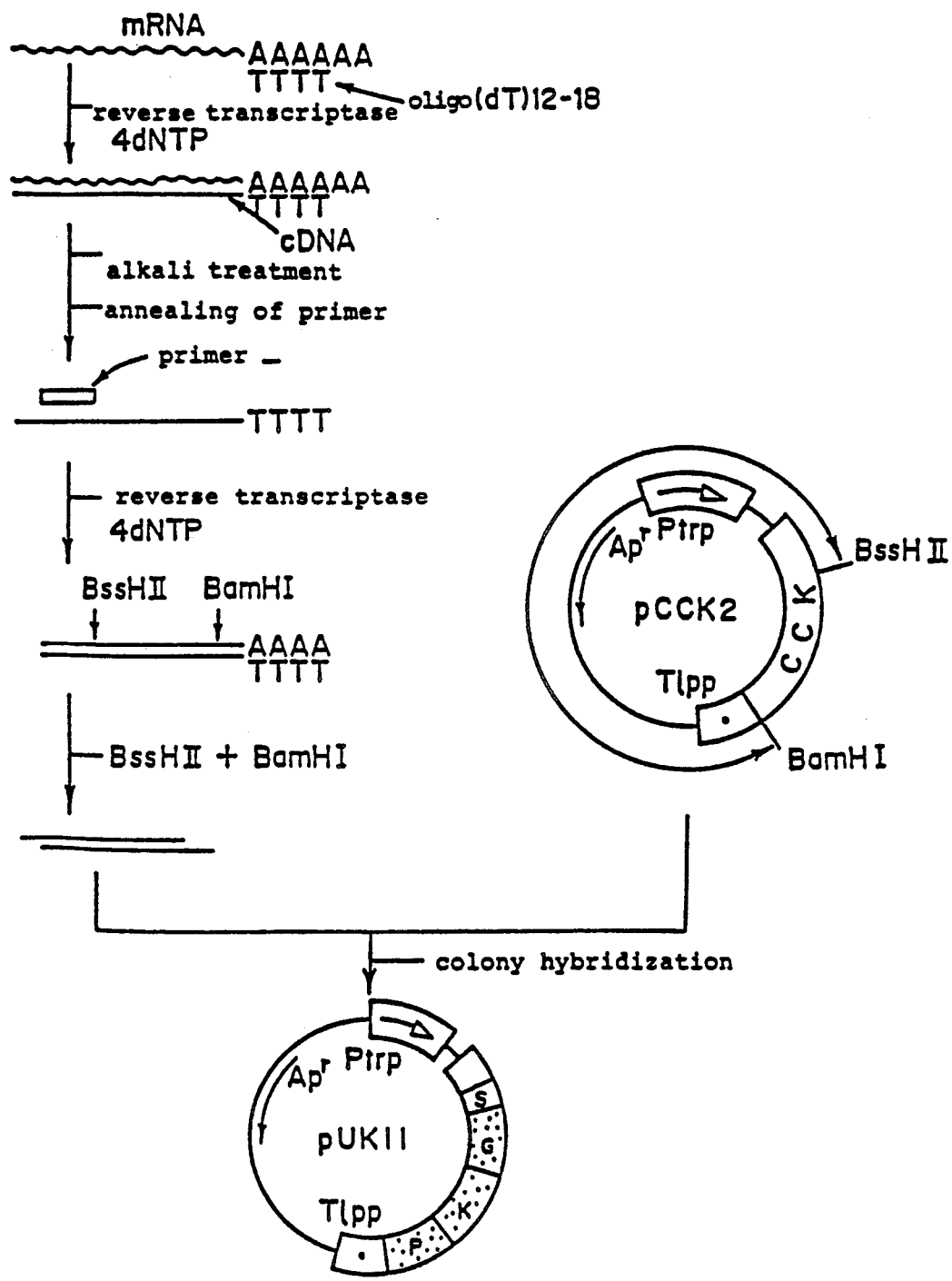

FIG. 11 illustrates the construction scheme for the plasmid pUK11 carrying human pro-UK cDNA.

Figure 12:
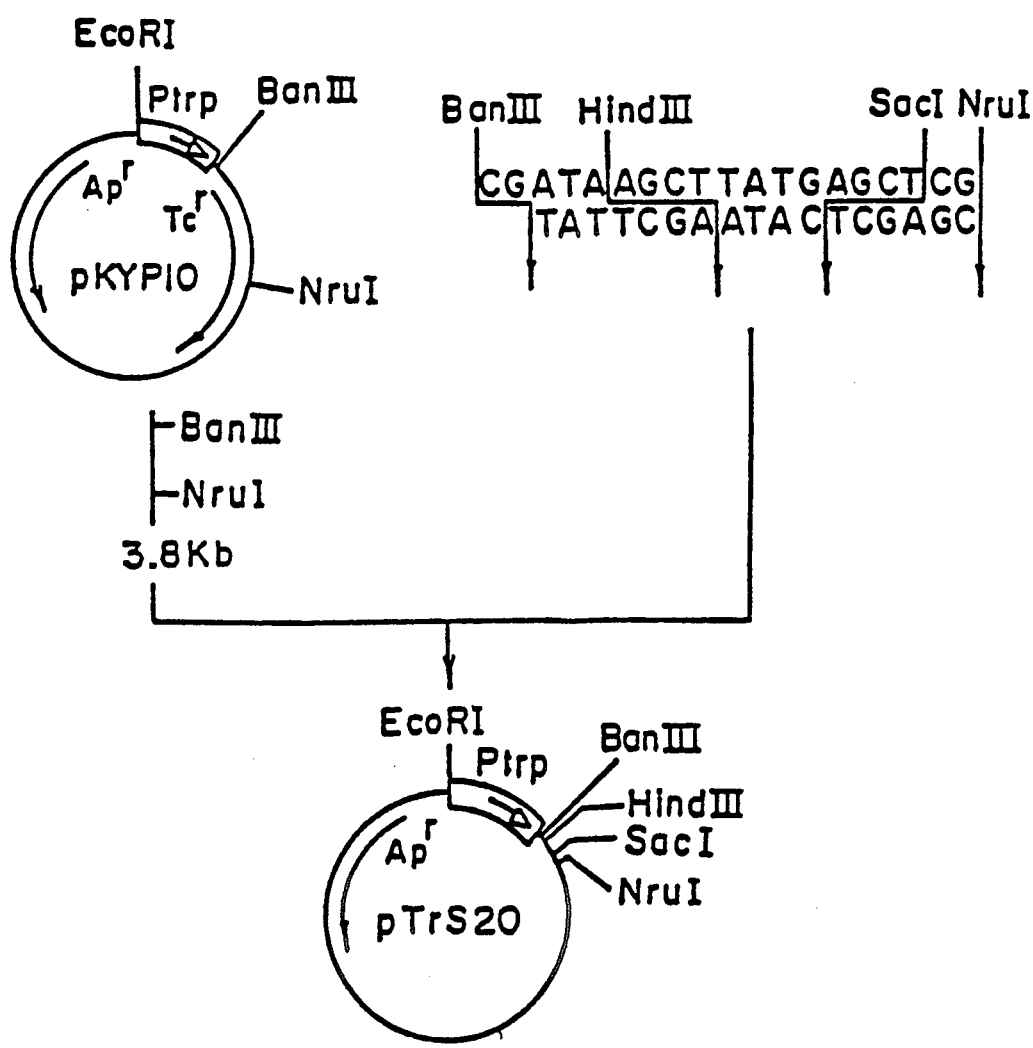

FIG. 12 illustrates the construction scheme for the plasmid pTrS20.

Figure 13:
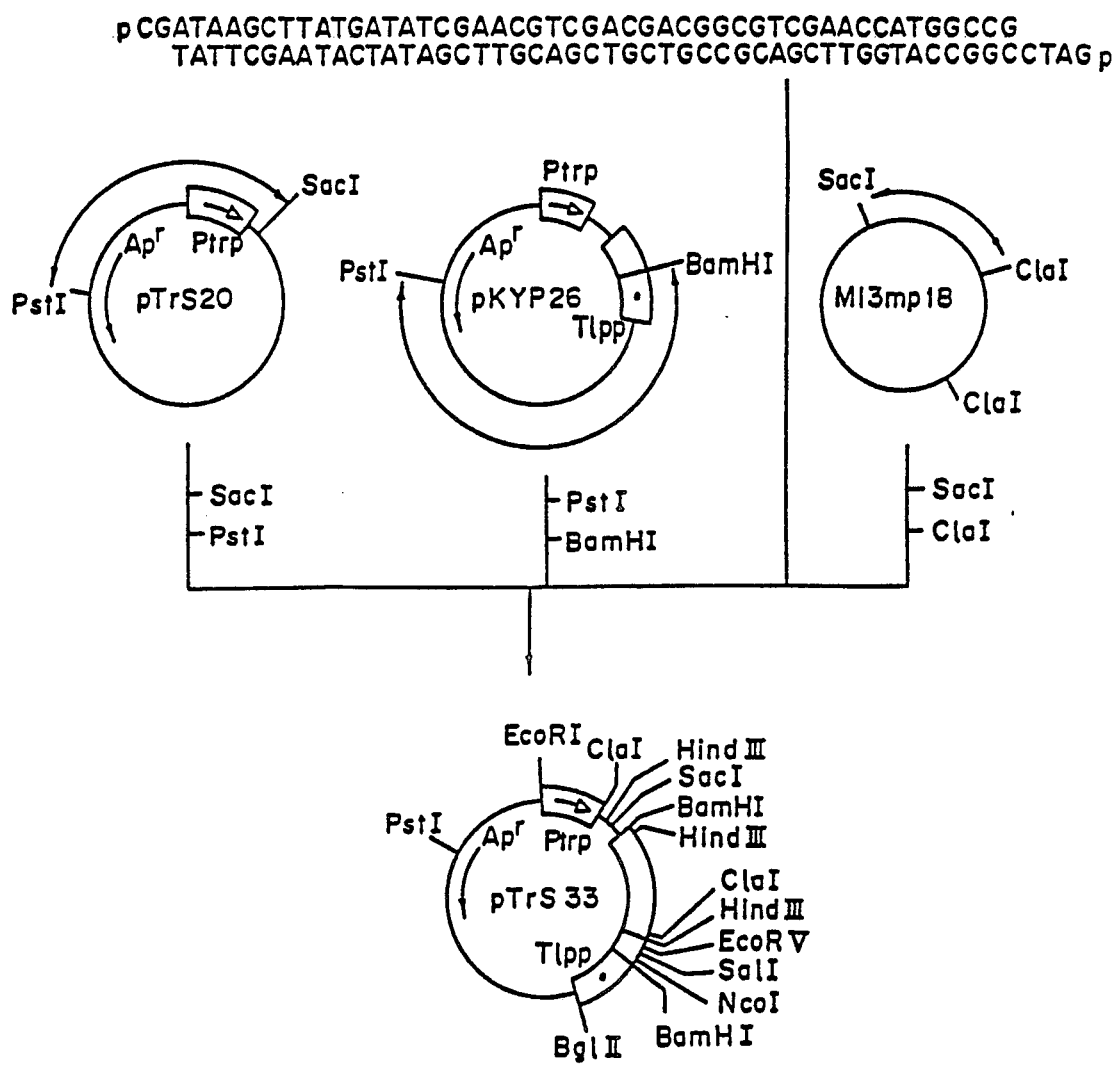

FIG. 13 illustrates the construction scheme for the plasmid pTrS33.

Figure 14:
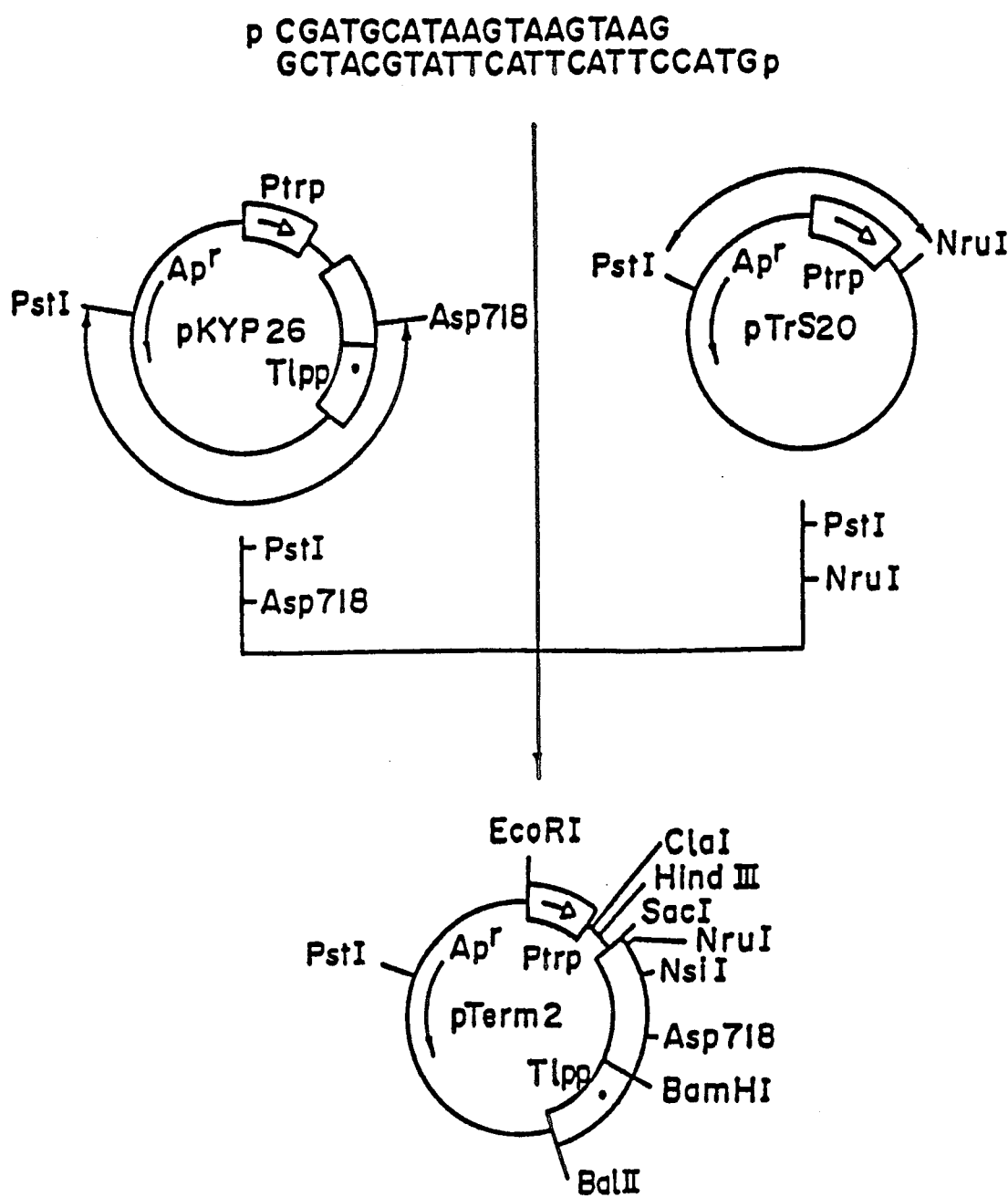

FIG. 14 illustrates the construction scheme for the plasmid pTerm2.

Figure 15:
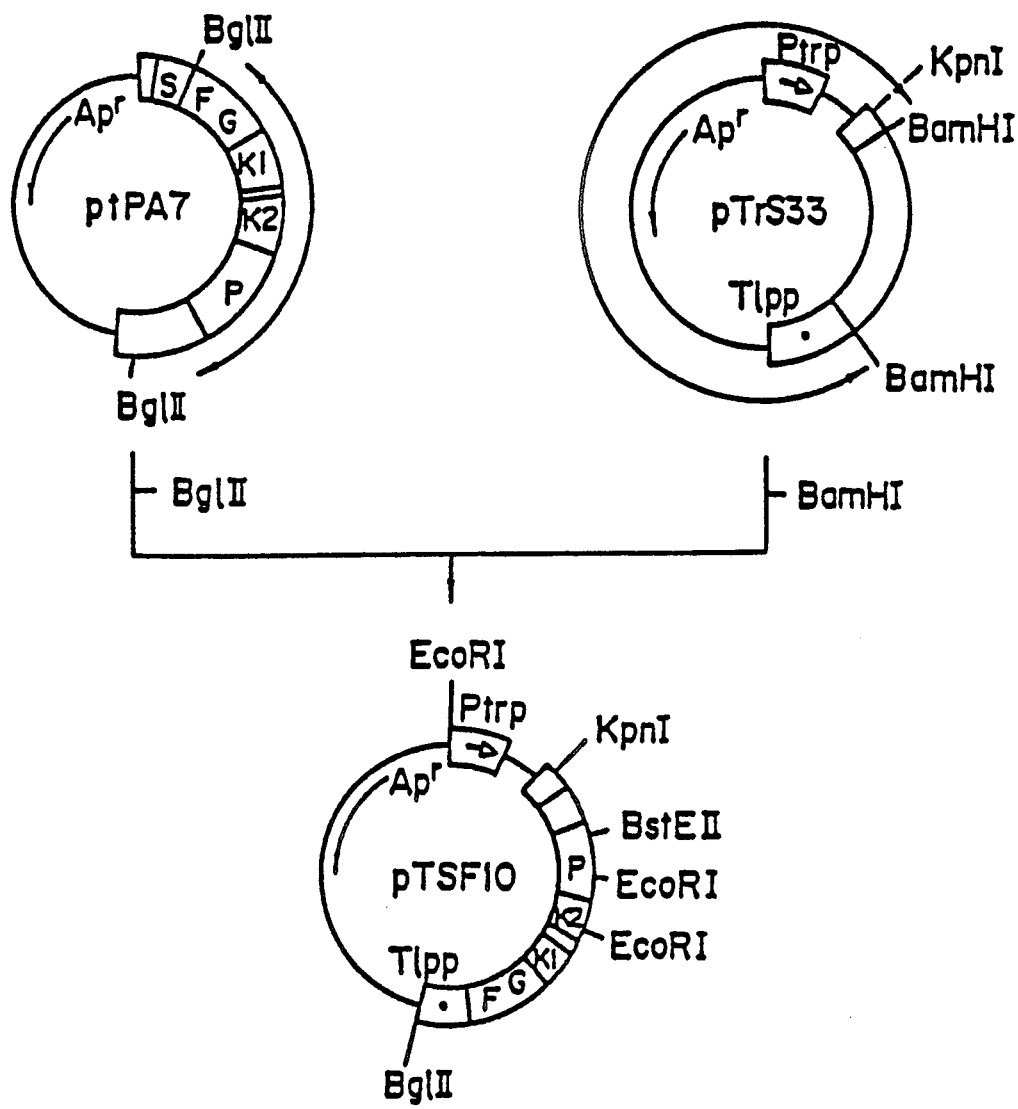

FIG. 15 illustrates the construction scheme for the plasmid pTSF10.

Figure 16:
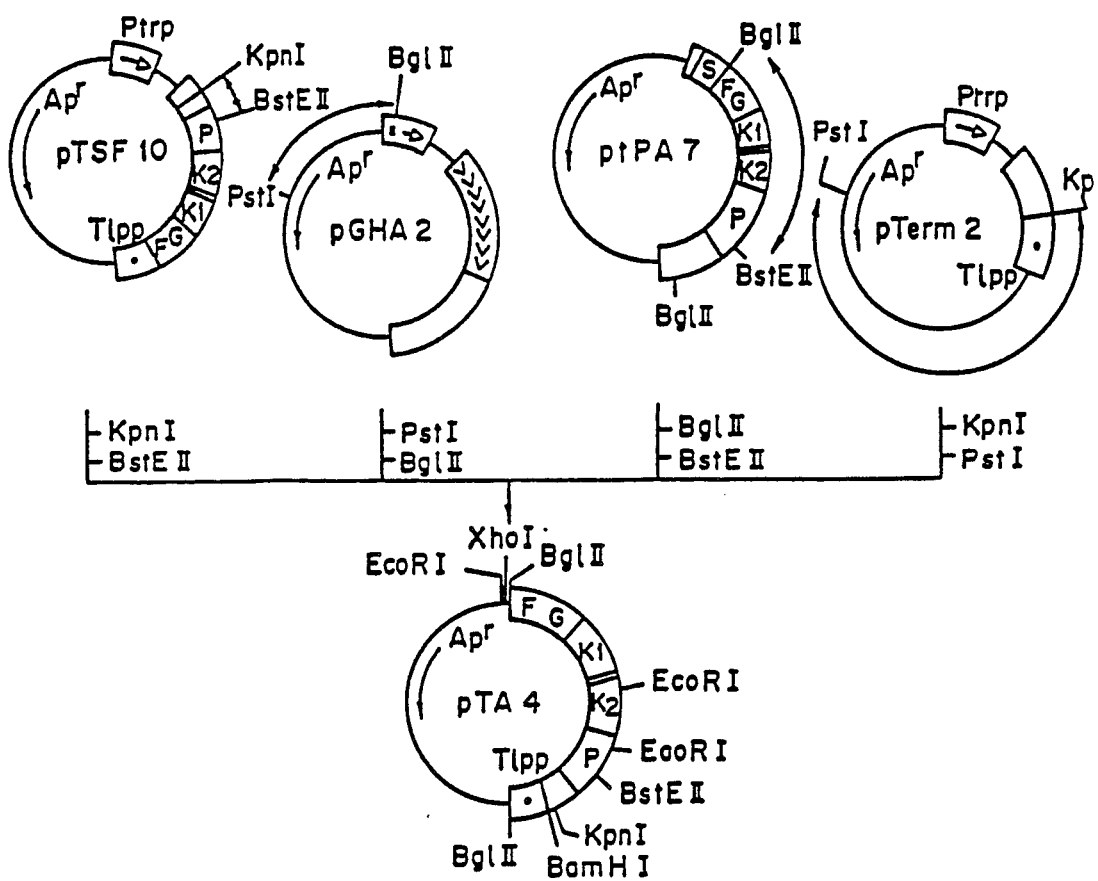

FIG. 16 illustrates the construction scheme for the plasmid pTA4.

Figure 17:
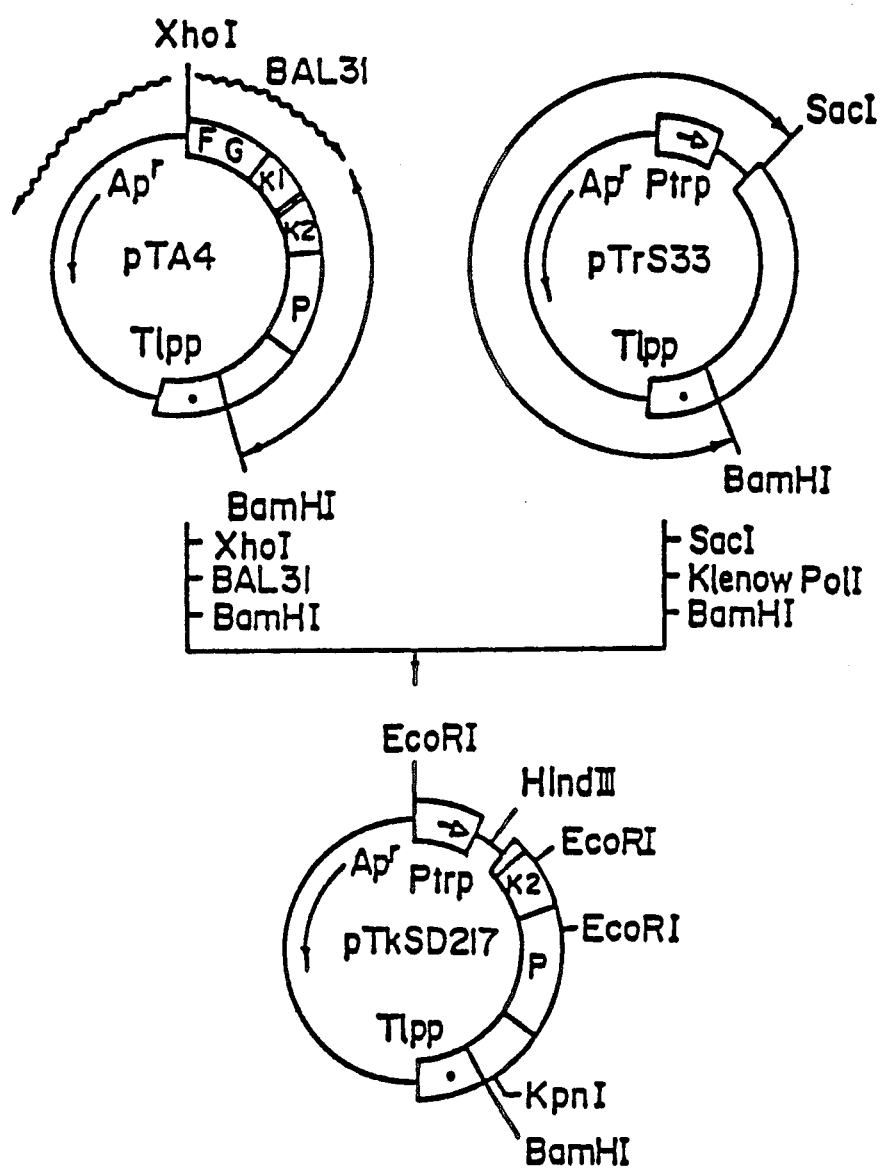

FIG. 17 illustrates the construction scheme for the plasmid pTkSD217.

Figure 18:
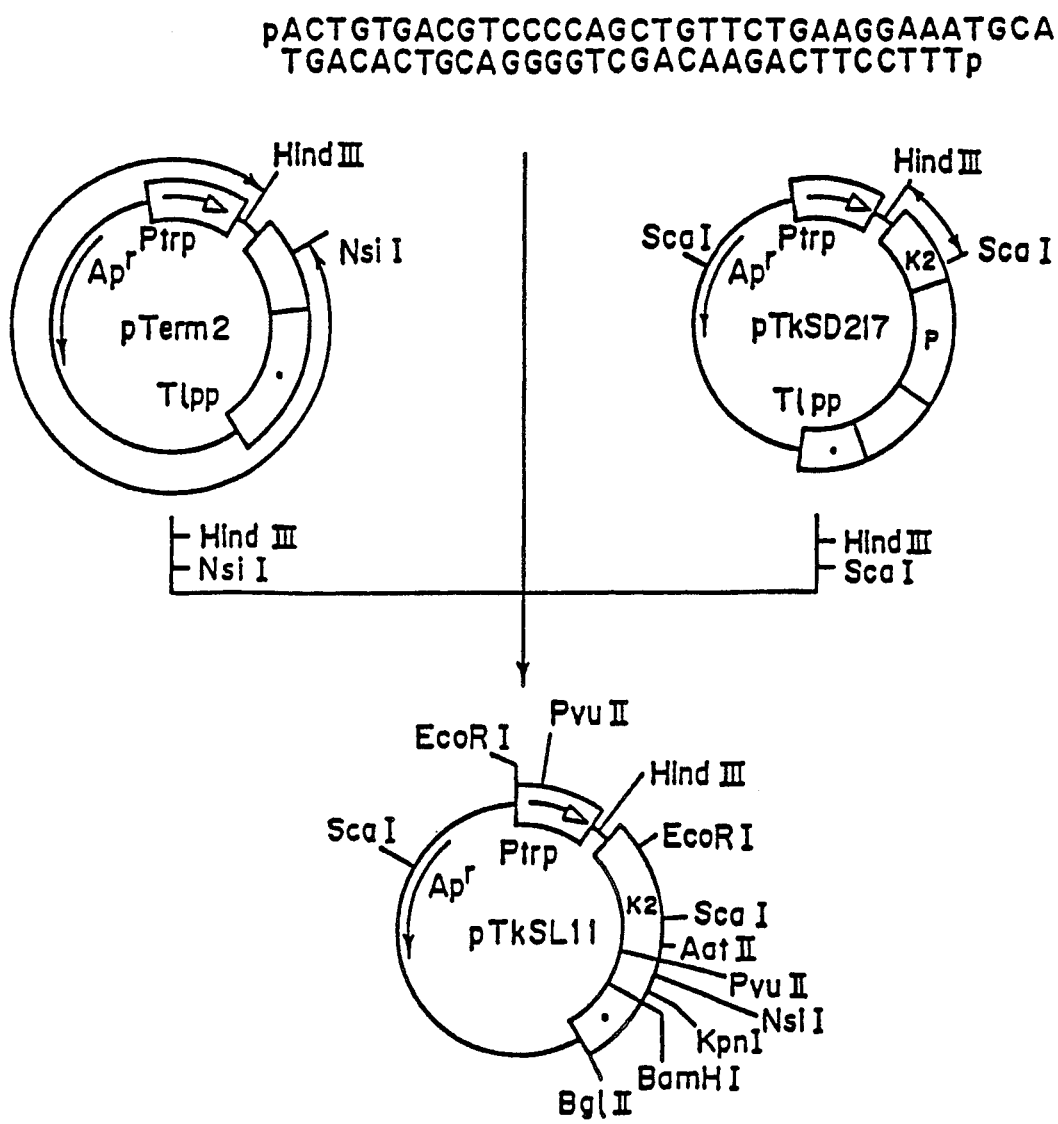

FIG. 18 illustrates the construction scheme for the plasmid pTkSL11.

Figure 19:
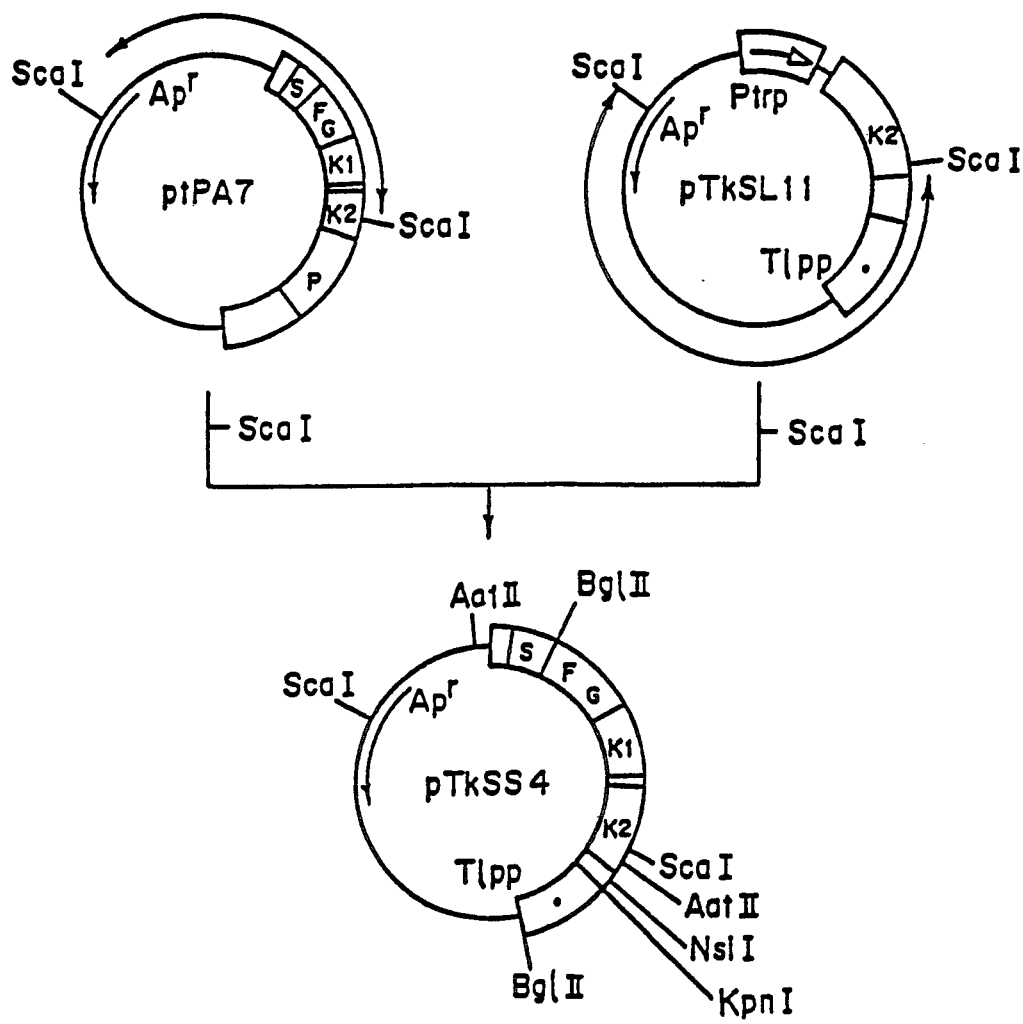

FIG. 19 illustrates the construction scheme for the plasmid pTkSS4.

Figure 20:
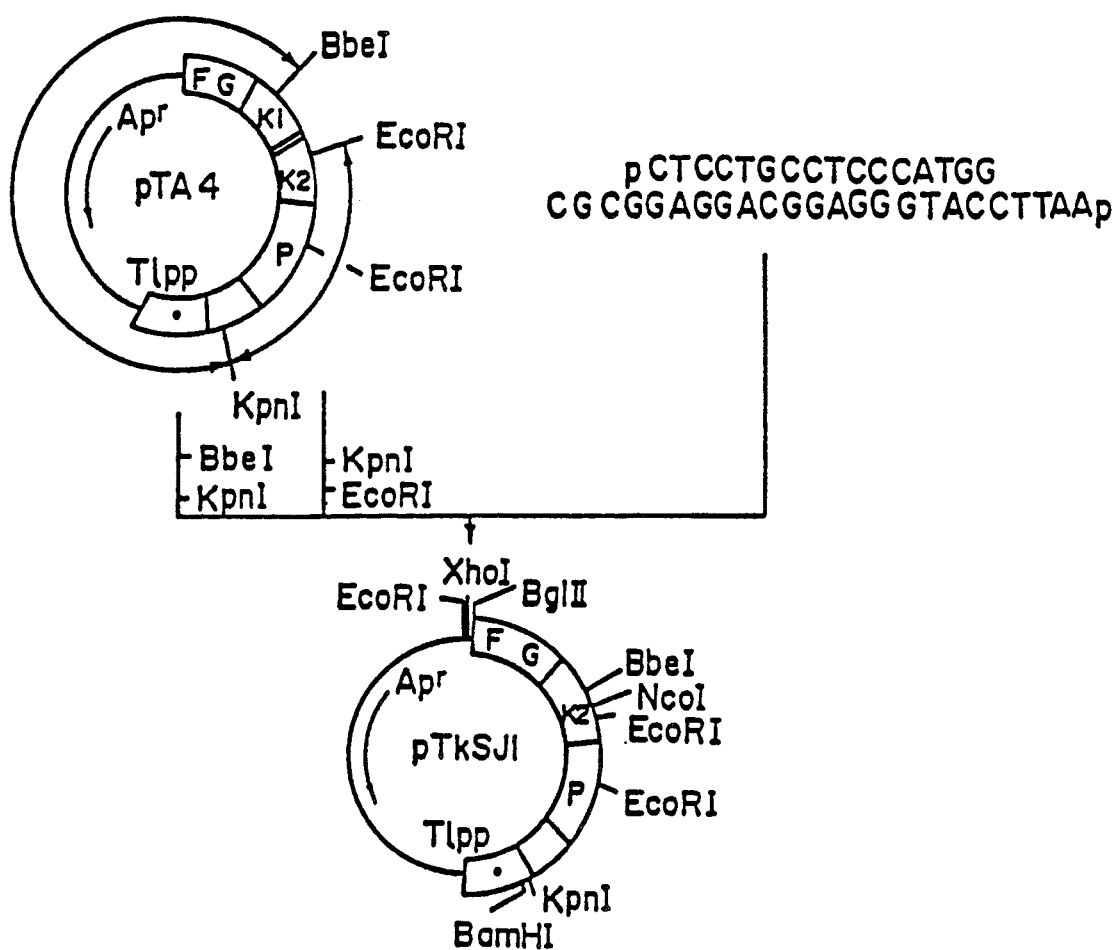

FIG. 20 illustrates the construction scheme for the plasmid pTkSJ1.

FIG. 21 illustrates the construction scheme for the plasmid pTkSR18.

FIG. 22 illustrates the construction scheme for the plasmid pUKA2.

Figure 23:
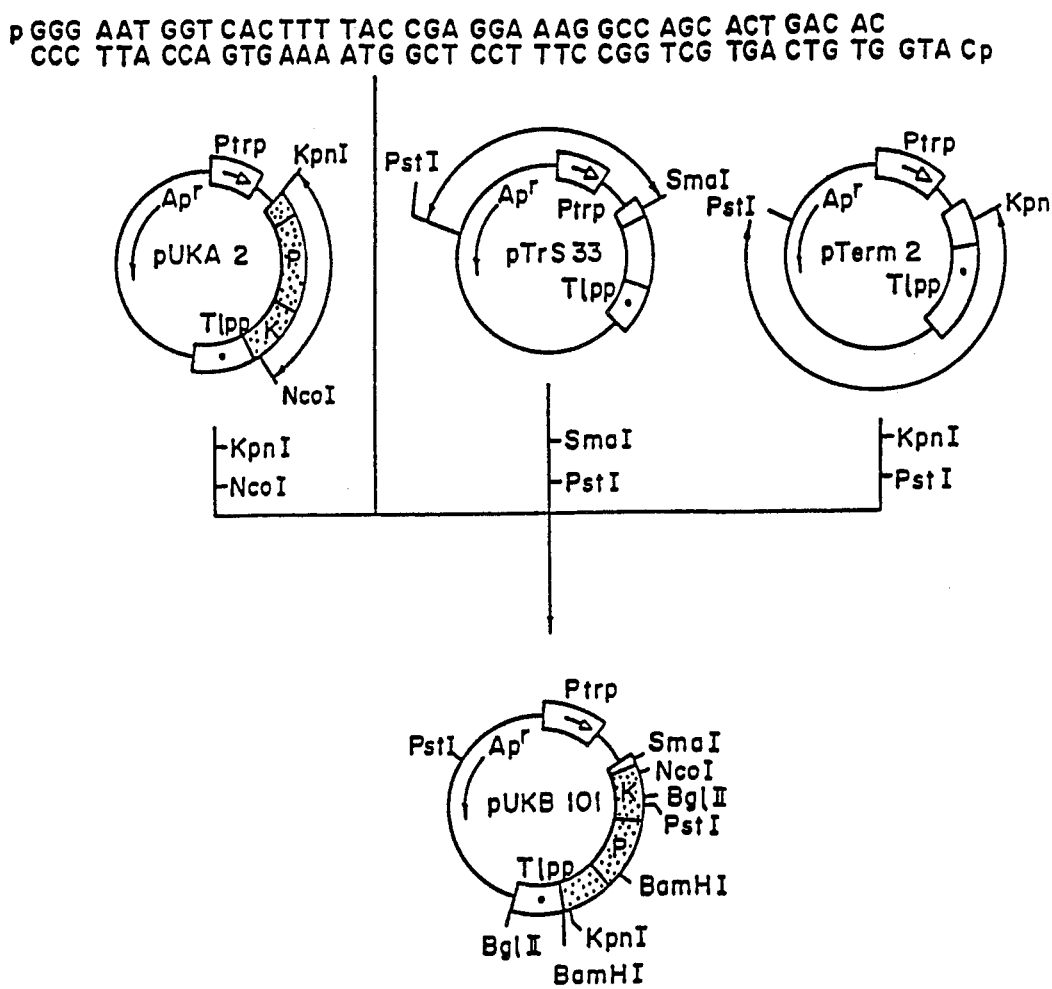

FIG. 23 illustrates the construction scheme for the plasmid pUKB101.

Figure 24:
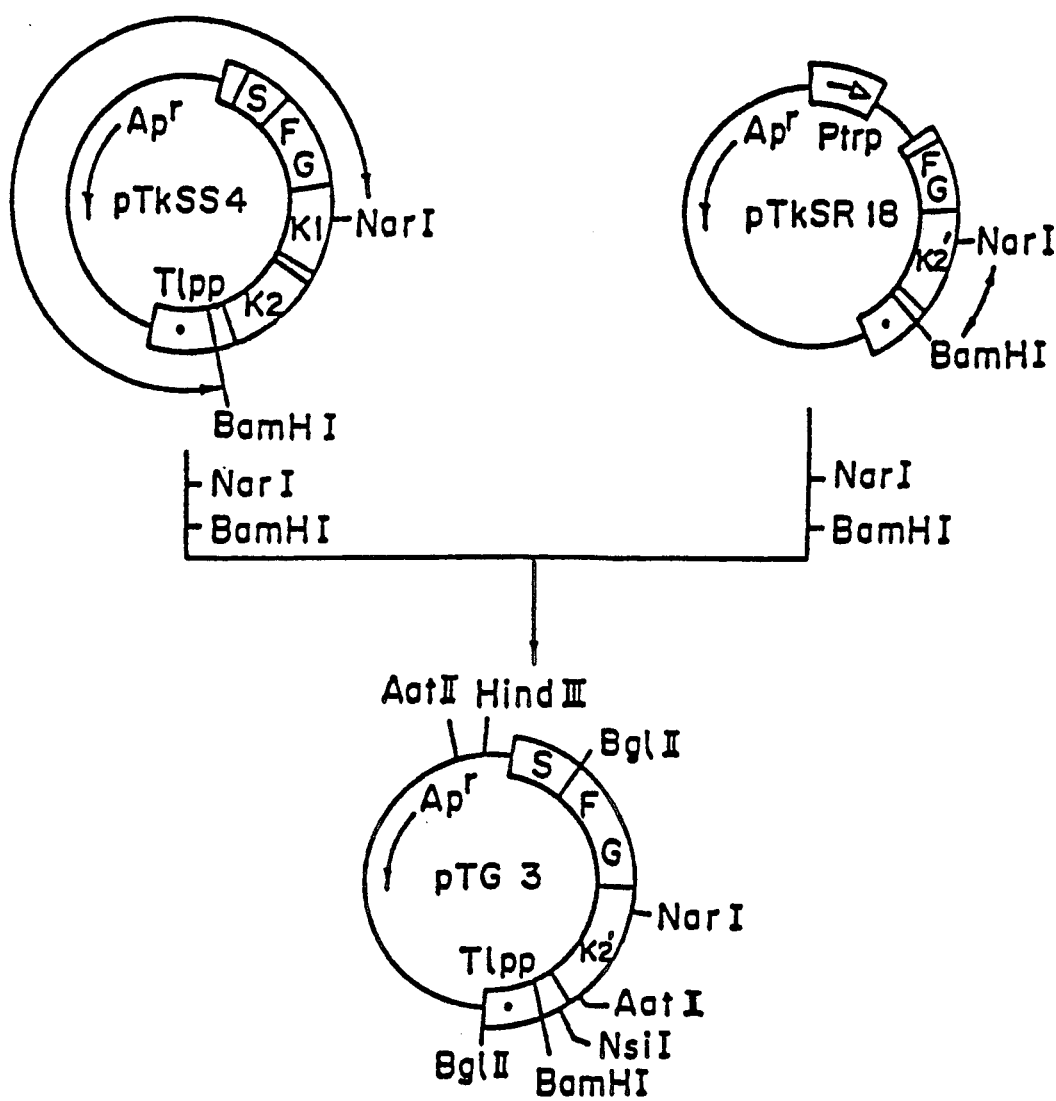

FIG. 24 illustrates the construction scheme for the plasmid pTG3.

Figure 25:
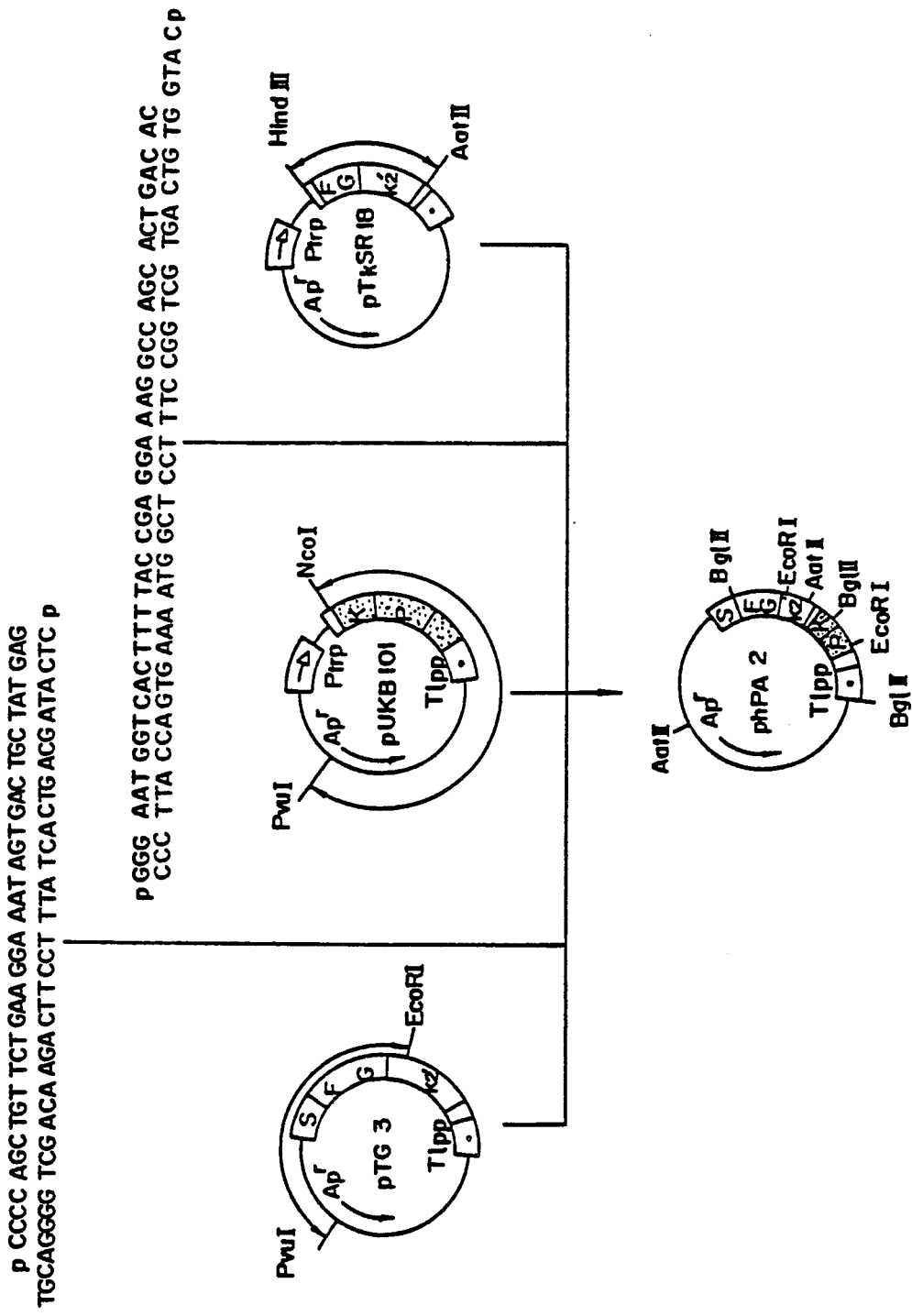

FIG. 25 illustrates the construction scheme for the plasmid phPA2.

Figure 26:
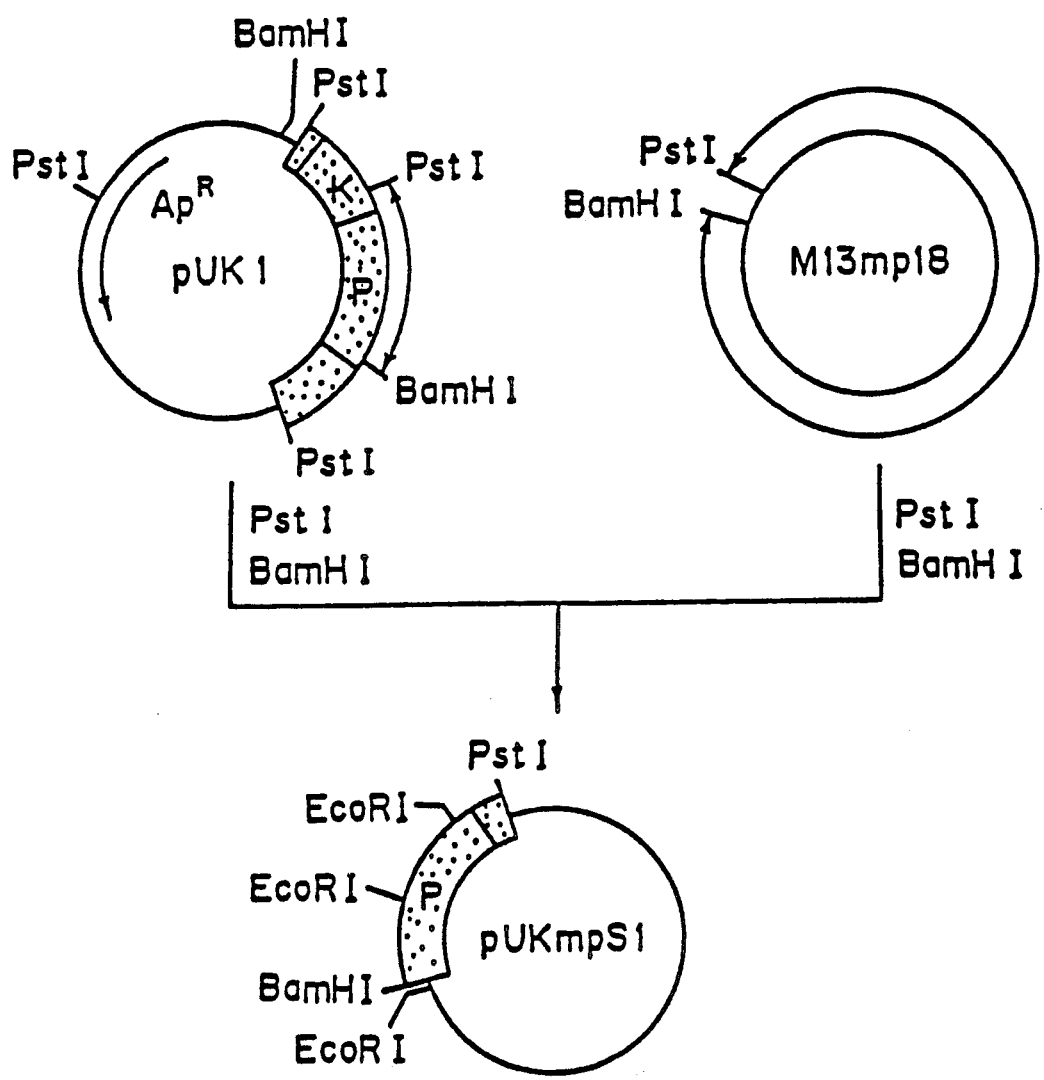

FIG. 26 illustrates the construction scheme for the single-stranded pUKmpS1.

Figure 27:
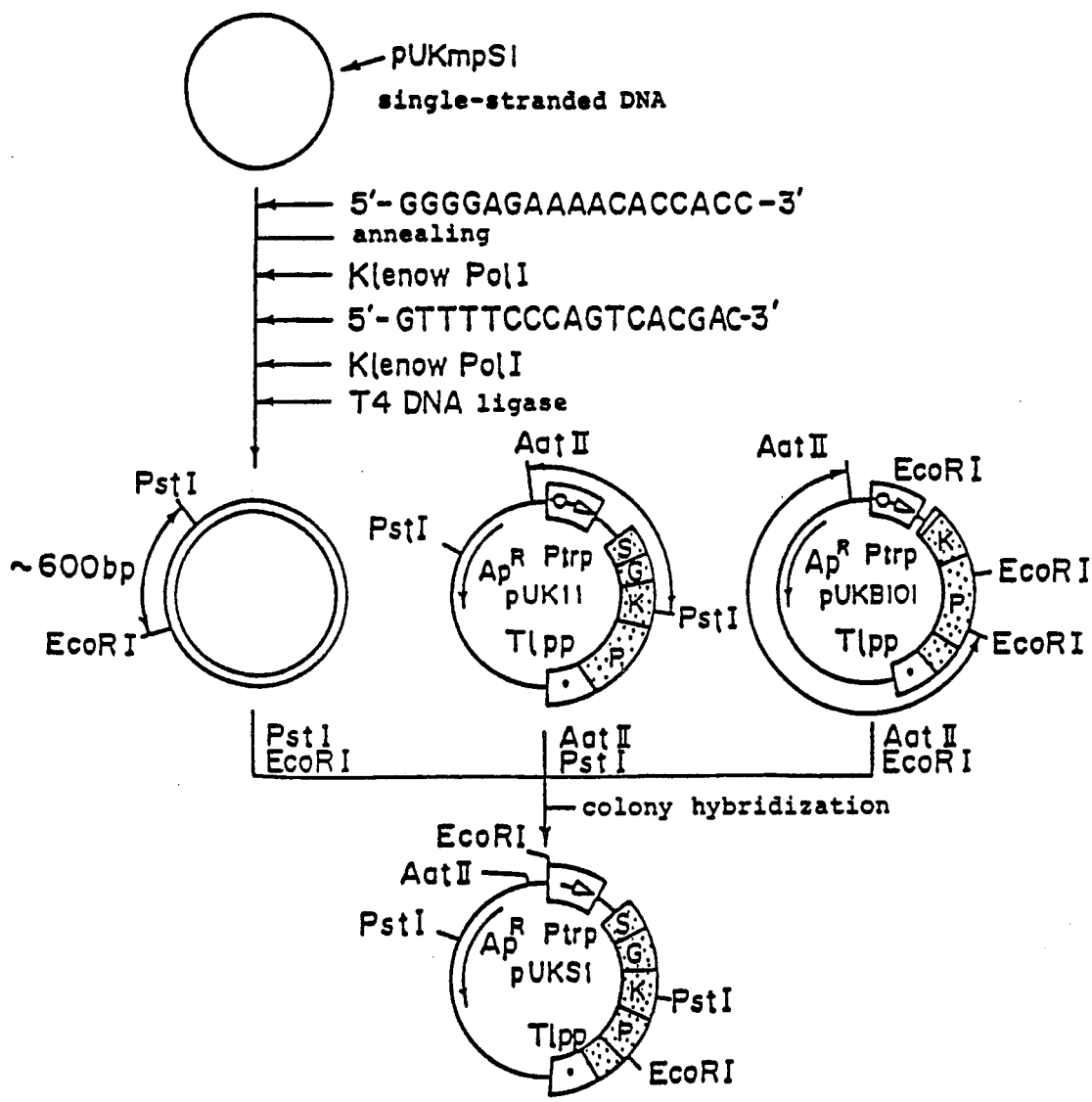

FIG. 27 illustrates the construction scheme for the plasmid pUKS1.

Figure 28:
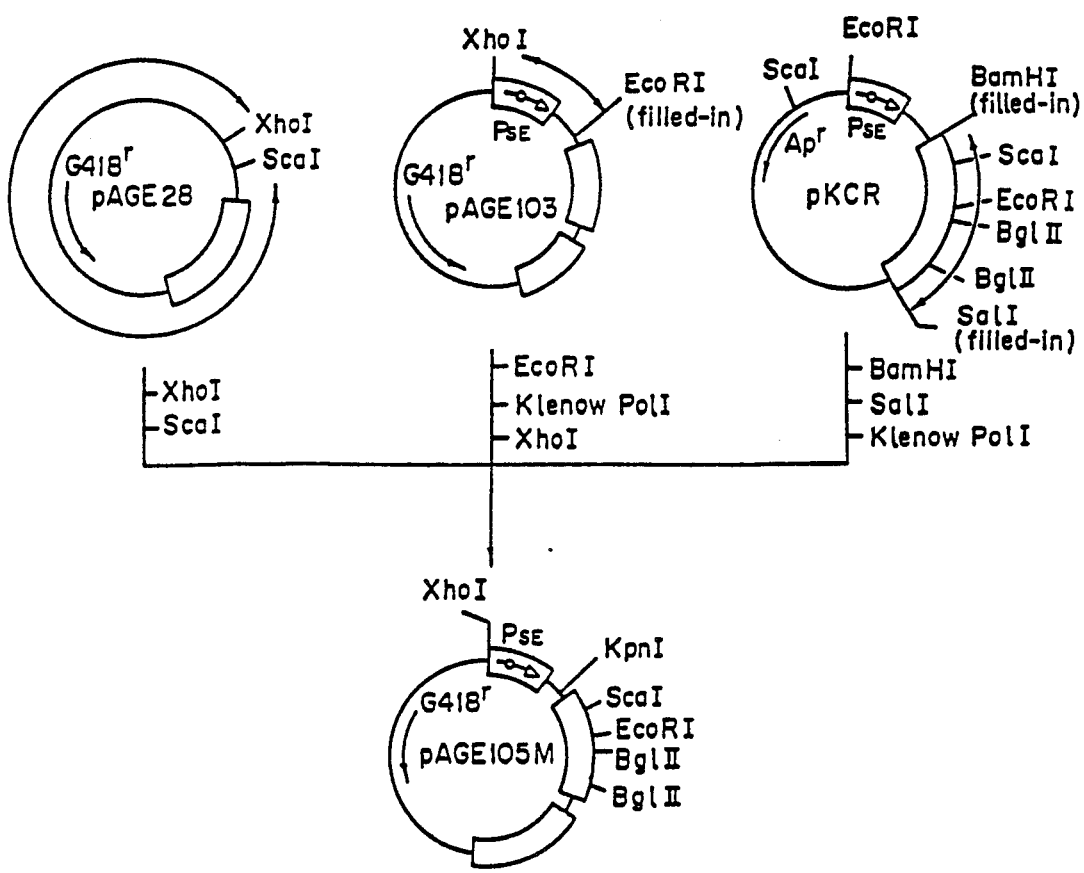

FIG. 28 illustrates the construction scheme for the plasmid pAGE105M.

Figure 29:
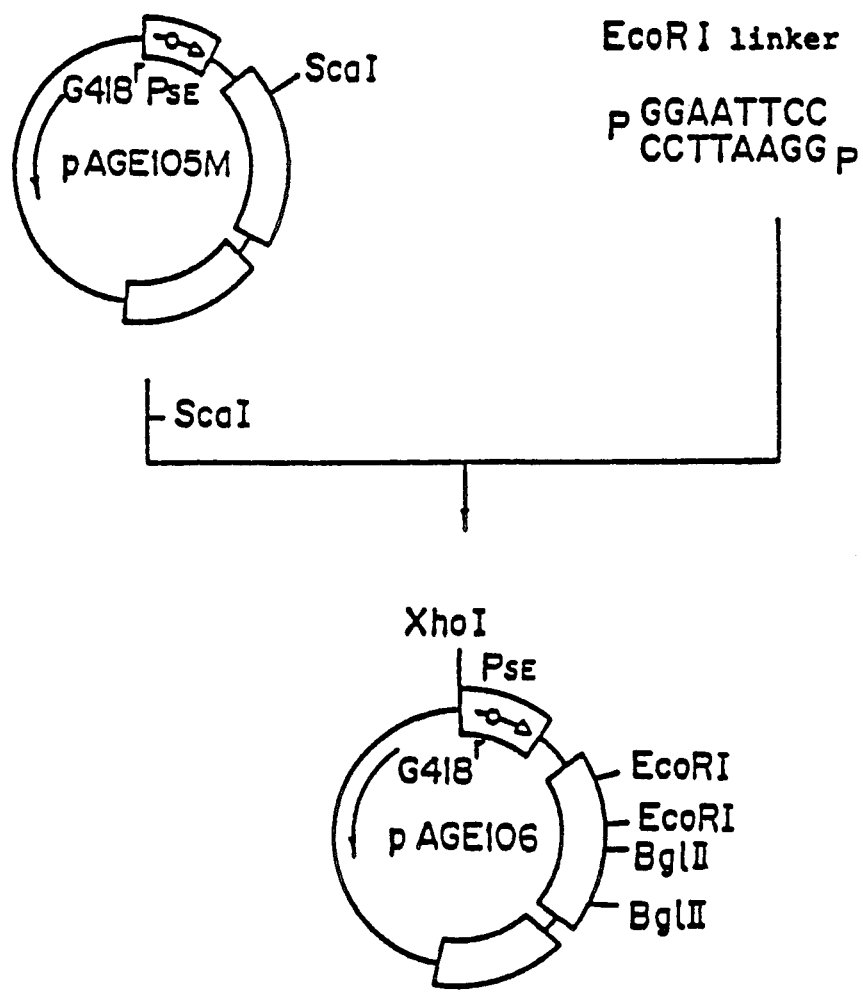

FIG. 29 illustrates the construction scheme for the plasmid pAGE106.

Figure 30:
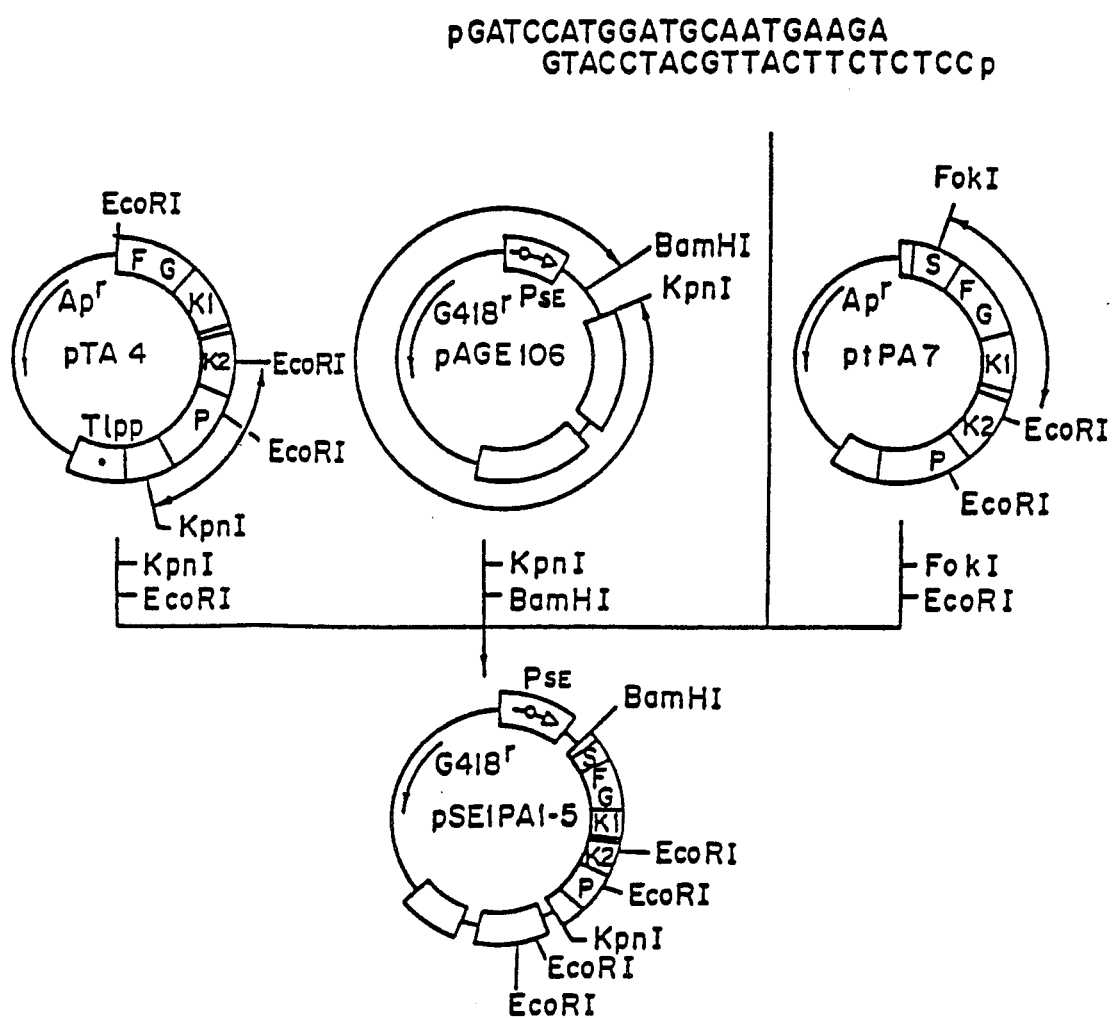

FIG. 30 illustrates the construction scheme for the plasmid pSE1PA1-5.

FIG. 31 illustrates the construction scheme for the plasmid pSE1PA1-9.

FIG. 32 illustrates the construction scheme for the plasmid pUC19H.

Figure 33:
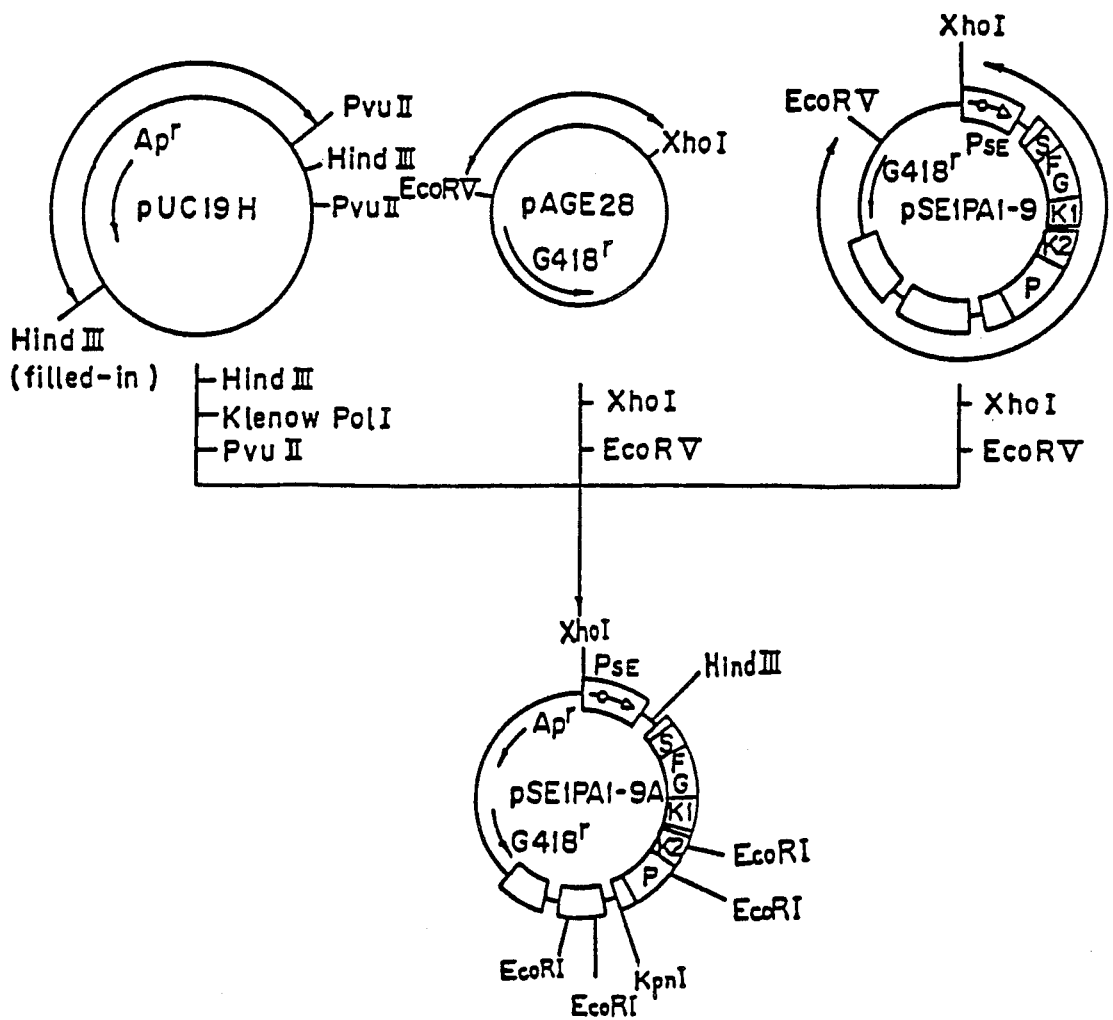

FIG. 33 illustrates the construction scheme for the plasmid pSE1PA1-9A.

Figure 34:
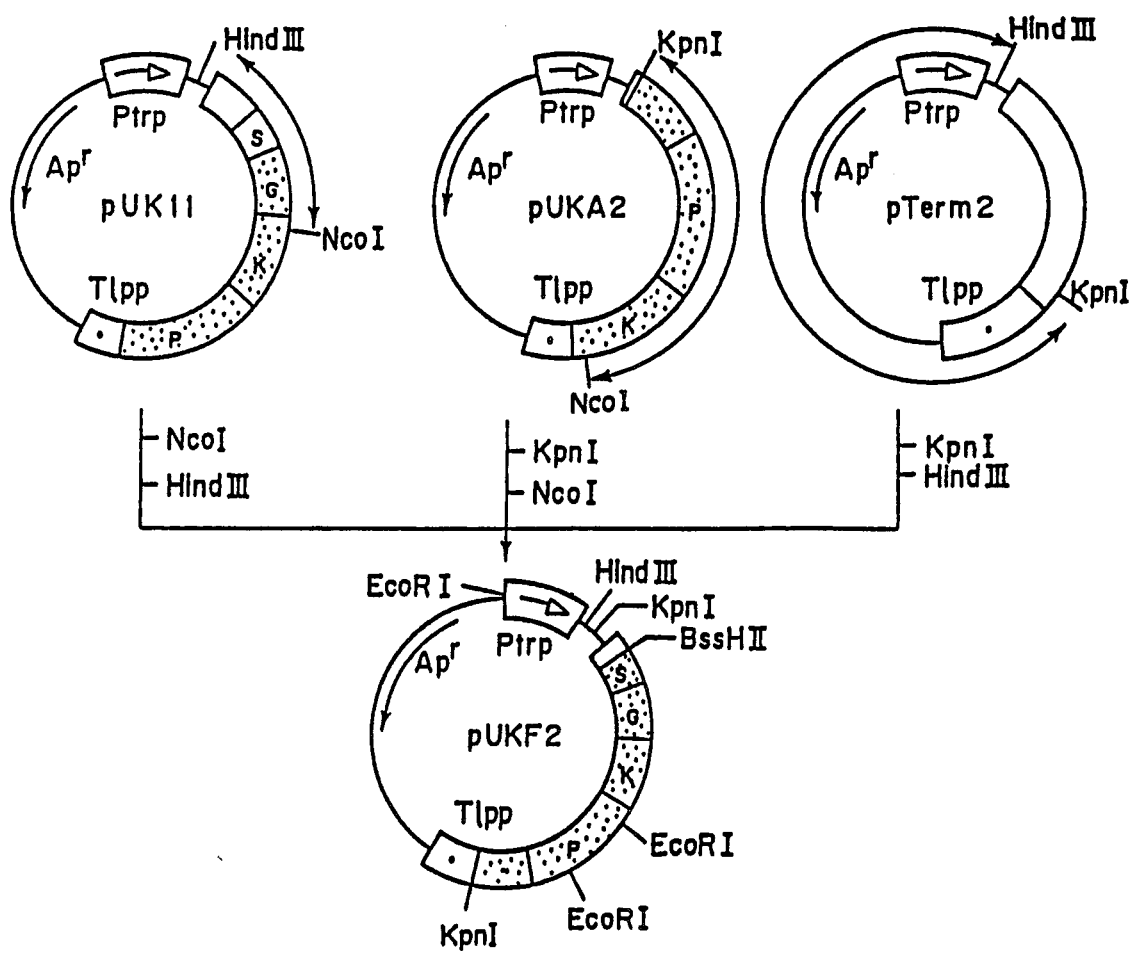

FIG. 34 illustrates the construction scheme for the plasmid pUKF2.

Figure 35:
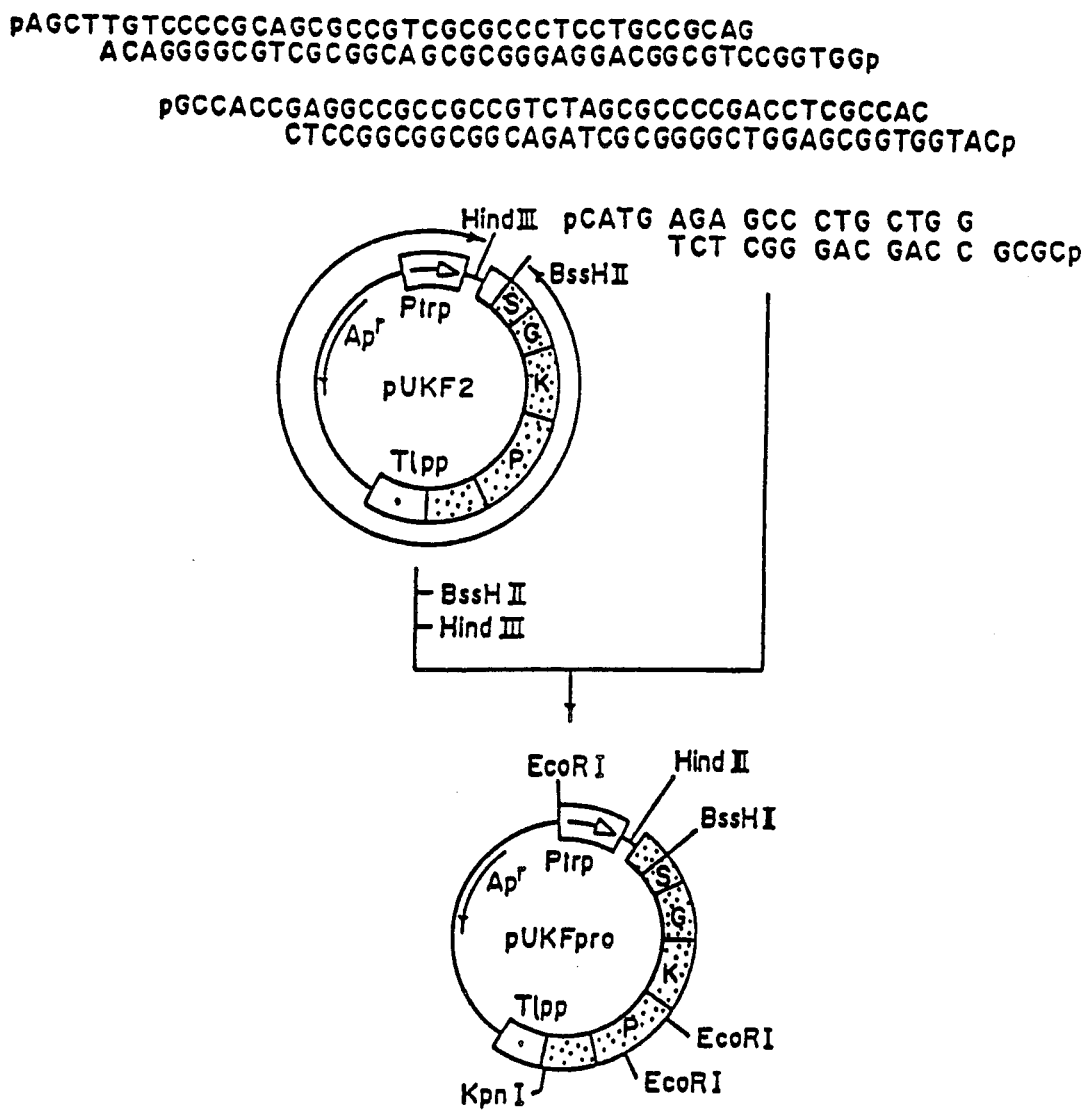

FIG. 35 illustrates the construction scheme for the plasmid pUKFpro.

Figure 36:
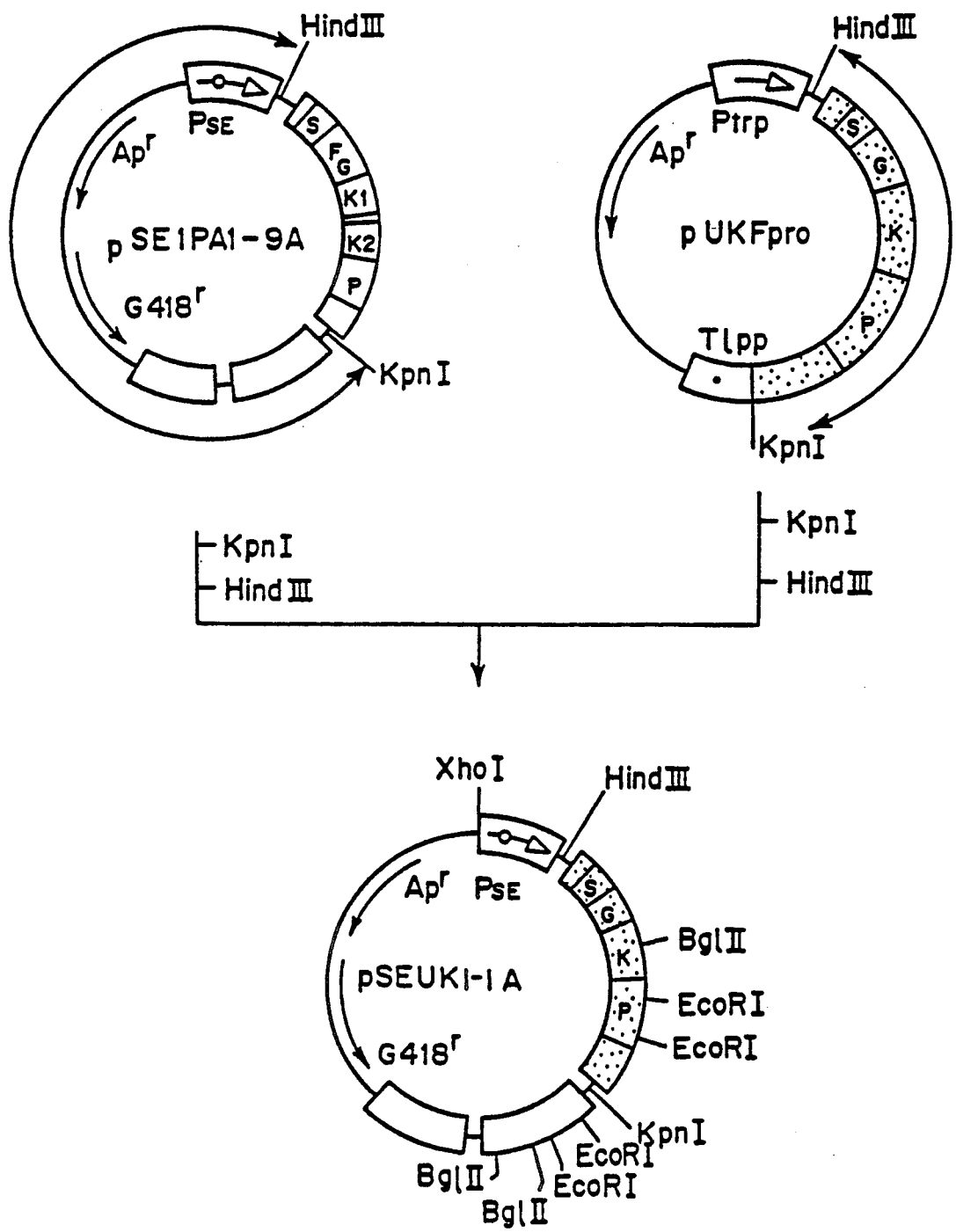

FIG. 36 illustrates the construction scheme for the plasmid pSEUK1-1A.

Figure 37:
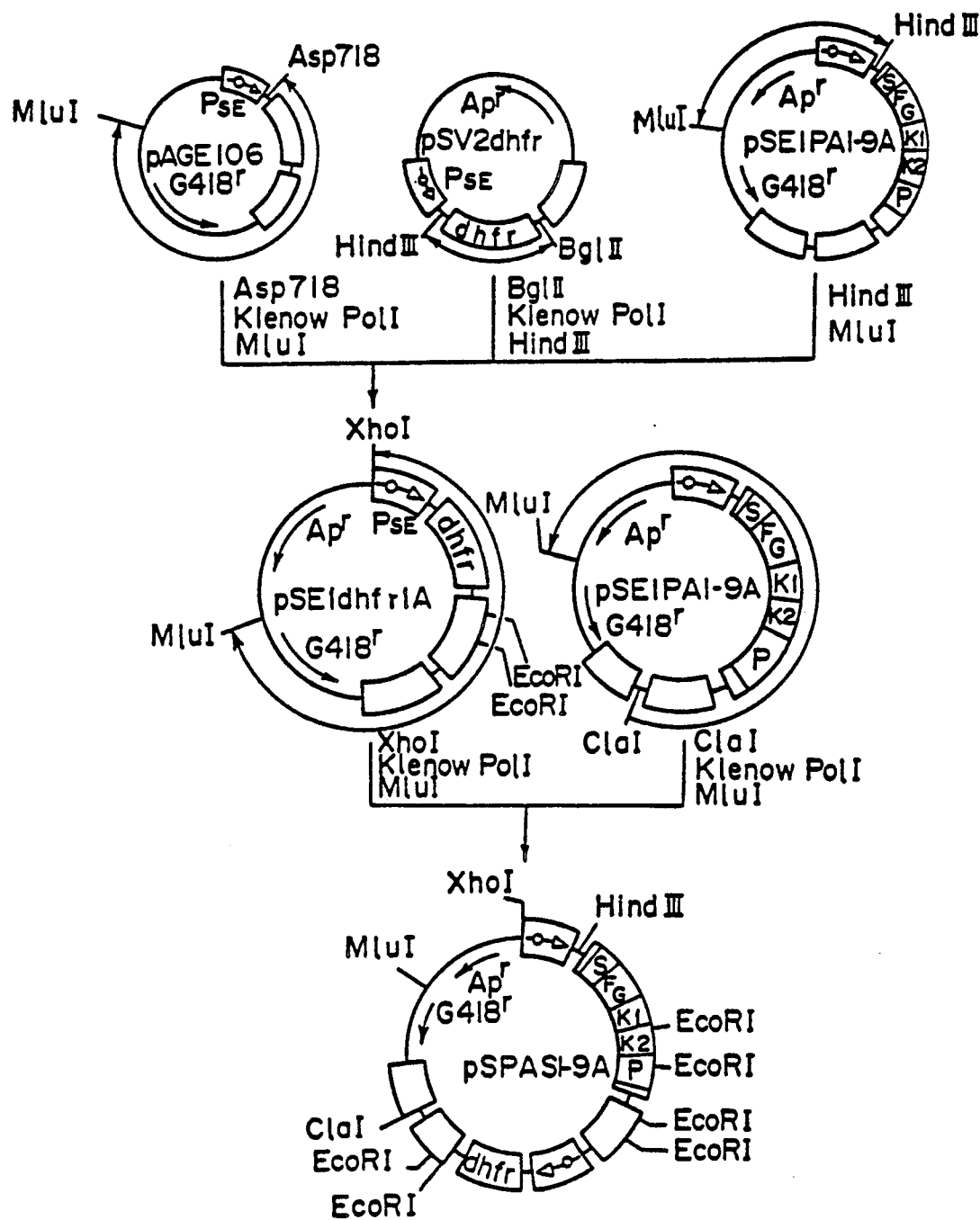

FIG. 37 illustrates the construction scheme for the plasmid pSPAS1-9A.

Figure 38:
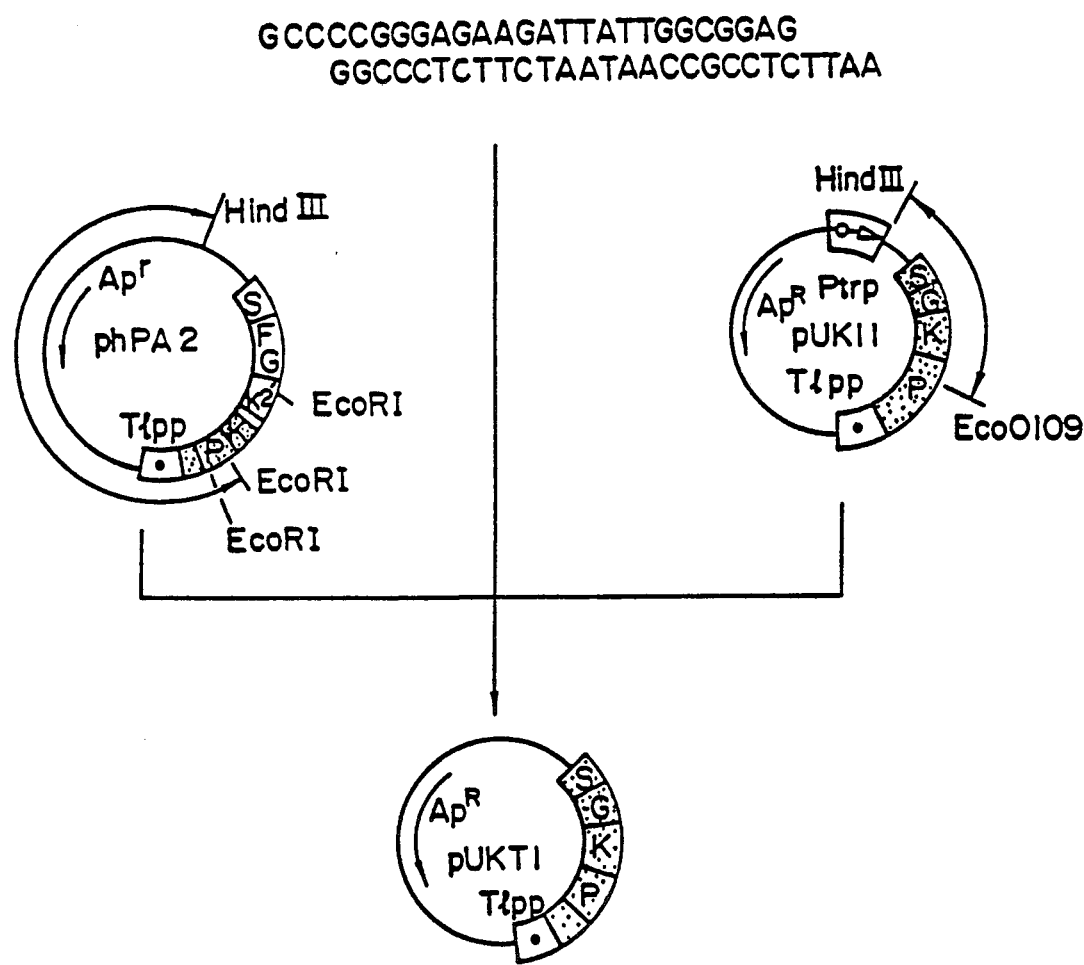

FIG. 38 illustrates the construction scheme for the plasmid pUKT1.

Figure 39:
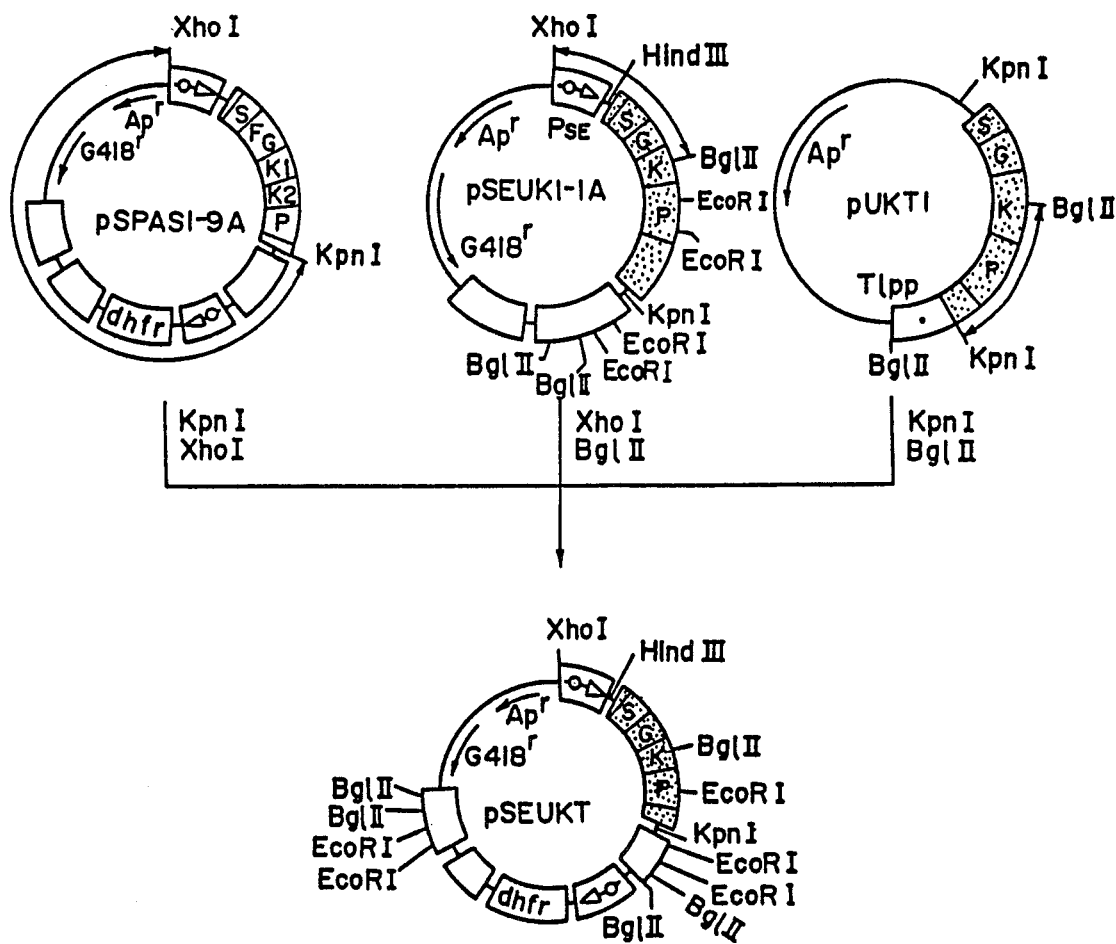

FIG. 39 illustrates the construction scheme for the plasmid pSEUKT.

FIG. 40 illustrates the DNA sequence for the pro-UK derivative UK-T6 and the amino acid sequences corresponding thereto.

FIG. 41 illustrates the DNA sequence for the pro-UK derivative UK-T3 and the amino acid sequence corresponding thereto.

FIG. 42 illustrates the DNA sequence for the pro-UK derivative UK-S3 and the amino acid sequence corresponding thereto.

FIG. (43-1 43-2) illustrates the DNA sequence for naturally occurring pro-UK and the amino acid sequence corresponding thereto.

In the figures mentioned above, the following abbreviations are used in the human t-PA cDNA region: F for finger domain, G for growth factor domain, K1 for kringle 1, K2 for kringle 2, K2' for kringle resulting from partial replacement of kringle 2 by kringle 1, and P for protease domain. In the human pro-UK cDNA region (dotted region), the following abbreviations are used: G for growth factor domain, K for kringle, and P for protease domain.

DETAILED DESCRIPTION OF THE INVENTION

The novel plasminogen activator according to the invention is a human prourokinase-type plasminogen activator resulting from substitution of an amino acid residue other than a proline residue for the 155th [from the N terminus, serine, of mature human prourokinase] amino acid residue, proline, of mature human prourokinase. This amino acid substitution results in an increase in plasminogen activator activity and in acquisition of resistance to thrombin-like proteases. While substitution of a threonine residue for the 155th amino acid, proline, residue is preferable, any amino acid residue selected from asparagine, aspartic acid, alanine, arginine, isoleucine, glycine, glutamine, glutamic acid, threonine, serine, cysteine, tyrosine, tryptophan, valine, histidine, phenylalanine, methionine, lysine and leucine can be used as a substitute provided that said residue can afford resistance to thrombin-like proteases.

It is also possible to increase the resistance to said proteases by replacing the 153rd amino acid (leucine) residue by some other amino acid residue simultaneously with the amino acid substitution in position 155. In this case, too, the plasminogen activator activity is not lowered.

A novel plasminogen activator resulting from substitution of an asparagine residue for the 153rd amino acid, leucine, residue and of a threonine residue for the 155th amino acid, proline, residue has a newly created site for N-glycosylation which can stabilize the protein. It is expected that when this plasminogen activator is expressed in animal cells, N-glycosylation might occur on the 153rd amino acid, asparagine, residue.

Hereinafter, the novel plasminogen activator according to the invention is referred to as "pro-UK derivative" for short.

The recombinant plasmid according to the invention is produced by insertion of a DNA fragment coding for the above-mentioned pro-UK derivative into an appropriate plasmid capable of DNA expression in host cells.

The DNA fragment, coding for the pro-UK derivative of this invention can be prepared by introducing a base substitution which causes amino acid substitution into a human UK DNA. As the human UK DNA, a cDNA obtained by reverse transcription of a messenger RNA coding for human UK and a human UK DNA obtained from chromosomal DNA are used.

The human UK cDNA may be any cDNA coding for human UK. Specifically, the human UK cDNA contained in the plasmid pUK1 or pUK11 can be used. pUK1 and pUK11 are plasmids produced by the present inventors and the procedures for their preparation are described in Reference Examples 1, 2 and 3.

The human UK cDNA in pUK1 codes for a pro-UK modification lacking part of the N-terminal region of pro-UK while that in pUK11 codes for a pro-UK modification lacking part of the C-terminal region of pro-UK. However, the base sequences of the respective cDNAs agree in part with the base sequence shown in Table 4.

An *Escherichia coli* strain harboring pUK1 and an *Escherichia coli* strain harboring pUK11 have been deposited, since Sep. 3, 1987, with the Fermentation Research Institute, Agency of Industrial Science and Technology of 1-3, Higashi 1-chome, Tsukuba-shi, Ibaraki 305, Japan under the names (and deposit numbers) of *Escherichia coli* EUK1 (FERM BP-1463) and *Escherichia coli* EUK11 (FERM BP-1464), respectively.

The plasmid into which the DNA coding for a pro-UK derivative is to be inserted may be any plasmid allowing expression of said DNA in microbial or animal cells. *Escherichia coli* is preferably used as the microbial cells. For causing expression of a pro-UK derivative in *Escherichia coli*, a plasmid which allows insertion of a foreign DNA thereinto at a site downstream from an appropriate promoter, for example trp or lac promoter and in which the distance between the Shine-Dalgarno sequence (hereinafter referred to as "SD sequence") and the initiation codon (ATG) is appropriate, for example 6 to 18 bases long, can be used. Specifically, pKYP10 (U.S. Pat. No. 4,686,191) and pTrS33 (Reference Example 4), both constructed by the present inventors, are preferred examples of such a plasmid.

The plasmid to be used in causing expression of the DNA coding for a pro-UK derivative in animal cells may be any plasmid provided that it allows expression of said DNA in animal cells. Preferred is a plasmid which allows insertion of a foreign DNA at a site downstream from an appropriate promotor, for example the SV40 early promoter or SV40 late promoter, and which contains a poly(A) signal, splicing signal and so forth.

Preferred plasmids are pAGE103 [Mizukami et al., J Biochem., 101, 1307–1310 (1987)] and pSE1PA1-SE1dhfr1-9A (hereinafter referred to as "pSPAS1-9A" for short) (Reference Example 14), both constructed by the present inventors.

An *Escherichia coli* strain harboring pAGE103 has been deposited, since Mar. 23, 1987, with the Fermentation Research Institute under the designation (and deposit number) *Escherichia coli* EAGE103 (FERM BP-1312). As a plasmid having the dihydrofolate reductase (hereinafter referred to as "dhfr") gene as a selective marker, there may be mentioned pSV2-dhfr [S. Subramani et al, Mol. Cell. Biol., 1, 854 (1981)], among others.

Recombination between the DNA coding for a pro-UK derivative and a vector DNA can be carried out by using available techniques that are generally used in the recombinant DNA technology, namely by digesting both DNAs with one or more restriction enzymes, followed by ligation using T4 DNA ligase. Prior to ligation, the termini of the DNA fragments obtained by digestion with the restriction enzyme or enzymes may be filled in using a DNA polymerase Klenow fragment or may be filled in or processed for paring off using T4 DNA polymerase. DNA linkers may also be used.

We now describe the construction of recombinant plasmids using pUK1 as the pro-UK cDNA-containing plasmid and incorporating respective DNAs coding for various pro-UK derivatives, if necessary by the intermediary of one or more chemically synthesized DNA fragments, and the construction of recombinant plasmids by incorporation of respective DNAs coding for various pro-UK derivatives into the vector pSPAS1-9A (Reference Example 14) for expression in animal cells as examples and for illustration purposes only.

In the first example that follows, the recombinant plasmid pUKT6 coding for a pro-UK derivative (UK-T6) is constructed.

Figure 1:
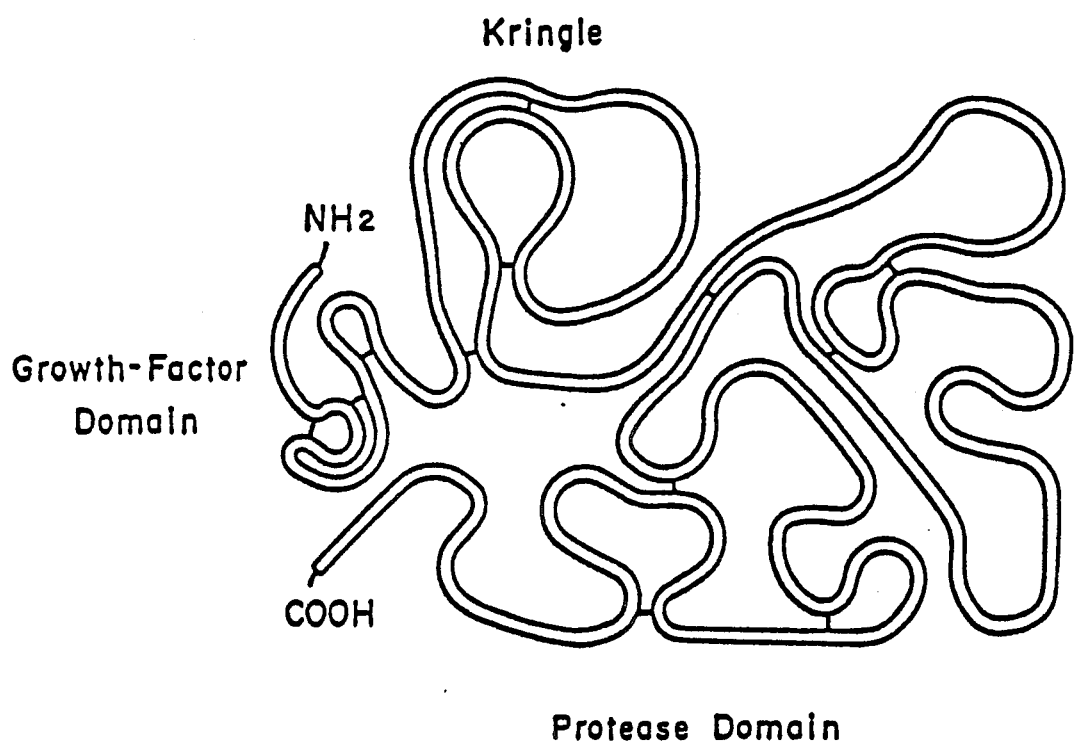
FIG. 1 illustrates the folded structure of human pro-UK.
Figure 2:
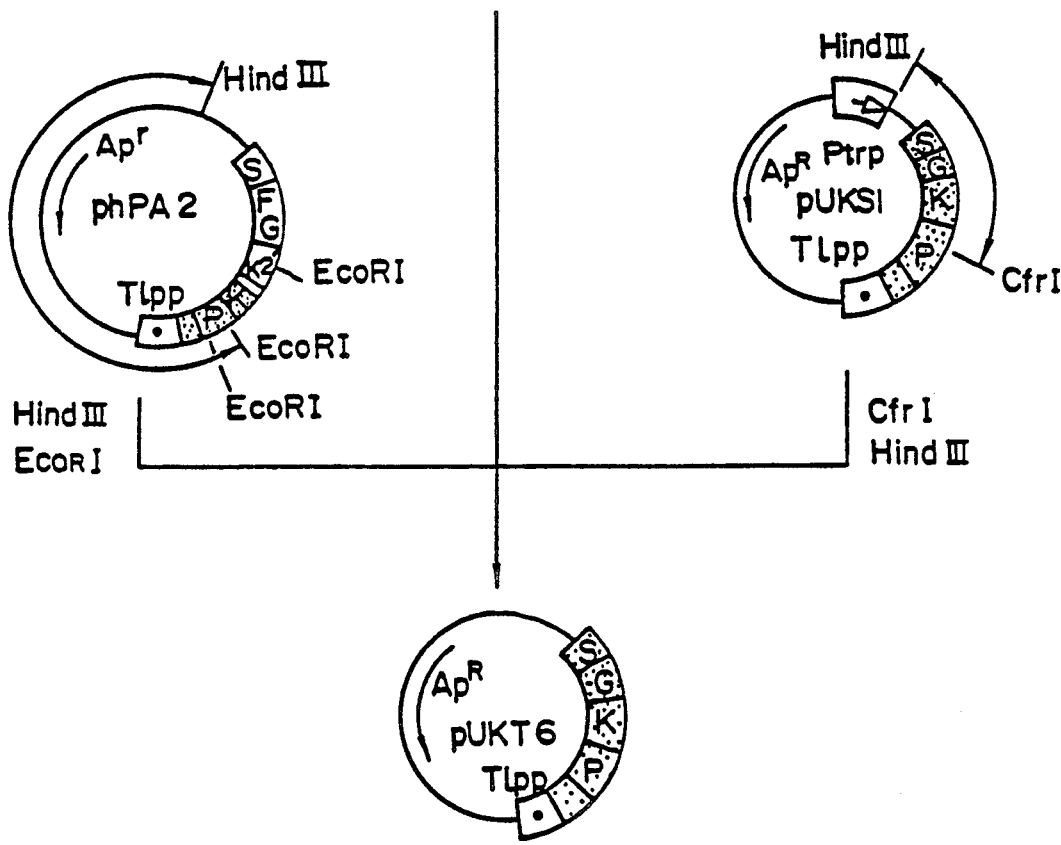
FIG. 2 illustrates the construction scheme for the plasmid pUKT6.

As shown in FIG. 2, phPA2 (Reference Example 10) constructed from pUK1 is cleaved with EcoRI and HindIII and a DNA fragment about 3.4 kb is purified. Separately, pUKS1 (Reference Example 11) is cleaved with HindIII and CfrI and DNA fragment about 0.75 kb is purified. The two DNA fragments thus obtained, together with the two 5'-phosphorylated synthetic DNAs shown in FIG. 2, are ligated together in the presence of T4 DNA ligase to give pUKT6 coding for a pro-UK derivative (UK-T6) differing from pro-UK in that the 155th (from the N terminus) amino acid residue Pro of pro-UK has been replaced by Thr.

In the next example that follows, the recombinant plasmid pUKT4 coding for a pro-UK derivative (UK-T4) and the recombinant plasmid pUKS3 coding for another pro-UK derivative (UK-S3) are constructed.

Figure 3:
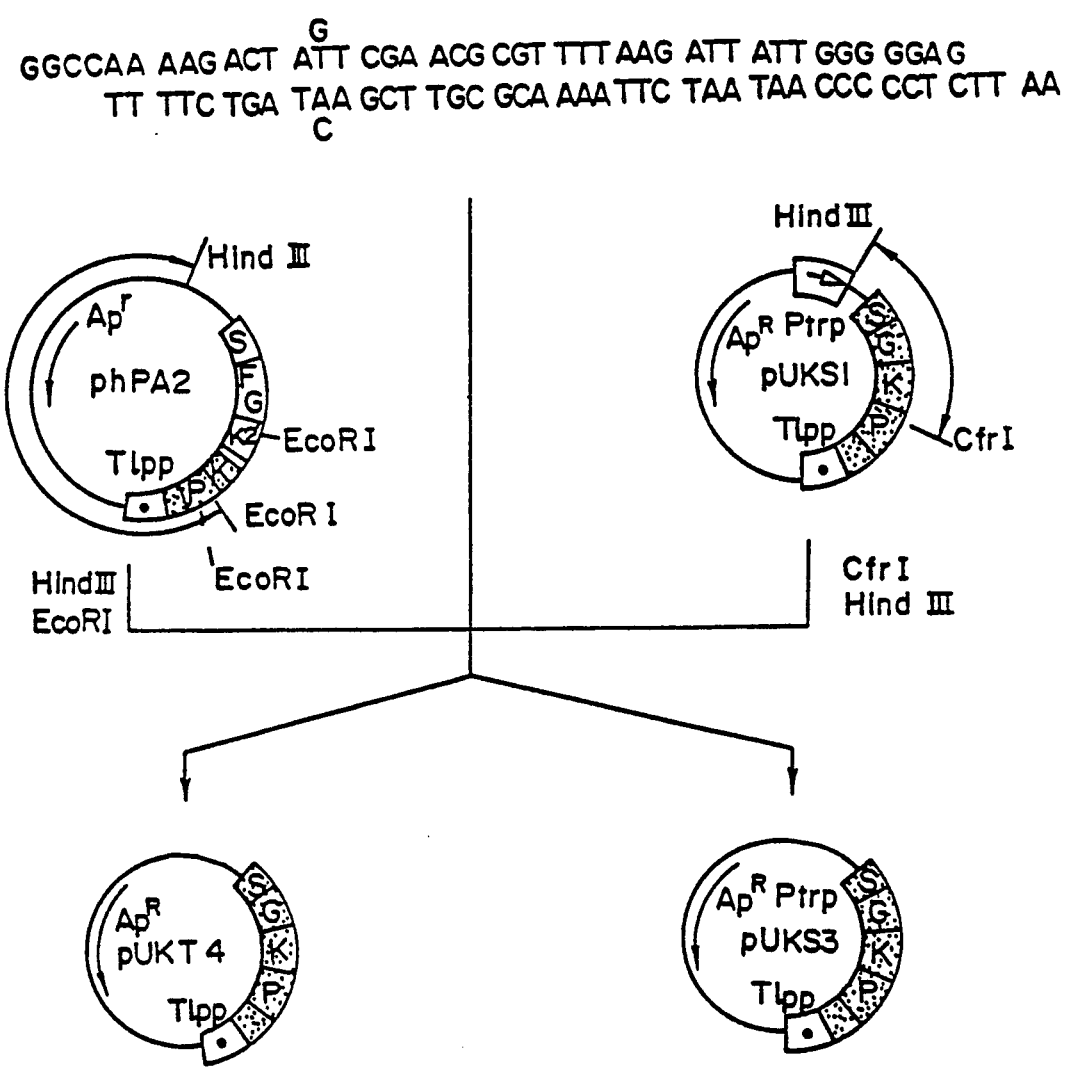
FIG. 3 illustrates the construction scheme for the plasmid pUKT4 and pUKS3.

As shown in FIG. 3, phPA2 (Reference Example 10) is cleaved with EcoRI and HindIII and a DNA fragment about 3.4 kb is purified. Separately, pUKS1 (Reference Example 11) is cleaved with HindIII and CfrI and a DNA fragment about 0.75 kb is purified. The two DNA fragments thus obtained, together with the two 5'-phosphorylated synthetic DNAs shown in FIG. 3, are ligated together in the presence of T4 DNA ligase to give pUKT4 coding for a pro-UK derivative (UK-T4) differing from pro-UK in that the 153rd (from the N terminus) amino acid residue Leu and 155th amino acid residue Pro of pro-UK have been replaced by Ser and Thr, respectively. pUKS3 coding for a pro-UK derivative (UK-S3) differing from pro-UK in that the 153rd (from the N terminus) amino acid residue Leu and 155th amino acid residue Pro of pro-UK have been replaced by Asn and Thr, respectively, is also obtained.

Plasmid DNAs capable of expressing the respective pro-UK derivatives (UK-T6, UK-T4, UK-S3 and UK-T) and natural-type pro-UK in animal cells can be prepared, for example, in the following manner.

Figure 4:
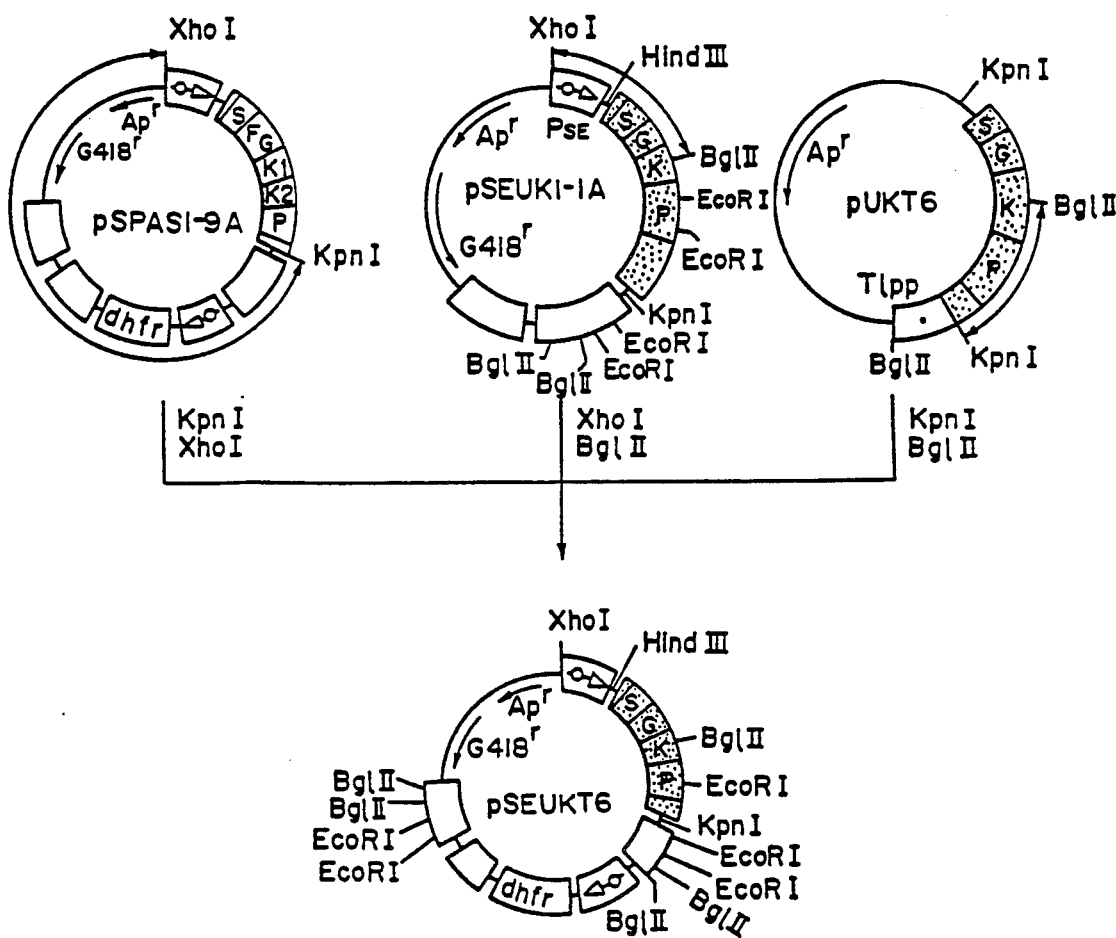
FIG. 4 illustrates the construction scheme for the plasmid pSEUKT6.

As shown in FIG. 4, pSPAS1-9A (Reference Example 14) is cleaved with XhoI and KpnI and a DNA fragment about 8.6 kb is purified. Separately, pSE1UK-pro1-1A (hereinafter referred to as pSEUK1-1A for short) (Reference Example 13) is cleaved with XhoI and BglII and a DNA fragment about 0.75 kb is purified. Further, separately, pUKT6 is cleaved with BglII and KpnI and a DNA fragment about 1.15 kb is purified. The three DNA fragments thus obtained are ligated together using T4 DNA ligase to give the plasmid pSE1UKT6SEd1-3 (hereinafter referred to as pSEUKT6 for short) capable of expressing a pro-UK derivative (UK-T6).

Figure 5:
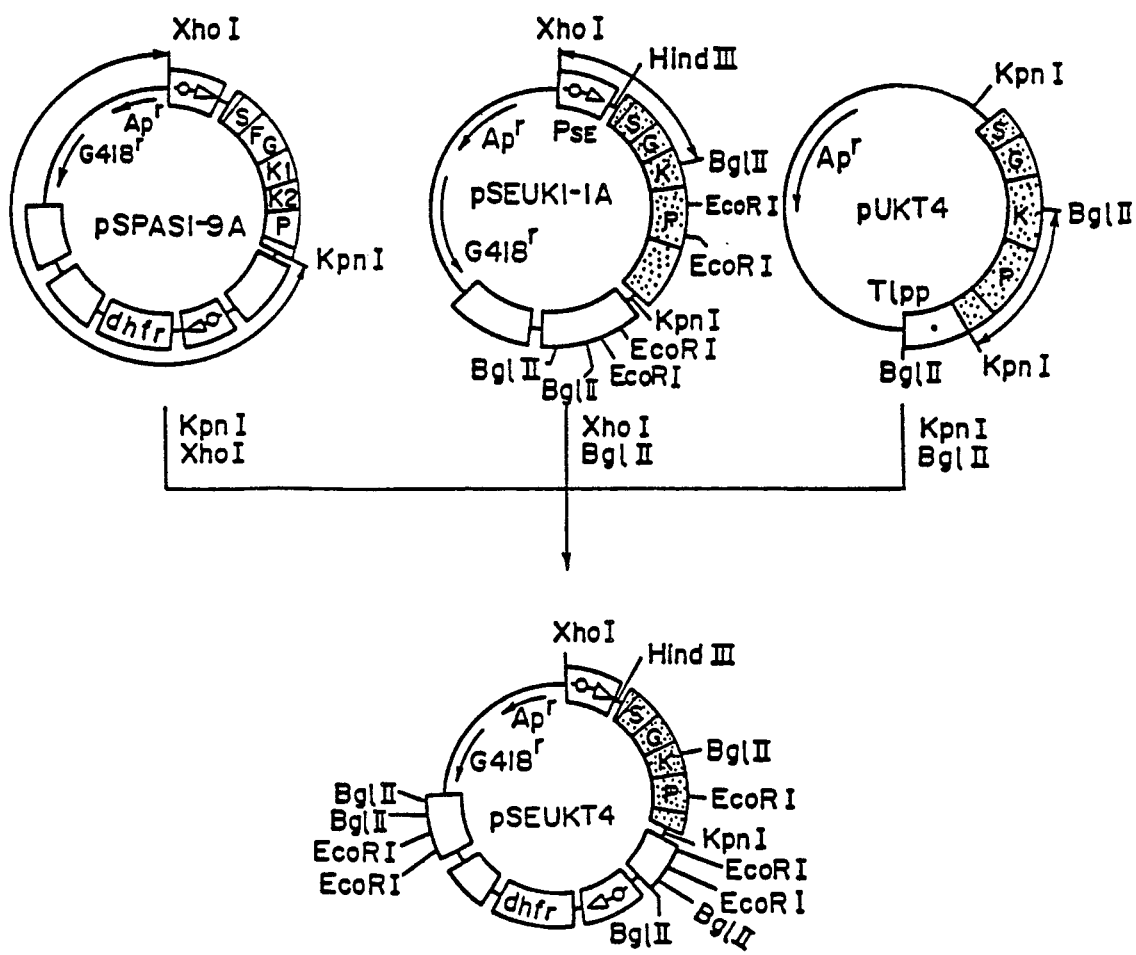
FIG. 5 illustrates the construction scheme for the plasmid pSEUKT4.

Then, as shown in FIG. 5, pSPAS1-9A (Reference Example 14) is cleaved with XhoI and KpnI and a DNA fragment about 8.6 kb is purified. Separately, pSEUK1-1A (Reference Example 13) is cleaved with XhoI and BglII and a DNA fragment about 0.75 kb is purified. Further, separately, pUKT4 is cleaved with BglII and KpnI and a DNA fragment about 1.15 kb is purified. The three DNA fragments thus obtained are ligated together using T4 DNA ligase to give the plasmid pSE1UKT4SEd1-3 (hereinafter referred to as pSEUKT4 for short) capable of expressing a pro-UK derivative (UK-T4).

Figure 6:
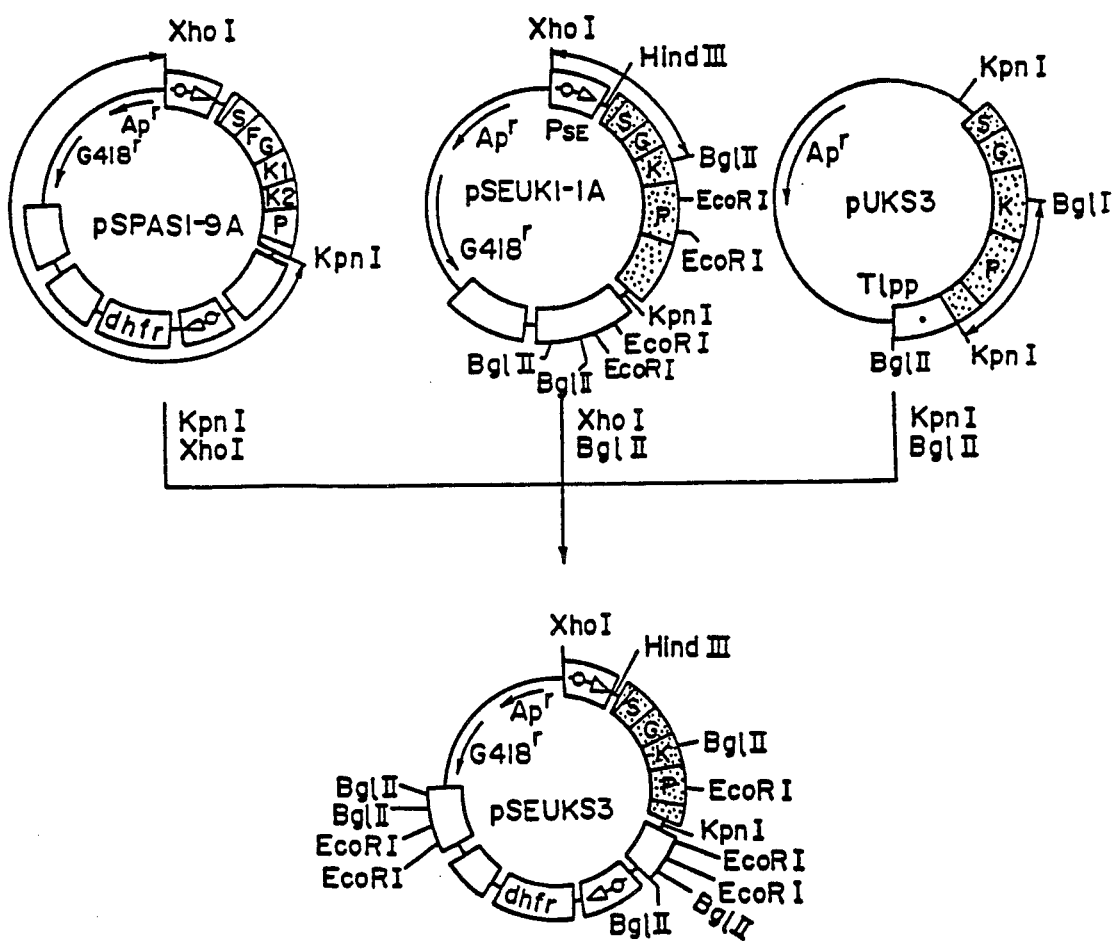
FIG. 6 illustrates the construction scheme for the plasmid pSEUKS3.

Then, as shown in FIG. 6, pSPAS1-9A (Reference Example 14) is cleaved with XhoI and KpnI and a DNA fragment about 8.6 kb is purified. Separately, pSEUK1-1A (Reference Example 13) is cleaved with XhoI and BglII and a DNA fragment about 0.75 kb is purified. Further, separately, pUKS3 is cleaved with BglII and KpnI and a DNA fragment about 1.15 kb is purified. The three DNA fragments thus obtained are ligated together in the presence of T4 DNA ligase to give the plasmid pSE1UK3SEd1-3 (hereinafter referred to as pSEUKS3 for short) capable of expressing a pro-UK derivative (UK-S3).

The DNA sequences for the pro-UK derivatives UK-T6, UK-T3 and UK-S3 and amino acid sequences corresponding thereto are shown in FIGS. 40, 41, and 42 respectively. The amino acid sequence of naturally occurring pro-UK and the corresponding DNA sequence are shown in FIG. 43.

The reaction conditions generally employed in the above recombination techniques are summarized as follows.

The digestion of DNA with a restriction enzyme or enzymes is generally carried out in a reaction mixture containing 0.1 to 20 μg of DNA, 2 to 200 mM (preferably 10 to 40 mM) Tris-HCl (pH 6.0 to 9.5, preferably pH 7.0 to 8.0), 0 to 200 mM NaCl and 2 to 20 mM (preferably 5 to 10 mM) MgCl$_2$, using 0.1 to 100 units (preferably 1 to 3 units per microgram of DNA) of each restriction enzyme, at 20° to 70° C. (the optimal temperature may vary depending on the restriction enzyme or enzymes) for 15 minutes to 24 hours. The reaction is generally terminated by heating at 55° to 75° C. for 5 to 30 minutes. The reaction may also be terminated by inactivating the restriction enzyme or enzymes using an appropriate reagent such as phenol or diethyl pyrocarbonate.

The DNA fragment resulting from resctriction enzyme digestion can be purified by low temperature gelation agarose gel electrophoresis (hereinafter referred to as "LGT method") [L. Wieslander, Analytical Biochemistry, 98, 305 (1979)] or agarose gel freezing and thawing (hereinafter referred to as "AFT method"). This AFT method comprises admixing a DNA fragment-containing agarose gel (0.7 to 1.5%) slice with an equal volume of TE buffer [10 mM Tris-HCl (pH 7.5), 1 mM EDTA] and 2 volumes of phenol (saturated with TE buffer), repeating two cycles of freezing (−70° C.) and thawing (65° C.), centrifuging, separating the resulting upper aqueous layer and recovering the DNA fragment by precipitation with ethanol. Alternatively, the DNA fragment may also be electrophoretically eluted and purified from an agarose or polyacrylamide gel using a Maxfield model AE-3241 DNA fragment collector (Atto), for instance. (Hereinafter, the latter method is referred to as "electrophoretic elution method").

The ligation of DNA fragments is generally carried out in a reaction mixture containing 2 to 200 mM (preferably 10 to 40 mM) Tris-HCl (pH 6.1 to 9.5, preferably pH 7.0 to 8.0), 2 to 20 mM (preferably 5 to 10 mM) MgCl$_2$, 0.1 to 10 mM (preferably 0.5 to 2.0 mM) ATP and 1 to 50 mM (preferably 5 to 10 mM) dithiothreitol (hereinafter referred to as "DTT") at 1 to 37° C. (preferably 3° to 20° C.) for 15 minutes to 72 hours (preferably 2 to 20 hours), using 1 to 1,000 units of T4 DNA ligase.

The recombinant plasmid DNA resulting from the ligation reaction is introduced into *Escherichia coli*, if necessary using the transformation method of Cohen et al. [S. N. Cohen et al., Proc. Natl. Acad. Sci. U.S.A., 69, 2110 (1972)] or the transformation method of Hanahan [J. Mol. Biol., 166, 557 (1983)].

The recombinant M13 phage RF DNA produced by the ligation reaction is introduced into *Escherichia coli*, strain JM105 [J. Messing et al., Gene, 33, 103 (1985)], for instance, if necessary using the known method of transfection [Y. Kuchino et al., Tampakushitsu, Kakusan, Koso (Protein, Nucleic Acid and Enzyme), 29, 294 (1984)].

The recombinant plasmid DNA or recombinant M13 phage RF DNA can be isolated from the *Escherichia coli*, strain harboring the same by the method of Birnboim et al. [H. C. Birnboim et al., Nucleic Acids Res., 7, 1513 (1979)], for instance.

The isolation of the single-stranded DNA from the recombinant M13 phage can be performed by the known method [Y. Kuchino et al., Tempakushitsu, Kakusan, Koso, 29, 294 (1984)].

The deoxyoligonucleotides to be used in the practice of the invention can be synthesized by solid-phase synthesis by the phosphoamidite method [S. L. Beaucage et al., Tetrahedron Lett., 22, 1859 (1981) and L. J. BcBrie et al., ibid. 24, 245 (1983)] using an Applied Biosystems model 380A DNA synthesizer (Applied Biosystems Inc., Foster City, Calif. 94404). For joining a deoxyoligonucleotide thus synthesized to another or other DNA fragments, about 20 picomoles of the deoxyoligonucleotide is 5'-phosphorylated in 20 μl of T4 kinase buffer [50 mM Tris-HCl (pH 7.6), 10 mM MgCl$_2$, 5 mM DTT, 0.1 mM EDTA, 0.5 mM ATP], with addition of 5 units of T4 DNA kinase. For use as a probe for hybridization, the deoxyoligonucleotide is radioactively labeled at the 5' end thereof using 20 to 50 µCi of 5'-[γ-32P]ATP (3,000 Ci/mmol, Amersham, Arlington Heights, Ill.) in lieu of 0.5 mM ATP in the T4 kinase buffer mentioned above.

For structural analysis of plasmid DNAs, each plasmid DNA is subjected to digestion with one to ten restriction enzymes, followed by agarose gel or polyacrylamide gel electrophoresis for checking the cleavage sites. Furthermore, if necessary, the base sequence of a DNA can be determined by the dideoxy sequence method using M13 phage.

The pro-UK derivative polypeptides according to the invention can be produced by using *Escherichia coli* or animal cells as the host, for example in the following manner.

The pro-UK derivative polypeptides are produced using animal cells as the host as follows. The host for use in causing expression of the pro-UK derivative polypeptides may be any animal cell strain or line provided that it allows expression of said polypeptides. Preferred specific animal cells include dhfr-deficient CHO cells [G. Urlaub & L. A. Chasin, Proc. Natl. Acad. Sci. U.S.A., 77, 4216 (1980)], among others.

In the following, an example of the pro-UK derivative polypeptide production is described in which pSEUKT6 is used as a plasmid for expression of the pro-UK derivative UK-T6 and dhfr-deficient CHO cells are used as the host.

The plasmid pSEUKT6 is introduced into dhfr-deficient CHO cells by, for example, the calcium phosphate method [Graham & Van der Eb, Virology, 52, 546 (1978)]. Transformant strains harboring pSEUKT6 can be selected using, for example, MEM ALPHA medium (ribonucleic acid-free and deoxyribonucleic acid-free; Gibco-Oriental) supplemented with G418 and dialyzed fetal calf serum. Furthermore, a transformant strain with the gene for the physiologically active polypeptide being amplified can be selected from the transformant resistant to methotrexate. The transformant strain thus obtained is cultured in a medium, whereby the pro-UK derivative polypeptide can be produced in the culture.

Suitable media are HAM F10 medium, HAM F12 medium (both available from Flow Laboratories), Dulbecco's MEM medium, RPMI-1640 medium (latter two available from Nissui Pharmaceutical), MEM ALPHA medium, and mixed media derived from these, each supplemented with any of various sera (e.g. fetal calf serum). If necessary, 0.5 to 5 mM glutamine, antibiotics [penicillin (25 U/ml), streptomycin (25 µg/ml), G418 (0.3 mg/ml), etc.], sodium bicarbonate (0.01%) and so forth may be added to the medium each in an appropriate amount.

For cultivation, various types of culture bottles, dishes, roller bottles, spinner flasks, jar fermenters and the like can be used. The cultivation is generally carried out at a seed cell density of $5 \times 10^4$ to $1 \times 10^6$ cells/ml at 30° to 40° C. for 2 to 10 days, whereupon the substance according to the invention is secreted mainly extracellularly in an amount depending on the cell density.

Cells are removed from the culture by centrifugation and the pro-UK derivative polypeptide is isolated and purified from the supernatant after centrifugation. The plasminogen activating activity of the pro-UK derivative polypeptide obtained can be assayed by the fibrin plate assay method [Granelli-Piperno & Reich, J. Exp. Med., 148, 223 (1978)].

While the production of UK-T6, one the novel pro-UK derivatives, has been described hereinabove in detail, other pro-UK derivatives can be produced substantially in the same manner following the descriptions and instructions given in this specification.

The following examples are further illustrative of the present invention, but are not intended to limit the scope of the invention.

EXAMPLE

Construction of the recombinant plasmid pUKT6 coding for the pro-UK derivative UK-T-6 (cf. FIG. 2)

About 2 µg of the pUKS1 plasmid DNA obtained in Reference Example 11 was dissolved in 30 µl of Y-100 buffer [solution containing 10 mM Tris-HCl (pH 7.5), 100 mM NaCl, 7 mM MgCl$_2$, 6 mM 2-mercaptoethanol], 16 units of CfrI (Takara Shuzo; hereinafter, unless otherwise specified, the restriction enzymes used were obtained from Takara Shuzo) and 10 units of HindIII were added, and the digestion reaction was performed at 37° C. for 2 hours. After 10 minutes of heat treatment at 65° C., a DNA fragment about 0.75 kb was purified using the AFT method. Separately, about 2 µg of the phPA2 plasmid DNA obtained in Reference Example 10 was dissolved in 30 µl of Y-100 buffer, 10 units of HindIII and 1 unit of EcoRI were added, and the digestion reaction was carried out at 37° C. for 2 hours. After 10 minutes of heat treatment at 65° C., a DNA fragment about 3.4 kb was purified using the AFT method. The following two synthetic DNAs (each having 43 bases) were synthesized using an Applied Bio-systems model 380A DNA synthesizer:

5'-GGCCAAAAGACCTTAAGGACGCGTTTTAAGATTATTGGAGGAG-3'
(43 bases)
3'-TTTTCTGGAATTCCTGCGCAAAATTCTAATAACCTCCTCTTAA-5'
(43 bases)

The thus-obtained synthetic DNAs (25 picomoles each) were then phosphorylated at the 5' end by treating in 10 µl of a solution (hereinafter referred to as "T4 kinase buffer") containing 50 mM Tris-HCl (pH 7.6), 10 mM MgCl$_2$, 5 mM DTT, 0.1 mM EDTA and 0.5 mM ATP, with 5 units of T4 DNA kinase (Takara Shuzo) added, at 37° C. for 30 minutes.

The thus-obtained pUKS1-derived DNA fragment (about 7.5 kb, about 0.1 µg), phPA2-derived DNA fragment (about 3.4 kb, about 0.1 µg) and two 5'-phosphorylated synthetic DNAs (1-picomole each) were dissolved in 20 µl of a buffer (hereinafter referred to as "T4 ligase buffer") containing 20 mM Tris-HCl (pH 7.6), 10 mM MgCl$_2$, 10 mM DTT and 1 mM ATP, 300 units of T4 ligase (Takara Shuzo) was added, and the ligation reaction was carried out at 4° C. for 18 hours. The resulting reaction mixture was used to transform *Escherichia coli* MM294 [F$^-$ hsdR$^-$ hsdM$^+$ endoI$^-$ thi] [ATCC31446; the same strain as *Escherichia coli* 294 so referred to in the report of K. Backman et al., Proc. Natl. Acad. Sci. U.S.A., 73, 4174 (1976)] to give ampicillin (hereinafter, "Ap")-resistant transformants. Plasmid DNAs were isolated from these transformants and subjected to structural analysis by digestion with restriction enzymes and the DNA sequence determination by the M13 dideoxy sequence method. A plasmid DNA thus found to have the desired structure was named pUKT6 (cf. FIG. 2).

EXAMPLE 2

Construction of the recombinant plasmid pUKT4 and pUKS3 coding for the pro-UK derivative UK-T4 and UK-S3, respectively (cf. FIG. 3)

About 2 μg of the pUKS1 plasmid DNA obtained in Reference Example 11 was dissolved in 30 μl of Y-100 buffer, 16 units of CfrI and 10 units of HindIII were added, and the digestion reaction was carried out at 37° C. for 2 hours. After 10 minutes of heat treatment at 65° C., a DNA fragment about 0.75 kb was purified using the AFT method. Separately, about 2 μg of the phPA2 plasmid DNA obtained in Reference Example 10 was dissolved in 30 μl of Y-100 buffer, 10 units of HindIII and 1 unit of EcoRI were added, and the digestion reaction was carried out at 37° C. for 2 hours. After 10 minutes of heat treatment at 65° C., a DNA fragment about 3.4 kb was purified using the AFT method. The following two synthetic DNAs (each having 43 bases) were synthesized and 5'-phosphorylated as described in Example 1.

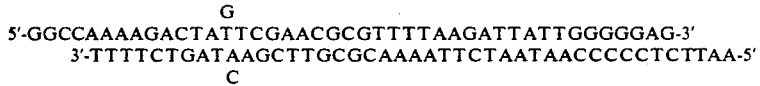

The thus-obtained pUKS1-derived DNA fragment (about 0.75 kb, about 0.1 μg), phPA2-derived DNA fragment (about 3.4 kb, about 0.1 μg) and two 5'-phosphorylated synthetic DNAs (1 picomole each) were dissolved in 20 μl of T4 ligase buffer, 300 units of T4 ligase was added, and the ligation reaction was carried out at 4° C. for 18 hours. The reaction mixture obtained was used to transform Escherichia coli MM294 to give Ap-resistant transformants. Plasmid DNAs were isolated from these transformants and subjected to structural analysis by digestion with restriction enzymes and to DNA sequence determination by the M13 dideoxy sequence method. A plasmid DNA having the desired structure and coding for an amino acid sequence modified in that the 153rd (from the N terminus) amino acid Leu and 155th amino acid Pro have been replaced by Ser and Thr, respectively, was named pUKT4 and another plasmid DNA also desirable in structure and coding for an amino acid sequence modified in that the 153rd (from the N terminus) amino acid Leu and 155th amino acid Pro have been replaced by Asn and Thr, respectively, was named pUKS3 (cf. FIG. 3)

EXAMPLE 3

Construction of the UK-T6 expression plasmid DNA pSEUKT6 (cf. FIG. 4)

About 2 μg of the pSPAS1-9A plasmid DNA obtained in Reference Example 14 was dissolved in 30 μl of Y-0 buffer [solution containing 10 mM Tris-HCl (pH 7.5), 7 mM MgCl₂ and 6 mM 2-mercaptoethanol], 10 units of KpnI were added, and the digestion reaction was carried out at 37° C. for 2 hours. Then, 1.5 μl of 2M NaCl and 10 units of XhoI were added and the digestion reaction was further carried out at 37° C. for 1 hour. After 10 minutes of heat treatment at 65° C., a DNA fragment about 8.6 kb was purified using the AFT method. Separately, about 3 μg of the pSEUK1-1A plasmid DNA was dissolved in 30 μl of Y-100 buffer, 12 units of BglII and 12 units of XhoI were added, and the digestion reaction was carried out at 37° C. for 2 hours. After 10 minutes of heat treatment at 65° C., a DNA fragment about 0.75 kb was purified using the AFT method. Further, separately, about 3 μg of the pUKT6 plasmid DNA obtained as described above was dissolved in 30 μl of Y-0 buffer, 15 units of KpnI was added, and the digestion reaction was carried out at 37° C. for 2 hours. Then, 1.5 μl of 2M NaCl and 12 units of BglII were added, and the digestion reaction was further conducted at 37° C. for 1 hour. After 10 minutes of heat treatment at 65° C., a DNA fragment about 1.15 kb was purified using the AFT method.

The thus-obtained pSPAS1-9A-derived DNA fragment (about 8.6 kb, about 0.1 μg), pSEUK1-1A-derived DNA fragment (about 0.75 kb, about 0.02 μg) and pUKT6-derived DNA fragment (about 1.15 kb, about 0.02 μg) were dissolved in 20 μl of T4 ligase buffer, 100 units of T4 DNA ligase was added, and the ligation reaction was carried out at 4° C. for 18 hours.

The reaction mixture thus obtained was used to transform Escherichia coli MM294 to give Ap-resistant transformants. The plasmid DNA pSEUKT6 isolated from one of said transformants was subjected to structural analysis by digestion with restriction enzymes and found to have the desired structure (cf. FIG. 4).

EXAMPLE 4

Construction of the UK-T4 expression plasmid DNA pSEUKT4 (cf. FIG. 5)

About 2 μg of the pSPAS1-9A plasmid DNA obtained in Reference Example 14 was dissolved in 30 μl of Y-0 buffer, 10 units of KpnI were added, and the digestion reaction was carried out at 37° C. for 2 hours. Then, 1.5 μl of 2M NaCl and 10 units of XhoI were added, and the digestion reaction was further conducted at 37° C. for 1 hour. After 10 minutes of heat treatment at 65° C., a DNA fragment about 8.6 kb was purified using the AFT method. Separately, about 3 μg of the pSEUK1-1A plasmid DNA was dissolved in 30 μl of Y-100 buffer, 12 units of BglII and 12 units of XhoI were added, and the digestion reaction was carried out at 37° C. for 2 hours. After 10 minutes of heat treatment at 65° C., a DNA fragment about 0.75 kb was purified using the AFT method. Further, separately, about 3 μg of the pUKT4 plasmid DNA obtained as described above was dissolved in 30 μl of Y-0 buffer, 15 units of KpnI was added, and the digestion reaction was carried out at 37° C. for 2 hours. Then, 1.5 μl of 2M NaCl and 12 units of BglII were added, and the digestion reaction was further conducted at 37° C. for 1 hour. After 10 minutes of heat treatment at 65° C., a DNA fragment about 1.15 kb was purified using the AFT method.

The thus-obtained pSPAS1-9A-derived DNA fragment (about 8.6 kb, about 0.1 μg), pSEUK1-1A-derived DNA fragment (about 0.75 kb, about 0.02 μg) and pUKT4-derived DNA fragment (about 1.15 kb, about 0.02 μg) were dissolved in 20 μl of T4 ligase buffer, 100 units of T4 DNA ligase was added, and the ligation reaction was carried out at 4° C. for 18 hours.

The reaction mixture thus obtained was used to transform *Escherichia coli* MM294 to give Ap-resistant transformants. The plasmid DNA pSEUKT4 isolated from one of these transformants was found to have the desired structure upon structural analysis by digestion with restriction enzymes (cf. FIG. 5).

EXAMPLE 5

Construction of the UK-S3 expression plasmid pSEUKS3 (cf. FIG. 6)

About 2 μg of the pSPAS1-9A plasmid DNA obtained in Reference Example 14 was dissolved in 30 μl of Y-0 buffer, 10 units of KpnI were added, and the digestion reaction was carried out at 37° C. for 2 hours. Then, 1.5 μl of 2M NaCl and 10 units of XhoI were added, and the digestion reaction was further conducted at 37° C. for 1 hour. After 10 minutes of heat treatment at 65° C., a DNA fragment about 8.6 kb was purified using the AFT method. Separately, about 3 μg of the pSEUK1-1A plasmid DNA was dissolved in 30 μl of Y-100 buffer, 12 units of BglII and 12 units of XhoI were added, and the digestion reaction was carried out at 37° C. for 2 hours. After 10 minutes of heat treatment at 65° C., a DNA fragment about 0.75 kb was purified using the AFT method. Further, separately, about 3 μg of the pUKS3 plasmid DNA obtained as described above was dissolved in 30 μl of Y-0 buffer, 15 units of KpnI was added, and the digestion reaction was carried out at 37° C. for 2 hours. Then, 1.5 μl of 2M NaCl and 12 units of BglII were added, and the digestion reaction was further carried out at 37° C. for 1 hour. After 10 minutes of heat treatment at 65° C., a DNA fragment about 1.15 kb was purified using the AFT method.

The thus-obtained pSPAS1-9A-derived DNA fragment (about 8.6 kb, about 0.1 μg), pSEUK1-1A-derived DNA fragment (about 0.75 kb, about 0.02 μg) and pUKS1-derived DNA fragment (about 1.15 kb, about 0.02 μg) were dissolved in 20 μl of T4 ligase buffer, 100 units of T4 DNA ligase was added, and the ligation reaction was carried out at 4° C. for 18 hours.

The reaction mixture thus obtained was used to transform *Escherichia coli* MM294 to give Ap-resistant transformants. The plasmid DNA pSEUKS3 isolated from one of these transformants was found to have the desired structure upon structural analysis by digestion with restriction enzymes (cf. FIG. 6).

EXAMPLE 6

Production of various pro-UK derivatives and natural pro-UK in animal cells (1) Production of the UK-T6 polypeptide in CHO cells carrying pSEUKT6 pSEUKT6 (obtained in Example 3) was introduced into dhfr-deficient CHO cells essentially by the calcium phosphate method. Thus, 5 ml of MEM α (non-selective medium) supplemented with 1/10 volume of FCS (fetal calf serum) and 1/50 volume of 7.5% NaHCO₃ (Flow Laboratories) was inoculated with CHO cells to a cell concentration of $1 \times 10^5$ cells/ml [LUX dishes 6 cm in diameter were used for culturing (LUX dishes were used also in the subsequent examples)] and the cells were cultured in a CO₂ incubator at 37° C. for 1 day. Separately, 10 μg of the pSEUKT6 DNA was dissolved in 450 μl of 10 mM Tris-HCl (pH 7.5), and 500 μl of a solution containing 280 mM NaCl, 1.5 mM Na₂HPO₄ and 50 mM HEPES (N-2-hydroxyethylpiperazine-N'-2-ethanesulfonic acid) (pH 7.1) was added to the solution. After mixing, 50 μl of 2.5M CaCl₂ was further added and, after mixing, the resulting mixture was allowed to stand at room temperature for 5 minutes. The whole quantity of this DNA solution was added to a dhfr-deficient CHO cell culture prepared by discarding the medium, adding 10 ml of fresh MEM α (nonselective medium) and culturing for 1 hour. The resulting mixture was incubated for 8 hours. Then, cells were washed with PBS (phosphate buffer-saline; 8 g/liter NaCl, 0.2 g/liter KCl, 1.15 g/liter Na₂HPO₄ (anhydrous), 0.2 g/liter KH₂PO₄) and, after addition of 5 ml of MEM α (nonselective medium), cultured for 16 hours. Cells were washed with PBS, 3 ml of a solution containing 0.05% trypsin and 0.2% EDTA (ethylenediaminetetraacetic acid) was added thereto, the excess solution was removed, and incubation was conducted at 37° C. for 5 minutes (trypsin treatment). MEM α (selective medium) supplemented with 10% dialyzed FCS (Gibco-Oriental), 1/50 volume of 7.5% NaHCO₃, 1/100 volume of 100×nonessential amino acid solution and 0.3 mg/ml G418 (Gibco-Oriental) was added to the cells for thoroughly suspending the cells therein. Incubation was performed in a CO₂ incubator at 37° C. for 5 days using a dish having a diameter of 10 cm. Cells were washed with PBS and, after addition of MEM α (selective medium), cultured for 5 days. After the same procedure as above was followed, incubation was further carried out for 5 days. Cells were washed with PBS, subjected to trysin treatment, suspended in 10 ml of MEM α (selective medium) and cultured in a dish having a diameter of 6 cm in a CO₂ incubator at 37° C. for 3 to 7 days. Colonies that had appeared were subjected to trypsin treatment and then inoculated into a dish having a diameter of 10 cm to a cell concentration of $5 \times 10^4$ cells/ml using 10 ml of MEM α (selective medium) containing 50 mM MTX. Medium exchange was performed three times at 5 day intervals using the same medium mentioned above. MTX-resistant colonies that had appeared were respectively isolated and each colony was cultured in a dish having a diameter of 6 cm until confluence. Then, the medium was replaced with 5 ml of MEM α (selective medium) containing 50 nM MTX and, after 1 day, the culture supernatant was examined for the activity of UK-T6 by the fibrin plate assay method [Granelli-Piperno & Reich, J. Exp. Med., 148, 233 (1978)]. With the clone No. 24, the highest activity was detected and the production of UK-T6 amounted to 5 μg/10⁶ cells/day. This clone was cultured in 100 ml of MEM α (selective medium) containing 50 nM MTX in a Falcon model 3027 roller bottle. After confluence, culture was conducted for 3 days in a medium identical in composition to the above-mentioned one except that it was FCS-free and contained 10 KIU/ml of aprotinin (Boehringer-Mannheim). The culture supernatant (100 ml per run) thus obtained was used in Example 7.

(2) Production of the UK-T4 polypeptide in animal cells carrying pSEUKT4

Using the recombinant plasmid pSEUKT4 obtained in Example 4 and dhfr-deficient CHO cells and following the same procedure as described above, there were obtained UK-T4-producing cell strains. Among them, the clone No. 8 was found to be the highest in activity, the UK-T4 production amounting to 3 μg/10⁶ cells/day. This clone was cultured in 100 ml of MEM α (selective medium) containing 50 nM MTX in a Falcon model 3027 roller bottle. After confluence, culture was conducted for 3 days in a medium identical in composition to the above-mentioned one except that it was FCS-free and contained 10 KIU/ml of aprotinin (Boehringer-Mannheim). The culture supernatant (100 ml per run) thus obtained was used in Example 7.

(3) Production of the UK-S3 polypeptide in animal cells carrying pSEUKS3

Using the recombinant plasmid pSEUKS3 obtained in Example 5 and dhfr-deficient CHO cells and following the same procedure as described above, there were obtained UK-S3-producing cell strains. Among them, the clone No. 13 was found to be the highest in activity, the UK-S3 production amounting to 3 $\mu g/10^6$ cells/day. This clone was cultured in 100 ml of MEM $\alpha$ (selective medium) containing 50 nM MTX in a Falcon model 3027 roller bottle. After confluence, culture was conducted for 3 days in a medium identical in composition to the above-mentioned one except that it was FCS-free and contained 10 KIU/ml of aprotinin (Boehringer-Mannheim). The culture supernatant (100 ml per run) thus obtained was used in Example 7.

(4) Production of the pro-UK polypeptide in animal cells carrying pSE1UKT1-1d (hereinafter referred to as "pSEUKT")

Using the recombinant plasmid pSEUKT obtained in Reference Example 16 and dhfr-deficient CHO cells and following the same procedure as described above, there were obtained UK-T-producing cell strains. Among them, the clone No. 21 was found to be the highest in activity, the UK-T4 production amounting to 3 $\mu g/10^6$ cells/day. This clone was cultured in 100 ml of MEM $\alpha$ (selective medium) containing 50 nM MTX in a Falcon model 3027 roller bottle. After confluence, culture was conducted for 3 days in a medium identical in composition to the above-mentioned one except that it was FCS-free and contained 10 KIU/ml of aprotinin (Boehringer-Mannheim). The culture supernatant (100 ml per run) thus obtained was used in Example 7.

(5) Production of the pro-UK polypeptide in animal cells carrying pSEUK1-1A

Using the recombinant plasmid pSEUK1-1A obtained in Reference Example 13 and pSV2-dhfr and dhfr-deficient CHO cells and following the same procedure as described above, there were obtained pro-UK-producing cell strains. Among them, the clone No. 5 was found to be the highest in activity, the pro-UK production amounting to 3 $\mu g/10^6$ cells/day. This clone was cultured in 100 ml of MEM $\alpha$ (selective medium) containing 50 nM MTX in a Falcon model 3027 roller bottle. After confluence, culture was conducted for 3 days in a medium identical in composition to the above-mentioned one except that it was FCS-free and contained 10 KIU/ml of aprotinin (Boehringer-Mannheim). The culture supernatant (100 ml per run) thus obtained was used in Example 7.

EXAMPLE 7

Purification of natural type pro-UK and various pro-UK derivatives from animal cell culture supernatants The serum-free culture supernatants (200 ml each) obtained in Example 6 and containing natural type pro-UK or a pro-UK derivative were respectively applied to an anti-UK monoclonal antibody column (4 ml) [prepared by binding an anti-UK monoclonal antibody (prepared by the method of Milstein et al. [C. Milstein et al., Nature, 256, 495–497 (1975)] using low-molecular uro-kinase (Nippon Chemical Research) as an antigen] to CNBr4-activated Sepharose 4B (Pharmacia Fine Chemicals)] equilibrated with 50 mM phosphate buffer (pH 7.5) containing 0.01% Tween 80, 0.05% NaN$_3$ and 100 mM NaCl. Then, 3 bed volumes of the same buffer as used for column equilibration was applied to the column. Elution was then performed using 16 ml of phosphate-citrate buffer (pH 4.0) containing 0.01% Tween 80, 0.05% NaN$_3$, 100 mM NaCl and 200 mM arginine and the eluate was fractionated in 1 ml portions. The active eluate fractions were immediately adjusted to pH 7.5 with phosphoric acid and then dialyzed against phosphate buffer (pH 7.5) containing 0.01% Tween 80, 0.05% NaN$_3$, 100 mM NaCl and 200 mM arginine (hereinafter referred to as "UK buffer") at 4° C. for 24 hours. The dialyzate was used as a final purified sample in the subsequent experiments. SDS-polyacrylamide gel electrophoresis revealed that the final purified sample contained a single-chain product with a purity of not less than 95%. The SDS-polyacrylamide gel electrophoresis suggested carbohydrate chain addition to the pro-UK derivative UK-S3, which has an N-glycosylation site, namely -Asn-X-Thr-. An increase in molecular weight was confirmed as well.

EXAMPLE 8

Comparison in specific activity between the natural type pro-UK and pro-UK derivatives The final purified samples respectively containing the natural type pro-UK and pro-UK derivatives as obtained in Example 7 were each applied to a reversed-phase HPLC column (TSK gel ODS-120T, Tosoh). The peak area was compared with the peak area for natural type pro-UK for which the concentration had been determined by the Lowry method [Lowry et al., J. Biol. Chem., 193, 265 (1951)] to determine the concentration of each protein. The activity of each sample was determined by the fibrin plate assay method.

The fibrin plate assay method was carried out in the following manner.

Bovine thrombin (Sigma) (1,000 U) was dissolved in 5 ml of 50 mM phosphate buffer (pH 7.0). The solution was filter sterilized through a 0.45 $\mu$m membrane filter to give a thrombin solution. Separately, a fibrinogen solution was prepared by dissolving bovine fibrinogen (Nakalai-Tesque) in 100 ml of sterilized 50 mM phosphate buffer (pH 7.0) with 30 minutes of stirring and then removing the insoluble matter using sterilized glass wool to give a fibrinogen solution. Furthermore, a 2% agar solution was prepared by adding 2 g of agar (Sigma) to 100 ml of 50 mM phosphate buffer (pH 7.0), sterilizing at 1.5 atmospheres and 120° C. for 20 minutes and then maintaining the solution at 60° C.

In each dish, there were placed 0.25 ml of the thrombin solution, 5 ml of the fibrinogen solution and 5 ml of the agar solution. The mixture was stirred and then allowed to stand for solidification of agar. A fibrin plate was thus obtained.

Human urokinase (double-chain form, urine-derived, Nippon Chemical Research) was dissolved in UK buffer and the concentration was adjusted to 10, 100, 1,000 and 10,000 IU/ml. These solutions were used as standards. Each sample was diluted to 0.5 $\mu$g/ml with UK buffer.

Holes having a diameter of 2 mm were made on each fibrin plate, the number of the holes being the same as the number of the standards and samples. The holes were filled with 5 μl each of the standards or samples prepared as described above. After 24 hours of incubation at 37° C., the diameter of each resultant halo was measured. The activity of each samples was determined using a calibration curve (activity: halo diameter) prepared by using the standards.

The specific activity data for the natural type pro-UK and respective pro-UK derivatives are shown herein below in Table 1. While the specific activities of UK-T6, UK-T4 and UK-S3 were higher (1,2- to 1,8-fold) than that of natural type pro-UK, the specific activity of the pro-UK derivative UK-T (with an amino acid substitution in position $P_1'$ relative to the thrombin cleavage site) was only 60% of that of natural type pro-UK. This decrease in specific activity was presumably due to that introduction of amino acid substitution in the neighborhood of the plasmin cleavage site (namely in position $P_2$ relative to the plasmin cleavage site) which made it difficult for the cleavage with plasmin to take place. Therefore, the pro-UK derivatives (UK-T6, UK-T4 and UK-S3) with amino acid substitution in position $P_2$ are advantageous from the specific activity viewpoint as well.

EXAMPLE 9

Comparison in susceptibility to thrombin between the natural type pro-UK and pro-UK derivatives The final purified samples respectively containing the natural type pro-UK and pro-UK derivatives as obtained in Example 7 were each applied to a reversed-phase HPLC column (TSK gel ODS-120, Tosoh). Each sample was diluted with the diffusate solution (obtained in the dialysis in Example 7) to 30 μg/ml on the basis of the peak area obtained. To 100 μl of this dilution was added 20 μl of 30 IU/ml or 600 IU/ml human thrombin, and the mixture was incubated at 37° C. The human thrombin was obtained from Sigma. The human thrombin was used after 1.5 hours of treatment with 10 IU/1,000 IU thrombin of aprotinin at 37° C. Fifteen (15), 30, 60, 120 and 240 minutes after addition of thrombin, sampling was made in 24 μl portions, followed by addition of 4 μl of 84 μM thrombin inhibitor (THROM-STOP, American Diagnostica) for termination of the reaction. A sample was also prepared by adding the thrombin inhibitor immediately after addition of thrombin. This sample was used as the 0 minute-sample. Furthermore, in a control group, samples without addition of thrombin were incubated at 37° C.

A comparison with respect to the susceptibility to thrombin was performed by determining the residual activities of the natural type pro-UK and pro-UK derivatives in the reaction mixtures obtained as described above by the fibrin plate assay method (cf. Example 8). As a result, it was revealed that the pro-UK derivatives had apparently decreased susceptibility to thrombin as compared with natural type pro-UK (cf. FIG. 7-(1)). In particular, it was also shown that UK-T6, UK-T4 and UK-S3 were still lower in susceptibility to thrombin than UK-T (cf. FIG. 7-(2)).

TABLE 1

| Sample | Specific activity ($\times 10^4$ IU/mg) |
| --- | --- |
| Natural type pro-UK | 12.8 ± 0.92  100 |
| UK-T6 | 15.4 ± 0.87  120 |
| UK-T4 | 16.2 ± 1.26  127 |
| UK-S3 | 22.7 ± 0.90  177 |
| UK-T | 7.8 ± 0.74  61 |

For further confirmation of the above results, 10 μl each of the above reaction mixtures was subjected to SDS-polyacrylamide gel electrophoresis [Laemmli, Nature, 227, 680 (1970)]. While natural type pro-UK was cleaved with thrombin by degrees, the pro-UK derivatives were hardly cleaved with thrombin (cf. FIG. 7-(3)). These results indicated, in good agreement with the results of fibrin plate assay, that the pro-UK derivatives had decreased susceptibility to thrombin.

Strains of *Escherichia coli* harboring the plasmids pSEUKS3, pSEUKT4 and pSEUKT6 have been deposited, since Jun. 15, 1989, with the Fermentation Research Institute under the Budapest Treaty under the designations (and accession numbers) *Escherichia coli* ESEUKS3 (FERM BP-2478), *Escherichia coli* ESEUKT4 (FERM BP-2479) and *Escherichia coli* ESEUKT6 (FERM BP-2480), respectively.

The reference examples referred to in the above examples are given below.

REFERENCE EXAMPLE 1

Construction of the plasmid ptPA7 carrying human t-PA cDNA (1) Preparation of poly(A) RNA from Detroit 562 cells RNA was prepared from Detroit 562 human pharyngeal carcinoma cells by the guanidine thiocyanate-lithium chloride method [Cathala et al., DNA, 2, 329 (1983)] as follows.

Detroit 562 human pharyngeal carcinoma cells [W. D. Peterson, Jr, et al., Proc. Soc. Exp. Biol. Med., 36, 1187 (1971)] were grown in 50 ml MEM medium (Nissui Pharmaceutical) containing 10% FCS, 1/100 volume of 100 ×nonessential amino acid solution (Flow Laboratories), 1 mM sodium pyruvate and 0.1% lactoalbumin hydrolyzate (Gibco-Oriental) in a tissue culture flask (Corning; 150 cm$^2$). After cultivation at 37° C. until confluence, cells were washed with PBS, 100 ng/ml of phorbol myristate acetate (PMA) was added and, after addition of 30 ml of the same medium as mentioned above except that it was FCS-free, incubation was performed at 37° C. for 24 hours. Then, cells were treated with 10 ml of a solution containing 0.05% trypsin and 0.02% EDTA to give a cell suspension. Six tissue culture flasks of the above type were used to give a total of 1×10$^8$ cells. Cells were collected from the pooled cell suspension by centrifugation (1,100×g, 4° C., 10 minutes), washed with 80 ml of phosphate buffer, and solubilized in 10 ml of a solution containing 5M guanidine thiocyanate, 10 mM EDTA, 50 mM Tris-HCl (pH 7) and 8% (v/v) 2-mercaptoethanol using a vortex mixer. The solubilization product was transferred to a centrifuge tube, 80 m of 4M LiCl was added and, after stirring, the resulting mixture was allowed to stand at 4° C. for 20 hours. Centrifugation using a Hitachi RPR10 rotor (9,000 rpm, 90 minutes) resulted in recovery of RNA as a precipitate. The RNA precipitate was suspended in 50 ml of a solution comprising 4M urea and 2M lithium chloride, and RNA was recovered again as a precipitate by centrifugation using a Hitachi RPR10 rotor (9,000 rpm, 60 minutes). The RNA precipitate was dissolved in 10 ml of a solution containing 0.1% sodium lauryl sulfate, 1 mM EDTA and 10 mM Tris-HCl (pH 7.5) and, after extraction with phenol-chloroform, recovered by precipitation with ethanol. About 2.5 mg of the RNA obtained was dissolved in 1 ml of a solution containing 10 mM Tris-HCl (pH 8.0) and 1 mM EDTA. After 5 minutes of incubation at 65° C., 0.1 ml of 5M NaCl was added. The resulting mixture was subjected to oligo(dT)-cellulose column [P-L Biochemicals) chromatography (column volume: 0.5 ml). The poly(A)-containing mRNA adsorbed was eluted with a solution containing 10 mM Tris-HCl (pH 7.5) and 1 mM EDTA. About 90 μg of poly(A)-containing mRNA was thus obtained.

(2) Synthesis of cDNA and insertion of said DNA into a vector

Synthesis of cDNA and construction of a recombinant plasmid with the cDNA inserted therein were performed by the Okayama-Berg method [Mol. Cell. Biol., 2, 161 (1982)]. The processes are schematically illustrated in FIG. 8.

400 μg of pCDV1 [Okayama & Berg, Mol. Cell. Biol., 3, 280 (1983)] was added to 300 μl of a solution containing 10 mM Tris-HCl (pH 7.5), 6 mM $MgCl_2$ and 10 mM NaCl, 500 units of KpnI was added, and the reaction was carried out at 37° C. for 6 hours for the cleavage of the plasmid at the KpnI site occurring therein. After extraction with phenol-chloroform, DNA was recovered by precipitation with ethanol. About 200 μg of the KpnI-cleaved DNA was added to 200 μl of a buffer containing 40 mM sodium cacodylate, 30 mM Tris-HCl (pH 6.8), 1 mM $CaCl_2$ and 0.1 mM dithiothreitol (DTT) (hereinafter referred to as "TdT buffer") with dTTP added to a concentration of 0.25 mM. Furthermore, 81 units of terminal deoxynucleotidyl transferase (hereinafter referred to as "TdT") (P-L Biochemicals) was added, and the reaction was carried out at 37° C. for 11 minutes, whereupon a poly(dT) chain comprising about 67 dT residues was added to the 3′ terminus of the KpnI cleavage site of pCDV1. After phenol-chloroform extraction, about 100 μg of the poly(dT) chain-containing pCDV1 DNA recovered from the solution by precipitation with ethanol. The DNA thus obtained was added to 150 μl of a buffer containing 10 mM Tris-HCl (pH 7.5), 6 mM $MgCl_2$ and 100 mM NaCl, 360 units of EcoRI was further added, and the reaction was carried out at 37° C. for 2 hours. The reaction mixture was treated by the LGT method and a DNA fragment about 3.1 kb was recovered. About 60 μg of poly(dT) chain-added pCDV1 was obtained. The resulting DNA was dissolved in 500 μl of a solution containing 10 mM Tris-HCl (pH 8.0) and 1 mM EDTA, the solution was incubated at 65° C. for 5 minutes and then cooled on ice, and 50 μl of 5M NaCl was added to the solution. The resultant mixture was subjected to oligo(dA)-cellulose column (Collaborative Research) chromatography. Molecules having a sufficiently long poly(dT) chain were adsorbed on the column. They were eluted with a solution containing 10 mM Tris-HCl (pH 8.0) and 1 mM EDTA to give 27 μg of poly(dT) chain-added pCDV1 (hereinafter referred to as "vector primer").

A linker DNA was prepared in the following manner.

About 14 μg of pL1 [Okayama & Berg, Mol. Cell. Biol., 3, 280 (1983)] was added to 200 μl of a buffer containing 10 mM Tris-HCl (pH 7.5), 6 mM $MgCl_2$ and 50 mM NaCl, 50 units of PstI was added, and the reaction was carried out at 37° C. for 4 hours for the cleavage of the pL1 DNA at the PstI site occurring therein. The reaction mixture was subjected to phenol-chloroform extraction and then about 13 μg of the PstI-cleaved pL1 DNA was recovered by precipitation with ethanol. About 13 μg of the thus-obtained DNA was added to 50 μl of a solution prepared by adding dGTP to TdT buffer to a final concentration of 0.25 mM, 54 units of TdT (P-L Biochemicals) was further added, and the mixture was incubated at 37° C. for 13 minutes, whereby a (dG) chain comprising about 14 dG residues was added to the 3′ end of the PstI cleavage site of pL1. After phenol-chloroform extraction, DNA was recovered by precipitation with ethanol. The resulting DNA was added to 100 μl of a buffer containing 10 mM Tris-HCl (pH 7.5), 6 mM $MgCl_2$ and 60 mM NaCl, 80 units of HindIII was added, and the mixture was incubated at 37° C. for 3 hours, whereby the pL1 DNA was cleaved at the HindIII site. The reaction mixture was fractionated by agarose gel electrophoresis, and a DNA fragment about 0.5 kb was recovered by the DEAE paper method [Dretzen et al., Anal. Biochem., 112, 295 (1981)]. An oligo(dG) chain-containing linker DNA (hereinafter referred to as "linker DNA" for short) was thus obtained.

About 4 μg of the poly(A) RNA and about 1.4 μg of the vector primer, each prepared as described above, were dissolved in 22.3 μl of a solution containing 50 mM Tris-HCl (pH 8.3), 8 mM $MgCl_2$, 30 mM KCl, 0.3 mM DTT, 2 mM dNTP (dATP, dTTP, dGTP and dCTP) and 10 units of ribonuclease inhibitor (P-L Biochemicals), 10 units of reverse transcriptase (Seikagaku Kogyo) was added, and incubation was performed at 41° C. for 90 minutes for the synthesis of a DNA complementary to the mRNA. The reaction mixture was subjected to phenol-chloroform extraction, followed by precipitation with ethanol, whereby the vector primer DNA with an RNA-DNA double strand added thereto was recovered. The resulting DNA was dissolved in 20 μl of TdT buffer containing 66 μM dCTP and 0.2 μg of poly(A), 14 units of TdT (P-L Bio-chemicals) was added, and the mixture was incubated at 37° C. for 2 minutes for the addition of a (dC) chain comprising 20 dC residues to the 3′ end of cDNA. The reaction mixture was subjected to phenol-chloroform extraction and then a (dC) chain-added cDNA-vector primer DNA was recovered therefrom by precipitation with ethanol. The resulting DNA was dissolved in 400 μl of a solution containing 10 mM Tris-HCl (pH 7.5), 6 mM $MgCl_2$ and 60 mM NaCl, 20 units of HindIII was added, and the cleavage at the HindIII site was effected by performing incubation at 37° C. for 2 hours. The reaction mixture was subjected to phenol-chloroform extraction and then to precipitation with ethanol, which gave 0.5 picomole of a (dC) chain-added cDNA-vector primer DNA. A 0.2-picomole portion of the DNA and 0.4 picomole of the linker DNA mentioned above were dissolved in 100 μl of a solution containing 10 mM Tris-HCl (pH 7.5), 0.1M NaCl and 1 mM EDTA. Incubation was performed at 65° C. for 10 minutes, then at 42° C. for 25 minutes further at 0° C. for 30 minutes. The reaction mixture was modified to give a total volume of 1,000 μl of a reaction mixture containing 20 mM Tris-HCl (pH 7.5), 4 mM $MgCl_2$, 10 mM $(NH_4)_2SO_4$, 0.1M KCl and 0.1 mM β-NAD. To this reaction mixture was added 25 units of *Escherichia coli*-derived DNA ligase (New England Biolabs) and incubation was performed at 11° C. for 18 hours. The reaction mixture was supplemented with dNTP (each to 40 μM) and β-NAD (to 0.15 mM), 10 units of *Escherichia coli*-derived DNA ligase, 20 units of *Escherichia coli*-derived polymerase I (P-L Biochemicals) and 10 units of *Escherichia coli*-derived ribonuclease H (P-L Biochemicals) were added, and incubation was performed at 12° C. for 1 hour and then at 25° C. for 1 hour. In the reactions mentioned above, the cDNA-containing recombinant DNA was circularized and the RNA portion of the RNA-DNA double strand was replaced by DNA, whereby a recombinant plasmid in the form of a complete, double-stranded DNA was formed.

(3) Selection of a human t-PA cDNA-containing recombinant DNA

The t-PA cDNA was selected out, by colony hybridization, as a clone capable of associating with a $^{32}$P-labeled synthetic DNA probe having the DNA sequence 5'-ATGGATGCAAT-GAAGAGAGGGCTCTGCTGT-3' in agreement with a part of the base sequence of the t-PA signal peptide region of the human t-PA cDNA [Pennica et al., Nature, 301, 214 (1983)], as follows.

First, *Escherichia coli* C600SF8 [Cameron, Proc. Natl. Acad. Sci. U.S.A., 72, 3416 (1975)] was transformed with the recombinant plasmid obtained above in section (2) by the method of Hanahan [J. Mol. Biol., 166, 557 (1983)]. About 10,000 colonies obtained were immobilized on a nitrocellulose filter by the method of Hanahan and Meselson [Methods in Enzymology, 100, 333 (1983)]. Then, filter prehydridization was performed in a solution containing 6×NET [1×NET=150 mM NaCl, 15 mM Tris-HCl (pH 7.5), 1 mM EDTA], 10×Denhardt solution and 100 μg/ml of fragmented *Escherichia coli* chromosome DNA at 65° C. for at least 4 hours. The above-mentioned $^{32}$P-labeled probe was added to this prehydridization solution and allowed to associate with DNA on the filter (65° C., at least 16 hours). Then, the filter was washed twice with 6×SSC (1×SSC=150 mM NaCl, 15 mM sodium citrate) (room temperature, 5 minutes/wash) and then washed with a solution containing 2×SSC and 0.1% SDS at 65° C. for 30 minutes. After further washing with a solution containing 2×SSC and 0.1% SDS at 65° C. for 15 minutes, the filter was washed twice with 6×SSC at room temperature (5 minutes per wash). The filter was air-dried and one positive clone was identified by autoradiography. The DNA sequence of the cDNA of the plasmid ptPA7 carried by this positive clone was determined by the dideoxy sequence method using M13 phage. It was found that the cDNA of ptPA7 codes for t-PA completely identical in amino acid sequence to that t-PA reported by Pennica et al. [Nature, 301, 214 (1983)]. It was revealed, however, that the codons for the 95th amino acid (aspartic acid) and 512th amino acid (threonine) of mature t-PA were GAT and ACC instead of GAC and ACA, respectively.

This bacterial strain has been deposited with the Fermentation Research Institute under the designation *Escherichia coli* EtPA7 (FERM BP-1467) under the Budapest Treaty.

REFERENCE EXAMPLE 2

Construction of the human pro-UK cDNA-carrying plasmid pUK1

The Detroit 562 cell-derived cDNA library prepared in Reference Example 1 was screened by the technique of colony hydridization and a human pro-UK cDNA clone was isolated. Thus, the recombinant plasmid obtained in Reference Example 1 was used to transform *Escherichia coli* C600SF8 [Cameron, Proc. Natl. Acad. Sci. U.S.A., 72, 3416 (1975)] by the method of Hanahan [J. Mol. Biol., 166, 557 (1983)]. About 30,000 colonies obtained were immobilized on a nitrocellulose filter by the method of Hanahan and Meselson [Methods in Enzymology, 100, 333 (1983)]. Then, filter prehybridization was effected in a solution containing 6×NET, 10×Denhardt solution and 100 μg/ml of fragmented *Escherichia coli* chromosome DNA at 65° C. for at least 4 hours.

Then, a $^{32}$P-labeled synthetic 41-base DNA probe identical in DNA sequence to a part of the kringle domain of human pro-UK cDNA [Holmes et al., Bio/-Technology, 3, 923 (1985)] and thus having the DNA sequence 5'-GGGAATGGTCACTTTTACCGAG-GAAAGGCCAGCACTGACAC-3' (for the human pro-UK cDNA isolated by the present inventors, this corresponds to the underlined part of the base sequence shown in Table 43) was added to the above-mentioned prehybridization solution and allowed to associate with DNA on the filter (65° C., at least 16 hours). The filter was then washed twice with 6×SSC (room temperature, 5 minutes per wash) and then with a solution containing 1×SSC and 0.1% SDS at 57° C. for 30 minutes. The filter was further washed with a solution containing 1×SSC and 0.1% SDS at 57° C. for 15 minutes and then twice with 6×SSC (room temperature, 5 minutes per wash). The filter was air-dried and one positive clone was identified by autoradiography. The DNA sequence of the cDNA of the plasmid pUK1 carried by this positive clone was determined by the dideoxy method using M13 phage. It was found that the cDNA of pUK1 codes for the translational region for that portion of pro-UK downstream from the 41st amino acid residue (Cys) of pro-UK (according to the numbering of amino acid residues of pro-UK as used in Table 43) and for the 3'-nontranslational region. The amino acid sequence of pro-UK encoded by the cDNA of pUK1 was in agreement with that reported by Holmes et al. [Bio/Technology, 3, 923 (1985)]. However, the codons for the following amino acids were different in the third base from those reported by Holmes et al.:

254th amino acid Asn: AAC→AAT,
340th amino acid Leu: CTA→CTG,
345th amino acid Pro: CCC→CCA,
346th amino acid Gln: CAA→CAG.

The above bacterial strain has been deposited with the Fermentation Research Institute under the designation *Escherichia coli* EUK1 (FERM BP-1463) under the Budapest Treaty.

REFERENCE EXAMPLE 3

Construction of the human pro-UK cDNA-carrying plasmid pUK11

Since the pro-UK cDNA encoded by the plasmid pUK1 obtained in Reference Example 2 does not contain the signal region and growth factor domain region of pro-UK, a cDNA containing these regions was cloned as described below.

First, a vector, pCCK2, for cDNA cloning was constructed as follows.

(1) Construction of the recombinant plasmid pCCK1

*Escherichia coli* HB101 was transformed with the plasmid pRC19 constructed by Kuwano et al. [J. Biochem., 96, 923-926 (1984)] and carrying a cDNA for rat brain cholecystokinin (CCK) precursor was cultured and the pRC19 DNA was prepared from cultured cells in the conventional manner. About 3 μg of the pRC19 DNA obtained was dissolved in 30 μl of Y-50 buffer [solution containing 10 mM Tris-HCl (pH 7.5), 50 mM NaCl, 7 mM MgCl$_2$ and 7 mM 2-mercaptoethanol], 1 unit of PvuII was added, and the digestion reaction was carried out at 37° C. for 1 hour, whereby the DNA was partially digested by PvuII. After 10 minutes of heat treatment at 65° C., a DNA fragment about 530 bp was purified using the AFT method. Separately, about 1 μg of the plasmid DNA pUC19 constructed by Norrander et al. [Norrander, J. et al., Gene, 26, 101 (1983); available from Takara Shuzo] was dissolved in 30 μl of Y-0 buffer containing 20 mM KCl, 16 units of SmaI was added, and the digestion reaction was carried out at 30° C. for 2 hours. After 10 minutes of heat treatment at 65° C., a DNA fragment about 2.7 kb was purified using the AFT method.

The thus-obtained pRC19-derived DNA fragment (about 530 bp, about 0.01 μg) and pUC19-derived DNA fragment (about 2.7 kb, about 0.05 μg) were dissolved in 20 μl of T4 ligase buffer, 200 units of T4 DNA ligase was added, and the ligation reaction was carried out at 4° C. for 18 hours.

The recombinant plasmid mixture obtained was used to transform *Escherichia coli* MM294 to give Ap-resistant transformants. The plasmid DNA pCCK1 isolated from one of these transformants was subjected to structural analysis with restriction enzymes and found to have the desired structure (cf. FIG. 9).

(2) Construction of the recombinant plasmid pCCK2

About 2 μg of the pCCK1 plasmid DNA obtained as described above was dissolved in 30 μl of Y-0 buffer, 12 units of SacI was added, and the digestion reaction was performed at 37° C. for 2 hours. Then, 1.5 μl of 2M NaCl and 10 units of BamHI were added, and the digestion reaction was further conducted at 37° C. for 2 hours. After 10 minutes of heat treatment at 65° C., a DNA fragment about 0.55 kb was purified using the AFT method. Separately, about 2 μg of the pTrS33 plasmid DNA obtained in Reference Example 4 to be given later herein was treated in the same manner as mentioned above and a SacI-BamHI fragment about 2.85 kb was purified using the AFT method.

The thus-obtained pCCK1-derived DNA fragment (about 0.55 kb, about 0.02 μg) and pTrS33-derived DNA fragment (about 2.85 kb, about 0.1 μg) were dissolved in 20 μl of T4 ligase buffer, 50 units of T4 DNA ligase was added, and the ligation reaction was conducted at 4° C. for 18 hours.

The recombinant plasmid mixture obtained was used to transform *Escherichia coli* MM294 to give Ap-resistant transformants. The plasmid DNA pCCK2 isolated from one of these transformants was subjected to structural analysis using restriction enzymes and found to have the desired structure (cf. FIG. 10).

(3) Isolation of the human pro-UK cDNA-carrying plasmid pUK11

About 8 μg of the Detroit 562 cell-derived poly(A) RNA (mRNA) [dissolved in 7 μl of 10 mM Tris-HCl (pH 7.5)-0.5 mM EDTA] was heated at 65° C. for 10 minutes and then quenched in ice. The composition of this solution was adjusted so that the resultant solution contained, in a total volume of 80 μl, 50 mM Tris-HCl (pH 8.3), 8 mM MgCl$_2$, 30 mM KCl, 5 mM DTT, 1 mM dNTP (dATP, dTTP, dGTP and dCTP), 10 units of ribonuclease inhibitor (P-L Biochemicals) and 5 μg/ml of oligo-(dT)$_{12-18}$ (Collaborative Research). The solution was maintained at 41° C. for 15 minutes. Then, 20 units of reverse transcriptase (Seikagaku Kogyo) was added and the mixture was maintained at 41° C. for 90 minutes for the synthesis of cDNA complementary to the mRNA. The reaction mixture was subjected to phenol-chloroform extraction. Addition of ethanol gave a precipitate, which was dissolved in 40 μl of 0.3M NaOH. The solution was allowed to stand at 37° C. for 15 hours for effecting the hydrolysis of mRNA. Then, the solution was neutralized by addition of 10 μl of 1M Tris-HCl (pH 7.5) and 40 μl of 0.3N HCl, and a single-stranded cDNA was recovered by precipitation with ethanol and dissolved in 28.5 μl of H$_2$O.

The composition of this solution was adjusted so that the resultant solution contained, in a total volume of 40 μl, 50 mM Tris-HCl (pH 8.3), 8 mM MgCl$_2$, 30 mM KCl, 5 mM DTT, 1 mM dNTP (dATP, dTTP, dGTP and dCTP) and 2.5 μg/ml of the synthetic DNA primer CATGAGAGCCCTGCTGG (identical to a part of the base sequence for the signal peptide region of human pro-UK). The solution was maintained at 65° C. for 10 minutes and then at 41° C. for 30 minutes. Then, 10 units of reverse transcriptase was added, and the mixture was maintained at 41° C. for 60 minutes for conversion of the single stranded cDNA to a double-stranded cDNA. The reaction mixture was subjected to phenol-chloroform extraction. Addition of ethanol gave a precipitate, which was dissolved in 30 μl of Y-0 buffer containing 25 mM NaCl, 25 units of BssHII (New England Biolabs) was added to the solution, and the digestion reaction was conducted at 50° C. for 2 hours. Furthermore, 1.25 μl of 2M NaCl and 12 units of BamHI were added, and the digestion reaction was further conducted at 37° C. for 2 hours. After 10 minutes of heat treatment at 65° C., a cDNA fragment about 1.1 to 1.4 kb was purified using the AFT method.

Separately, about 2 μg of the pCCK2 plasmid DNA obtained as described above was cleaved with BssHII and BamHI in the same manner as above, and a BssHII-BamHI fragment about 2.9 kb was purified using the AFT method.

The thus-obtained cDNA fragment (about 1.1 to 1.4 kb, about 0.02 μg) and pCCK2-derived DNA fragment (about 2.9 kb, about 0.05 μg) were dissolved in 20 μl of T4 ligase buffer, 200 units of T4 DNA ligase was added, and the ligation reaction was conducted at 4° C. for 18 hours.

The reaction mixture obtained was used to transform *Escherichia coli* C600SF8 to give about 25,000 Ap-resistant transformants. From among these Ap-resistant strains, about 1,000 positive clones were obtained by the colony hybridization method mentioned in Reference Example 2, which were capable of associating with the same probe as used for isolating the pro-UK cDNA in Reference Example 2. The hybridization conditions and filter washing conditions were the same as employed in Reference Example 2. The plasmid pUK11 (cf. FIG. 11) isolated from one of the positive clones thus obtained was subjected to base sequence determination for the pro-UK signal peptide, growth factor domain and kringle domain regions by the dideoxy method using M13 phage. The DNA sequence thus found were in agreement with those reported by Holmes [Bio/Technology, 3, 923 (1985)].

REFERENCE EXAMPLE 4

Construction of the recombinant plasmid pTrS33:

(1) Construction of the ATG vector pTrS20:

According to the scheme shown in FIG. 12, the ATG vector pTrS20 in which the SD sequence is apart by 14 bases from the initiation codon ATG and which has a SacI site just behind the ATG codon was constructed.

First, 3 μg of pKYP10 prepared as described in U.S. Pat. No. 4,686,191 was dissolved in 30 μl of Y-100 buffer, 6 units of the restriction enzyme BanIII and 6 units of the restriction enzyme NruI (New England Biolabs) were added, and the cleavage reaction was conducted at 37° C. for 3 hours. From the reaction mixture, there was recovered about 0.5 μg of a Ptrp-containing DNA fragment (BanIII-NruI fragment) of about 3.8 kb by the LGT method.

Separately, the following DNA linker was synthesized by the phosphotriester method for providing the initiation codon ATG downstream from Ptrp.

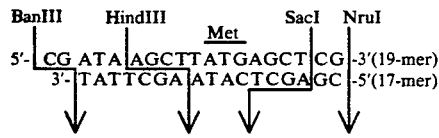

The synthetic 19-mer and 17-mer DNAs (10 picomoles each) were dissolved in a total volume of 20 μl of a solution containing 50 mM Tris-HCl (pH 7.5), 10 mM MgCl$_2$, 5 mM dithiothreitol, 0.1 mM EDTA and 1 mM ATP, 3 units of T4 polynucleotide kinase (Takara Shuzo) was added, and the phosphorylation reaction was conducted at 37° C. for 60 minutes.

Then, 0.1 μg of the pKYP10-derived BanIII-NruI fragment (about 3.8 kb) obtained as described above and about 0.5 picomole of the DNA linker mentioned above were dissolved in 20 μl of T4 ligase buffer, 2 units of T4 DNA ligase was added, and the ligation reaction was conducted at 4° C. for 18 hours.

The recombinant plasmid mixture obtained was used to transform *Escherichia coli* HB101 [Bolivar et al., Gene, 2, 75 (1977)] to give Ap-resistant colonies. Each colony was cultured and a plasmid DNA was recovered from cultured cells and examined for its structure by cleavage with the restriction enzymes EcoRI, BanIII, HindIII, SacI and NruI, followed by agarose gel electrophoresis. A plasmid found to have the desired structure was named pTrS20 (cf. FIG. 12). It was confirmed by the dideoxy sequence method using M13 phage that pTrS20 had the following DNA sequence in the neighborhood of the BanIII and HindIIII sites

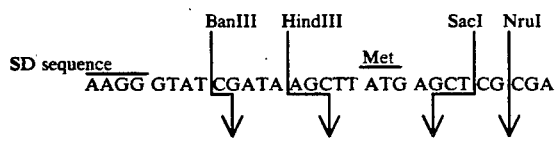

(2) Construction of pTrS33

About 3 μg of the pTrS20 plasmid DNA obtained as described above was dissolved in 30 μl of Y-0 buffer, 12 units of SacI was added, and the digestion reaction was conducted at 37° C. for 2 hours. Then, 1.5 μl of 2M NaCl and 10 units of PstI were added, and the digestion reaction was further conducted at 37° C. for 2 hours. After 10 minutes of heat treatment at 65° C., a DNA fragment about 1.15 kb was purified by the AFT method. Separately, 2 μg of pKYP26 prepared as described in EP-A-0214555 [an *Escherichia coli* strain harboring pKYP26 has been deposited with the Fermentation Research Institute under the designation *Escherichia coli* IKYP26 (FERM BP-863) under the Budapest Treaty] was dissolved in 30 μl of Y-100 buffer, 8 units of PstI and 10 units of BamHI were added, and the digestion reaction was conducted at 37° C. for 2 hours. After 10 minutes of heat treatment at 65° C., a DNA fragment about 1.7 khb was purified by the AFT method. Further, separately, 2 μg of the M13mp18 RF DNA [Norrander, J. et al., Gene, 26, 101 (1983); obtained from Takara Shuzo] was dissolved in 30 μl of Y-0 buffer, 10 units of SacI was added, and the digestion reaction was conducted at 37° C. for 2 hours. Then, 1.5 μl of 1M NaCl and 10 units of ClaI were added, and the digestion reaction was further conducted at 37° C. for 2 hours. After 10 minutes of heat treatment at 65° C., a DNA fragment about 0.65 kb was purified by the AFT method. Further, separately, the following two synthetic DNAs (43 bases and 45 bases) (also shown in FIG. 13) were synthesized using an Applied Biosystems model 380A DNA synthesizer:

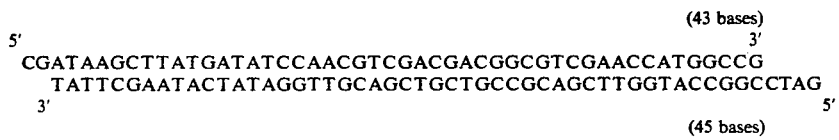

They were separately 5′-phosphorylated in the same manner as described hereinbefore.

The thus-obtained pTrS20-derived DNA fragment (about 1.15 kb, about 0.1 μg), pKYP26-derived DNA fragment (about 1.7 kb, about 0.1 μg), M13mp18-derived DNA fragment (about 0.65 kb, about 0.05 μg) and two 5′-phosphorylated synthetic DNAs (1 picomole each) were dissolved in 20 μl of T4 ligase buffer, 50 units of T4 DNA ligase was added, and the ligation reaction was conducted at 4° C. for 18 hours.

The recombinant plasmid mixture thus obtained was used to transform *Escherichia coli* MM294 to give Ap-resistant transformants. The plasmid pTrS33 isolated from one of these transformants was found to have the desired structure upon structural analysis comprising digestion with restriction enzymes and DNA sequencing by the dideoxy method using M13 phage (cf. FIG. 13).

REFERENCE EXAMPLE 5

Construction of the recombinant plasmid pTerm2

About 2 μg of the pKYP26 plasmid DNA (EP-A-0214555) was dissolved in 30 μl of a solution containing 10 mM Tris-HCl (pH 8.0), 75 mM NaCl, 7 mM MgCl$_2$ and 6 mM 2-mercaptoethanol, 16 units of Asp718 (Boehringer-Mannheim) and 10 units of PstI were added, and the digestion reaction was conducted at 37° C. for 2 hours. After 10 minutes of heat treatment at 65° C., a DNA fragment about 1.7 kb was purified using the AFT method. Separately, about 2 μg of the pTrS20 plasmid DNA obtained in Reference Example 4-(1) was dissolved in 30 μl of Y-100 buffer, 8 units of PstI and 10 units of NruI (Boehringer-Mannheim) were added, and the digestion reaction was conducted at 37° C. for 2 hours. After 10 minutes of heat treatment at 65° C., a DNA fragment about 1.5 kb was purified using the AFT method. Further, separately, the two synthetic DNAs (19 bases and 23 bases) shown in FIG. 14 were synthesized using an Applied Biosystems model 380A DNA synthesizer and respectively 5′-phosphorylated by the same method as mentioned hereinabove.

The thus-obtained pKYP26-derived DNA fragment (about 1.7 kb, about 0.1 μg), pTrS20-derived DNA fragment (about 1.15 kb) and two 5'-phosphorylated synthetic DNAs (1 picomole each) were dissolved in 20 μl of T4 ligase buffer, 50 units of T4 DNA ligase was added, and the ligation reaction was conducted at 4° C. for 18 hours.

The reaction mixture obtained was used to transform *Escherichia coli* MM294 to give Ap-resistant transformants. The plasmid DNA pTerm2 isolated from one of these transformants was found to have the desired structure upon structural analysis comprising digestion with restriction enzymes and DNA sequencing by the dideoxy method using M13 phage (cf. FIG. 14).

REFERENCE EXAMPLE 6

Construction of the recombinant plasmid pTkSS4

(1) Construction of the recombinant plasmid pTSF10

*Escherichia coli* C600SF8 transformed with the human t-PA cDNA-containing plasmid ptPA7 obtained in Reference Example 1 was cultured and the ptPA7 DNA was prepared from cultured cells by a conventional method. About 2 μg of the ptPA7 DNA obtained was dissolved in 30 μl of Y-100 buffer, 8 units of BglII was added, and the digestion reaction was conducted at 37° C. for 2 hours. After 10 minutes of heat treatment at 65° C., a DNA fragment about 2.0 kb was purified using the AFT method. Separately, about 2 μg of the pTrS33 DNA (Reference Example 4) was dissolved in 30 μl of Y-100 buffer, 10 units of the restriction enzyme BamHI was added, and the digestion reaction was conducted at 37° C. for 2 hours. After 10 minutes of heat treatment at 65° C., a DNA fragment about 2.8 kb was purified using the AFT method.

The thus-obtained ptPA7-derived DNA fragment (about 2.0 kb, about 0.1 μg) and pTrS33-derived DNA fragment (about 2.8 kb, about 0.1 μg) were dissolved in 20 μl of T4 ligase buffer, 50 units of T4 DNA ligase was added, and the ligation reaction was conducted at 4° C. for 18 hours.

The reaction mixture obtained was used to transform *Escherichia coli* MM294 to give Ap-resistant transformants. The plasmid DNA pTSF10 isolated from one of these transformants was found to have the desired structure upon structural analysis comprising digestion with restriction enzymes (cf. FIG. 15).

Construction of the recombinant plasmid pTA4

About 3 μg of the pTSF10 plasmid DNA obtained as described above was dissolved in 30 μl of Y-0 buffer, 12 units of KpnI was added, and the digestion reaction was conducted at 37° C. for 2 hours. Then, 1.5 μl of 3M NaCl and 12 units of BstEII (New England Biolabs) were added, and the digestion reaction was further conducted at 60° C. for 2 hours. Then, a DNA fragment about 0.3 kb was purified using the AFT method.

Separately, *Escherichia coli* IGHA2 (deposited with the Fermentation Research Institute under the deposit number FERM BP-400) was cultured and the pGHA2 plasmid DNA (U.S. Pat. No. 4,868,125) was prepared from cultured cells by a conventional method. About 2 μg of the pGHA2 DNA obtained was dissolved in 30 μl of Y-100 buffer, 8 units of PstI and 8 units of BglII were added, and the digestion reaction was conducted at 37° C. for 2 hours. After 10 minutes of heat treatment at 65° C., a DNA fragment about 0.75 kb was purified using the AFT method.

Further, separately, about 3 μg of the ptPA7 DNA (Reference Example 1) was dissolved in 30 μl of a solution containing 20 mM Tris-HCl (pH 7.6), 150 mM NaCl, 7 mM MgCl₂ and 6 mM 2-mercaptoethanol (hereinafter referred to as "Y-150 buffer"), 10 units of BglII was added, and the digestion reaction was conducted at 37° C. for 2 hours. Then, 12 units of BstEII was added and the digestion reaction was further conducted at 60° C. for 2 hours. A DNA fragment about 1.55 kb was purified from the reaction mixture using the AFT method.

Further, separately, about 2 μg of the pTerm2 DNA obtained in Reference Example 5 was digested in 30 μl of Y-0 buffer in the presence of 12 units of KpnI at 37° C. for 2 hours. Then, 1.5 μl of 2M NaCl and 8 units of PstI were added, and the digestion reaction was further conducted at 37° C. for 2 hours. Thereafter, a DNA fragment about 1.7 kb was purified using the AFT method.

The thus-obtained four DNA fragments (0.03 μg of the pTSF10-derived fragment, 0.05 μg of the pGHA2-derived fragment, 0.1 μg of the ptPA7-derived fragment and 0.1 μg of the pTerm2-derived fragment) were dissolved in 20 μl of T4 ligase buffer, 50 units of T4 DNA ligase was added, and the ligation reaction was conducted at 4° C. for 18 hours.

The reaction mixture obtained was used to transform *Escherichia coli* MM294 to give Ap-resistant transformants. The plasmid DNA pTA4 isolated from one of these transformants was found to have the desired structure upon structural analysis comprising digestion with restriction enzymes (cf. FIG. 16).

(3) Construction of the recombinant plasmid pTkSD217

About 10 μg of the pTA4 plasmid DNA obtained as described above was dissolved in 100 μl of Y-100 buffer, 30 units of XhoI was added, and the digestion reaction was conducted at 37° C. for 2 hours. After phenol extraction and chloroform extraction, the product DNA fragment was recovered by precipitation with ethanol and dissolved in 50 μl of TE buffer [10 mM Tris-HCl (pH 7.5), 0.5 mM EDTA]. To 10 μl of this DNA solution were added 10 μl of 5 times concentrated BAL31 buffer [100 mM Tris-HCl (pH 8.0), 3M NaCl, 60 mM CaCl₂, 60 mM MgCl₂, 5 mM EDTA], 30 μl of water and 0.5 unit of the exonuclease BAL31 (Takara Shuzo), and the reaction was conducted at 30° C. for 5 minutes. These are the conditions under which DNA can be pared off by about 0.5 kb from the XhoI terminus. The reaction was terminated by extraction with phenol. After further extraction with chloroform, the product DNA fragment was recovered by precipitation with ethanol. This DNA fragment was dissolved in 30 μl of Y-100 buffer, 10 units of BamHI was added, and the digestion reaction was conducted at 37° C. for 2 hours. After 10 minutes of heat treatment at 65° C., a DNA fragment about 1.5 kb was purified using the AFT method.

Separately, about 2 μg of the pTrS33 plasmid DNA (Reference Example 4) was digested in 30 μl of Y-0 buffer in the presence of about 12 units of SacI at 37° C. for 2 hours. After phenol extraction and chloroform extraction, the product DNA fragment was recovered by precipitation with ethanol and dissolved in a total volume of 40 μl of a buffer containing 50 mM Tris-HCl (pH 7.8), 7 mM MgCl₂, 6 mM 2-mercaptoethanol, 0.25 mM dATP, 0.25 mM dCTP, 0.25 mM dGTP and 0.25 mM dTTP (hereinafter referred to as "polymerase buffer"), 6 units of Klenow fragment (Klenow Pol I) (Takara Shuzo) were added, and the reaction was conducted at 15° C. for 1 hour to thereby convert the SacI protruding ends to blunt ends. The reaction was terminated by extraction with phenol. After chloroform extraction, a DNA fragment was recovered by precipitation with ethanol. This DNA fragment was dissolved in 30 μl of Y-100 buffer, 10 units of BamHI was added, and the digestion reaction was conducted at 37° C. for 2 hours. After 10 minutes of heat treatment at 65° C., a DNA fragment about 2.8 kb was purified using the AFT method.

The thus-obtained pTA4-derived DNA fragment (about 1.5 kg, about 0.2 μg) and pTrS33-derived DNA fragment (about 2.8 kb, about 0.1 μg) were dissolved in 20 μl of T4 ligase buffer, 50 units of T4 DNA ligase was added, and the ligation reaction was conducted at 4° C. for 18 hours.

The reaction mixture obtained was used to transform *Escherichia coli* MM294 to give Ap-resistant transformants. The plasmid DNA pTkSD217 isolated from one of these transformants was subjected to structural analysis comprising digestion with restriction enzymes and its DNA sequence downstream from the *Escherichia coli* trypophan promtor (Ptrp) was determined by the dideoxy sequence method using M13 phage [J. Messing et al., *Gene*, 19, 269 (1985)]. As a result, it was confirmed that pTkSD217 had the desired structure and that the DNA sequence was as follows (cf. FIG. 17).

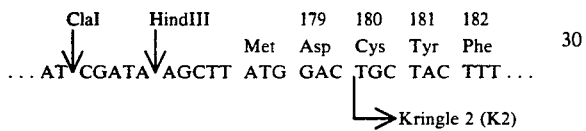

(4) Construction of the recombinant plasmid pTkSL11

About 3 μg of the pTkSD217 plasmid DNA obtained as described above was dissolved in 30 μl of Y-100 buffer, 10 units of HindIII and 15 units of ScaI were added, and the digestion reaction was conducted at 37° C. for 2 hours. After 10 minutes of heat treatment at 65° C., a DNA fragment about 0.23 kb was purified using the AFT method. Separately, about 2 μg of the pTerm2 plasmid DNA obtained in Reference Example 5 was dissolved in 30 μl of Y-100 buffer, 10 units of HindIII and 10 units of NsiI (New England Biolabs) were added, and the digestion reaction was conducted at 37° C. for 2 hours. After 10 minutes of heat treatment at 65° C., a DNA fragment about 2.8 kb was purified using the AFT method. Furthermore, the following two synthetic DNAs (35 bases and 31 bases) were synthesized using an Applied Biosystems model 380A DNA synthesizer and respectively 5'-phosphorylated by the method mentioned hereinbefore.

The thus-obtained pTkSD217-derived DNA fragment (about 0.23 kb, about 0.01 μg), pTerm2-derived DNA fragment (about 2.8 kb, about 0.1 μg) and two 5'-phosphorylated synthetic DNAs (1 picomole each) were dissolved in 20 μl of T4 ligase buffer, 300 units of T4 DNA ligase was added, and the ligation reaction was conducted at 4° C. for 18 hours.

The reaction mixture obtained was used to transform *Escherichia coli* MM294 to give Ap-resistant transformants. The plasmid DNA pTkSL11 isolated from one of these transformants was found to have the desired structure upon structural analysis comprising digestion with restriction enzymes and DNA sequence determination by the M13 dideoxy sequence method (cf. FIG. 18).

(5) Construction of the recombinant plasmid pTkSS4

About 2 μg of the ptPA7 plasmid DNA obtained in Reference Example 1 was dissolved in 30 μl of Y-100 buffer, 12 units of the restriction enzyme ScaI, and the digestion reaction was conducted at 37° C. for 2 hours. After 10 minutes of heat treatment at 65° C., a DNA fragment about 2.0 kb was purified using the AFT method. Separately, about 2 μg of the pTkSL11 plasmid DNA obtained as described above was subjected to the same reaction as above and, after 10 minutes of heat treatment at 65° C., a DNA fragment about 2.0 kb was purified using the AFT method.

The thus-obtained ptPA7-derived DNA fragment (about 2.0 kb, about 0.1 μg) and pTkSL11-derived DNA fragment (about 2.0 kb, about 0.1 μg) were dissolved in 20 μl of T4 ligase buffer, 300 units of T4 DNA ligase was added, and the ligation reaction was conducted at 4° C. for 18 hours.

The reaction mixture obtained was used to transform *Escherichia coli* MM294 to give Ap-resistant transformants. The plasmid DNA pTkSS4 isolated from one of these transformants was found to have the desired structure upon structural analysis comprising digestion with restriction enzymes (cf. FIG. 19).

REFERENCE EXAMPLE 7

Construction of the recombinant plasmid pTkSR18

(1) Construction of the recombinant plasmid pTkSJ1

About 2 μg of the pTA4 plasmid obtained in Reference Example 6-(2) was dissolved in 30 μl of Y-0 buffer, 10 units of EcoRI and 30 units of BbeI were added, and the digestion reaction was conducted at 37° C. for 2 hours. After 10 minutes of heat treatment at 65° C., a BbeI-EcoRI fragment about 2.8 kb was purified using the AFT method. Separately, about 3 μg of the pTA4 DNA was dissolved in 30 μl of Y-0 buffer, 12 units of KpnI was added, and the digestion reaction was conducted at 37° C. for 2 hours. Then, 1.5 μl of 2M NaCl and 1 unit of EcoRI were added and the digestion reaction was further conducted at 37° C. for 1 hour. Under these reaction conditions, the digestion of the DNA with KpnI was complete and that with EcoRI was partial. After 10 minutes of heat treatment at 65° C., an EcoRI-KpnI fragment about 1.4 kb was purified using the AFT method. Separately, the following two synthetic DNAs (16 bases and 24 bases) were synthesized using an Applied Biosystems model 380A DNA synthesizer and respectively 5'-phosphorylated in the same manner as mentioned hereinabove.

The thus-obtained pTA4-derived BbeI-EcoRI fragment (about 2.8 kb, about 0.1 μg), pTA4-derived EcoRI-KpnI fragment (about 1.4 kb, about 0.05 μg) and two 5'-phosphorylated synthetic DNAs (1 picomole each) were dissolved in 20 μl of T4 ligase buffer, 50 units of T4 DNA ligase was added, and the ligation reaction was conducted at 4° C. for 18 hours.

The reaction mixture obtained was used to transform *Escherichia coli* MM294 to give Ap-resistant transformants. The plasmid DNA pTkSJ1 isolated from one of these transformants was found to have the desired structure upon structural analysis comprising digestion with restriction enzymes and DNA sequencing by the dideoxy method using M13 phage (cf. FIG. 20).

(2) Construction of the recombinant plasmid pTkSR18

About 3 μg of the pTkSJ1 plasmid DNA obtained as described above was dissolved in 30 μl of Y-100 buffer, 10 units of XhoI and 15 units of ScaI were added, and the digestion reaction was conducted at 37° C. for 2 hours. After 10 minutes of heat treatment at 65° C., a DNA fragment about 0.5 kb was purified using the AFT method. Separately, about 2 μg of the pTrS33 plasmid DNA obtained in Reference Example 4 was dissolved in Y-0 buffer containing 150 mM KCl, 8 units of PvuI and 15 units of SalI were added, and the digestion reaction was conducted at 37° C. for 2 hours. After 10 minutes heat treatment at 65° C., a DNA fragment about 1.0 kb was purified using the AFT method. Further, separately, about 2 μg of the pTerm2 plasmid DNA obtained in Reference Example 5 was dissolved in 30 μl of Y-150 buffer, 8 units of PvuI and 8 units of NsiI (New England Biolabs) were added, and the digestion reaction was conducted at 37° C. for 2 hours. After 10 minutes of heat treatment at 65° C., a DNA fragment about 1.85 kb was purified using the AFT method. Furthermore, the following two synthetic DNAs (35 bases and 31 bases) were synthesized using an Applied Biosystems model 380A DNA synthesizer and respectively 5'-phosphorylated by the same method as mentioned above.

of the restriction enzyme NcoI and 8 units of the restriction enzyme StuI were added, and the digestion reaction was conducted at 37° C. for 2 hours. After 10 minutes of heat treatment at 65° C., a DNA fragment about 1.2 kb was purified using the AFT method. Separately, about 2 μg of the pTrS33 plasmid DNA obtained in Reference Example 4 was dissolved in 30 μl of a solution containing 10 mM Tris-HCl (pH 7.5), 25 mM KCl, 7 mM MgCl₂ and 6 mM 2-mercaptoethanol (hereinafter referred to as "K-25 buffer"), 16 units of the restriction enzyme SmaI was added, and the digestion reaction was conducted at 30° C. for 2 hours. Then, 1.5 μl of 1M NaCl and 10 units of NcoI were added, and the digestion reaction was further conducted at 37° C. for 2 hours. After 10 minutes of heat treatment at 65° C., a DNA fragment about 2.85 kb was purified using the AFT method.

The thus-obtained pUK1-derived DNA fragment (about 1.2 kb, about 0.05 μg) and pTrS33-derived DNA fragment (about 2.85 kb, about 0.1 μg) were dissolved in 20 μl of a buffer containing 20 mM Tris-HCl (pH 7.6), 10 mM MgCl₂, 10 mM dithiothreitol (DTT) and 1 mM ATP, 100 units of T4 DNA ligase was added, and the ligation reaction was conducted at 4° C. for 18 hours.

The reaction mixture thus obtained was used to transform *Escherichia coli* MM294 to give ampicillin Ap-resistant transformants. The plasmid DNA pUKA2 isolated from one of these transformants was found to have the desired structure upon structural analysis comprising digestion with restriction enzymes (cf. FIG. 22).

(2) Construction of the recombinant plasmid pUKB101

About 2 μg of the pUKA2 plasmid DNA obtained as described above was dissolved in 30 μl of Y-0 buffer, 12 units of the restriction enzyme KpnI was added, and the digestion reaction was conducted at 37° C. for 2 hours.

```
5'-ACTGTGACGTCCCCAGCTGTTCTGAAGGAAATGCA-3'
3'-TGACACTGCAGGGGTCGACAAGACTTCCTTT-5'
```

The thus-obtained pTkSJ1-derived XhoI-ScaI fragment (about 0.5 kb, about 0.05 μg), and pTrS33-derived PvuI-SalI fragment (about 1.0 kb, about 0.1 μg), pTerm2-derived NsiI-PvuI fragment (about 1.85 kg, about 0.1 μg) and two 5'-phosphorylated synthetic DNAs (1 picomole each) were dissolved in 20 μl of T4 ligase buffer, 50 units of T4 DNA ligase was added, and the ligation reaction was conducted at 4° C. for 18 hours.

The reaction mixture thus obtained was used to transform *Escherichia coli* MM294 to give Ap-resistant transformants. The plasmid DNA pTkSR18 isolated from one of these transformants was found to have the desired structure upon structural analysis comprising digestion with restriction enzymes and DNA sequencing by the dideoxy method using M13 phage (cf. FIG. 21).

REFERENCE EXAMPLE 8

Construction of the recombinant plasmid pUKB101

(1) Construction of the recombinant plasmid pUKA2

The pUK1 DNA was prepared from an *Escherichia coli* C600SF8 transformant strain harboring the human pro-UK cDNA-containing plasmid pUK1 obtained in Reference Example 2. About 2 μg of the pUK1 DNA obtained was dissolved in 30 μl of Y-100 buffer, 8 units Then, 1.5 μl of 2M NaCl and 10 units of NcoI and the digestion reaction was further conducted at 37° C. for 2 hours. After 10 minutes of heat treatment at 65° C., a DNA fragment about 1.2 kb was purified using the AFT method. Separately, about 2 μg of the pTrS33 plasmid DNA obtained in Reference Example 4 was dissolved in 30 μl of K-25 buffer, 16 units of SmaI was added, and the digestion reaction was conducted at 30° C. for 2 hours. Then, 1.5 μl of 2M NaCl and 10 units of PstI were added, and the digestion reaction was further conducted at 37° C. for 2 hours. After 10 minutes of heat treatment at 65° C., a DNA fragment about 1.15 kb was purified using the AFT method. Separately, about 2 μg of the pTerm2 plasmid DNA obtained in Reference Example 5 was dissolved in 30 μl of Y-0 buffer, 12 units of KpnI was added, and the digestion reaction was conducted at 37° C. for 2 hours. Then, 1.5 μl of 2M NaCl and 10 units of PstI were added, and the digestion reaction was further conducted at 37° C. for 2 hours. After 10 minutes of heat treatment at 65° C., a DNA fragment about 1.7 kb was purified using the AFT method. Furthermore, the following two synthetic DNAs (41 bases and 45 bases) were synthesized using an Applied Biosystems model 380A DNA synthesizer.

```
5'-GGGAATGGTCACTTTTACCGAGGAAAGGCCAGCACTGACAC-3'
                                                           (41 bases)
3'-CCCTTACCAGTGAAAATGGCTCCTTTCCGGTCGTGACTGTGGTAC-5'
                                                           (45 bases)
```

These synthetic DNAs (20 picomoles each) were individually phosphorylated at the 5' end by conducting the reaction in 20 μl of T4 kinase buffer in the presence of 5 units of T4 DNA kinase at 37° C. for 30 minutes.

The thus-obtained pUKA2-derived DNA fragment (about 1.2 kb, about 0.05 μg), pTrS33-derived DNA fragment (about 1.15 kb, about 0.05 μg), pTerm2-derived DNA fragment (about 1.7 kb, about 0.05 μg) and two 5'-phosphorylated synthetic DNAs (1 picomole each) were dissolved in 20 μl of T4 ligase buffer, 300 units of T4 DNA ligase was added, and the ligation reaction was conducted at 4° C. for 18 hours.

The reaction mixture obtained was used to transform *Escherichia coli* MM294 to give Ap-resistant transformants. The plasmid DNA pUKB101 isolated from one of these transformants was found to have the desired structure upon structural analysis comprising digestion with restriction enzymes and DNA sequence determination by the M13 dideoxy sequence method (cf. FIG. 22).

REFERENCE EXAMPLE 9

Construction of the recombinant plasmid pTG3

About 2 μg of the pTkSS4 plasmid DNA obtained in Reference Example 6 was dissolved in 30 μl of Y-0 buffer, 10 units of the restriction enzyme NarI (New England Biolabs) was added, and the digestion reaction was conducted at 37° C. for 2 hours. Then, 1.0 μl of 2M

REFERENCE EXAMPLE 10

Construction of the recombinant plasmid phPA2

About 2 μg of the pTG3 plasmid DNA obtained in Reference Example 9 was dissolved in 30 μl of Y-100 buffer, 10 units each of EcoRI and PvuI were added, and the digestion reaction was conducted at 37° C. for 2 hours. After 10 minutes of heat treatment at 65° C., a DNA fragment about 1.7 kb was purified using the AFT method.

Separately, about 2 μg of the pUKB101 plasmid DNA obtained in Reference Example 8 was dissolved in 30 μl of Y-100 buffer, 10 units each of NcoI and PvuI were added, and the digestion reaction was conducted at 37° C. for 2 hours. After 10 minutes of heat treatment at 65° C., a DNA fragment about 3.0 kb was purified using the AFT method.

Further, separately, about 2 μg of the pTkSR18 plasmid DNA obtained in Reference Example 7 was dissolved in 30 μl of Y-100 buffer, 10 units each of HindIII and AatII were added, and the digestion reaction was conducted at 37° C. for 2 hours. After 10 minutes of heat treatment at 65° C., a DNA fragment about 0.55 kb was purified using the AFT method.

Furthermore, the following four synthetic DNAs (37 bases and 41 bases as well as 41 bases and 45 bases) were synthesized using an Applied Biosystems model 380A DNA synthesizer.

```
5'-     CCCCAGCTGTTCTGAAGGAAATAGTGACTGCTATGAG   -3'
                                                           (37 bases)
3'-TGCAGGGGTCGACAAGACTTCCTTTATCACTGACGATACTC-5'
                                                           (41 bases)
5'-GGGAATGGTCACTTTTACCGAGGAAAGGCCAGCACTGACAC    -3'
                                                           (41 bases)
3'-CCCTTACCAGTGAAAATGGCTCCTTTCCGGTCGTGACTGTGGTAC-5'
                                                           (45 bases)
```

NaCl and 12 units of BamHI were added, and the digestion reaction was further conducted at 37° C. for 2 hours. After 10 minutes of heat treatment at 65° C., a DNA fragment about 3.3 kb was purified using the AFT method. Separately, about 3 μg of the pTkSR18 plasmid DNA obtained in Reference Example 7 was subjected to the same reaction as above and, after 10 minutes of heat treatment at 65° C., a DNA fragment about 0.2 kb was purified using the AFT method.

The thus-obtained pTkSS4-derived DNA fragment about 3.3 kb, about 0.1 μg) and pTkSR18-derived DNA fragment (about 0.2 kb, about 0.01 μg) were dissolved in 20 μl of T4 ligase buffer, 100 units of T4 DNA ligase was added, and the ligation reaction was conducted at 4° C. for 18 hours.

The reaction mixture thus obtained was used to transform *Escherichia coli* MM294 to give Ap-resistant transformants. The plasmid DNA pTG3 isolated from one of these transformants was found to have the desired structure upon structural analysis comprising digestion with restriction enzymes (cf. FIG. 24).

These synthetic DNAs (20 picomoles each) were individually phosphorylated at the 5' end by conducting the reaction in 20 μl of T4 kinase buffer in the presence of 5 units of T4 DNA kinase at 37° C. for 30 minutes.

The thus-obtained pTG3-derived DNA fragment (about 1.7 kb, about 0.05 μg), pUK101-derived DNA fragment (about 3.0 kb, about 0.05 μg), pTkSR18-derived DNA fragment (about 0.55 kb, about 0.05 μg) and four 5'-phosphorylated synthetic DNAs (1 picomole each) were dissolved in 20 μl of T4 ligase buffer, 300 units of T4 DNA ligase was added, and the ligation reaction was conducted at 4° C. for 18 hours.

The reaction mixture obtained was used to transform *Escherichia coli* MM294 to give Ap-resistant transformants. The plasmid DNA phPA2 isolated from one of these transformants was found to have the desired structure upon structural analysis comprising digestion with restriction enzymes and DNA sequence determination by the M13 dideoxy sequence method (cf. FIG. 25).

REFERENCE EXAMPLE 11

Construction of the recombinant plasmid pUKS1 coding for the pro-UK derivative UK-S1

(1) Construction of a single-stranded template DNA (single-stranded pUKmpS1)

About 3 μg of the pUK1 obtained in Reference Example 2 was dissolved in 30 μl of Y-100 buffer, 10 units each of the restriction enzyme PstI and BamHI were added, and the digestion reaction was conducted at 37° C. for 2 hours. After 10 minutes of heat treatment at 65° C., a 890-bp PstI-BamHI DNA fragment was purified using the AFT method [Bio/Technology, 2, 66–67 (1984)].

Separately, about 1 μg of the M13 phage vector M13mp18 RF DNA (Takara Shuzo) was dissolved in a total of 30 μl of Y-100 buffer, 10 units each of the restriction enzymes PstI and BamHI were added, and the digestion reaction was conducted at 37° C. for 2 hours. After 10 minutes of heat treatment at 65° C., a DNA fragment about 7.2 kb was purified using the AFT method.

The thus-obtained pUK1-derived DNA fragment (890 bp) and M13mp18RF-derived DNA fragment (about 7.2 kb) were dissolved in 20 μl of T4 ligase buffer, 300 units of T4 DNA ligase was added, and the ligation reaction was conducted at 4° C. for 18 hours.

The above reaction mixture was used to transfect Escherichia coli JM105 by a known method [Messing et al., Methods in Enzymology, 101, 20 (1983)] to give a recombinant phage. Then, Escherichia coli JM105 was infected with this recombinant phage by the Messing et al. method. A single-stranded phage DNA was recovered from the culture supernatant, while a double-stranded phage DNA was recovered from cultured cells in the same manner as in recovering plasmid DNAs. The structure of this double-stranded phage DNA (pUKmpS1) was confirmed by digestion with restriction enzymes (cf. FIG. 26).

(2) Mutagenesis in the UK cDNA using an oligonucleotide (a) Preparation of a synthetic DNA for mutagenesis and phosphorylation thereof For producing a UK derivative in which the 164th amino acid residue is Asn in lieu of Phe in UK and which has a carbohydrate chain added thereto (hereinafter this derivative is referred to as "UK-S1"), a 17-base synthetic DNA, 5'-GGGGAGAAAACAC-CACC-3', was synthesized using an Applied Biosystems model 380A DNA synthesizer.

Then, 25 picomoles of the thus-obtained synthetic DNA was phosphorylated at the 5' end by conducting the reaction in 10 μl of T4 kinase buffer in the presence of 5 units of T4 DNA kinase (Takara Shuzo) at 37° C. for 30 minutes.

(b) Site-directed mutagenesis using two oligonucleotide primers

A solution prepared by mixing 6.5 μl of a solution containing the single-stranded recombinant phage DNA (about 2 μg) obtained as described above, 1 μl of 10-fold concentrated polymerase buffer [containing 500 mM Tris-HCl (pH 7.8), 70 mM MgCl$_2$, 60 mM 2-mercaptoethanol, 0.25 mM dATP, 0.25 mM dCTP, 0.25 mM dGTP and 0.25 mM dTTP] and 2 μl of a solution containing the synthetic DNA (2.5 picomoles) for mutagenesis obtained as described above was allowed to stand at 65° C. for 5 minutes, at 55° C. for 5 minutes, at 37° C. for 10 minutes and then at 25° C. for 10 minutes. Then, 3 units of Escherichia coli DNA polymerase I Klenow fragment (Takara Shuzo) (hereinafter referred to as "Klenow fragment" for short) was added, and the reaction was conducted at 25° C. for 30 minutes. To the reaction mixture were then added 1 μl of 10-fold concentrated polymerase buffer, 6 μl of 0.5 picomole/μl M13 primer M4 (Takara Shuzo) and 3 units of Klenow fragment. After conducting the reaction at 37° C. for 10 minutes and then at 25° C. for 40 minutes, 2 μl of 10 mM ATP and 300 units of T4 DNA ligase were added, and the ligation reaction was conducted at 11° C. for 18 hours. The reaction mixture was subjected to phenol extraction and chloroform extraction, and a DNA fragment was recovered by precipitation with ethanol. This DNA fragment was dissolved in a total of 30 μl of Y-100 buffer, 12 units of EcoRI and 12 units of PstI were added, and the digestion reaction was conducted at 37° C. for 2 hours. After 10 minutes of heat treatment at 65° C., a PstI-EcoRI fragment (about 600 bp) was purified using the AFT method.

(c) Insertion of the mutant DNA fragment into a vector

About 3 μg of the pUK11 plasmid DNA obtained in Reference Example 3 was dissolved in 30 μl of Y-50 buffer, 10 units of AatII (Toyobo) and 8 units of PstI were added, and the digestion reaction was conducted at 37° C. for 2 hours. After 10 minutes of heat treatment at 65° C., an AatII-PstI fragment about 1.0 kb was purified using the AFT method. Separately, about 3 μg of the pUKB101 plasmid DNA obtained in Reference Example 8 was dissolved in 30 μl of Y-50 buffer, 10 units of AatII and 10 units of EcoRI were added, and the digestion reaction was conducted at 37° C. for 2 hours. After 10 minutes of heat treatment at 65° C., an AatII-EcoRI fragment about 2.9 kb was purified using the AFT method.

The thus-obtained pUK11-derived AatII-PstI fragment (about 0.05 μg) and pUKB101-derived AatII-EcoRI fragment (about 0.1 μg) were dissolved, together with the PstI-EcoRI fragment with mutation (about 600 bp), in 20 μl of T4 ligase buffer, 300 units of T4 DNA ligase was added, and the ligation reaction was conducted at 4° C. for 18 hours.

The reaction mixture thus obtained was used to transform Escherichia coli C600SF8 [Proc. Natl. Acad. Sci. U.S.A., 72, 3416 (1975)] to give Ap resistant transformants. A recombinant plasmid, pUKS1, capable hybridizing with a probe prepared by radiolabeling the above-mentioned synthetic DNA for mutagenesis with $^{32}$P at the 5' end was isolated from one of the transformants using the technique of colony hybridization. Structural analysis comprising digestion with restriction enzymes and DNA sequence determination by the dideoxy method using M13 phage confirmed that pUKS1 had the desired structure (cf. FIG. 27).

REFERENCE EXAMPLE 12

Construction of the t-PA expression plasmid pSE1PA1-9A (1) Construction of the recombinant plasmid pAGE105M An Escherichia coli HB101 transformant harboring the plasmid pAGE28 constructed by the present inventors [Mizukami et al., J. Biochem., 101, 1307–1310 (1987)] was cultured and the pAGE28 DNA was prepared from cultured cells by a conventional method. About 2 μg of the pAGE28 DNA obtained was dissolved in 30 μl of Y-100 buffer, 8 units of XhoI and 12 units of ScaI were added, and the digestion reaction was conducted at 37° C. for 2 hours. After 10 minutes of heat treatment at 65° C., a DNA fragment about 2.8 kb was purified using the AFT method. Separately, an *Escherichia coli* HB101 transformant harboring the plasmid pAGE103 constructed by the present inventors (Mizukami et al., J. Biochem., 101, 1307-1310 (1987)] was cultured and the pAGE103 DNA was prepared from cultured cells in a conventional manner. About 3 μg of the pAGE103 DNA obtained was dissolved in 30 μl of Y-100 buffer, 10 units of EcoRI was added, and the digestion reaction was conducted at 37° C. for 2 hours. After phenol extraction and chloroform extraction, a DNA fragment was recovered by precipitation with ethanol. This DNA fragment was dissolved in a total of 40 μl of polymerase buffer, 6 units of Klenow fragment were added, and the reaction was conducted at 15° C. for 1 hour to thereby convert the EcoRI protruding ends to blunt ends. The reaction was terminated by phenol extraction and, after chloroform extraction, a DNA fragment was recovered by precipitation with ethanol. This DNA fragment was dissolved in 30 μl of Y-100 buffer, 12 units of XhoI was added, and the digestion reaction was conducted at 37° C. for 2 hours. After 10 minutes of heat treatment at 65° C., a DNA fragment about 0.4 kb was purified using the AFT method. Separately, an *Escherichia coli* transformant harboring the plasmid pKCR constructed by O'Hara et al. [Proc. Natl. Acad. Sci. U.S.A., 78, 1527 (1981)] was cultured and the pKCR DNA was prepared from cultured cells by the conventional method. About 2 μg of the pKCR DNA obtained was dissolved in 30 μl of Y-150 buffer, 12 units of BamHI and 16 units of SalI were added, and the digestion reaction was conducted at 37° C. for 2 hours. After phenol extraction and chloroform extraction, a DNA fragment was recovered by precipitation with ethanol. This DNA fragment was dissolved in a total of 40 μl of polymerase buffer, 6 units of Klenow fragment were added, and the reaction was conducted at 15° C. for 1 hour for the conversion of the BamHI and SalI protruding ends to blunt ends. After 10 minutes of heat treatment at 65° C., a DNA fragment about 1.85 kb was purified using the AFT method.

The thus-obtained pAGE28-derived DNA fragment (about 2.8 kb, about 0.05 μg), pAGE103-derived DNA fragment (about 0.4 kb, about 0.03 μg) and pKCR-derived DNA fragment (about 1.85 kb, about 0.2 μg) were dissolved in 20 μl of T4 ligase buffer, 300 units of T4 DNA ligase was added, and the ligation reaction was conducted at 4° C. for 18 hours.

The thus-obtained reaction mixture was used to transform *Escherichia coli* MM294 to give kanamycin (hereinafter referred to as "Km")-resistant transformants. The plasmid pAGE105M isolated from one of these transformants was found to have the desired structure upon structural analysis comprising digestion with restriction enzymes (cf. FIG. 28).

(2) Construction of the recombinant plasmid pAGE106

About 2 μg of the pAGE105M DNA obtained as described above was dissolved in 30 μl of Y-100 buffer, 12 units of ScaI was added, and the digestion reaction was conducted at 37° C. for 2 hours. After 10 minutes of heat treatment at 65° C., a DNA fragment about 5.0 kb was purified using the AFT method. Separately, 20 picomoles of the EcoRI linker GGAATTCC (Collaborative Research) was 5'-phosphorylated in the same manner as mentioned hereinbefore.

The thus-obtained pAGE105M-derived DNA fragment (about 5.0 kb, about 0.1 μg), 5'-phosphorylated EcoRI linker (1 picomole) were dissolved in 20 μl T4 ligase buffer, 100 units of T4 DNA ligase was added, and the ligation reaction was conducted at 4° C. for 18 hours.

The thus-obtained reaction mixture was used to transform *Escherichia coli* MM294 to give Km-resistant transformants. The plasmid DNA pAGE106 isolated from one of these transformants was found to have the desired structure upon structural analysis comprising digestion with restriction enzymes (cf. FIG. 29).

(3) Construction of the t-PA expression plasmid pSE1-PA1-5

About 2 μg of the pAGE106 DNA obtained as described above was dissolved in 30 μl of Y-0 buffer, 12 units of KpnI was added, and the digestion reaction was conducted at 37° C. for 2 hours. Then, 1.5 μl of 2M NaCl and 10 units of BamHI were added, and the digestion reaction was further conducted at 37° C. for 2 hours. After 10 minutes of heat treatment at 65° C., a DNA fragment about 5.0 kb was purified using the AFT method. Separately, about 3 μg of the ptPA7 plasmid DNA obtained in Reference Example 1 was dissolved in 30 μl of Y-0 buffer containing 75 mM NaCl, 12 units of FokI and 12 units of EcoRI were added, and the digestion reaction was conducted at 37° C. for 2 hours. After 10 minutes of heat treatment at 65° C., a DNA fragment about 0.7 kb was purified using the AFT method. Further, separately, about 3 μg of the pTA4 DNA was dissolved in 30 μl of Y-0 buffer, 12 units of KpnI was added, and the digestion reaction was conducted at 37° C. for 2 hours. Then, 1.5 μl of 2M NaCl and 1 unit of EcoRI were added, and the digestion reaction was further conducted at 37° C. for 1 hour. Under the above conditions, the digestion of the DNA with KpnI was complete and that with EcoRI was partial. After 10 minutes of heat treatment at 65° C., and EcoRI-KpnI fragment about 1.4 kb was purified using the AFT method. Furthermore, the following two synthetic DNAs (each having 21 bases) were synthesized using an Applied Biosystems model 380A DNA synthesizer and individually 5'-phosphorylated by the same method as mentioned before.

```
5'-GATCCATGGATGCAATGAAGA-3'
3'-GTACCTACGTTACTTCTCTCC-5'
```

The thus-obtained pAGE106-derived DNA fragment (about 5.0 kb, about 0.1 μg), ptPA7-derived DNA fragment (about 0.7 kb, about 0.1 μg), pTA4-derived EcoRI-KpnI fragment (about 1.4 kb, about 0.05 μg) and two 5'-phosphorylated synthetic DNAs (1 picomole each) were dissolved in 20 μl of T4 ligase buffer, 50 units of T4 DNA ligase was added, and the ligation reaction was conducted at 4° C. for 18 hours.

The thus-obtained reaction mixture was used to transform *Escherichia coli* MM294 to give Km-resistant transformants. The plasmid DNA pSE1PA1-5 isolated from one of these transformants was found to have the desired structure upon structural analysis comprising digestion with restriction enzymes and DNA sequence determination by the dideoxy method using M13 phage (cf. FIG. 30).

(4) Construction of the t-PA expression plasmid pSE1-PA1-9

About 2 μg of the pSE1PA1-5 DNA obtained as described above was dissolved in 30 μl of Y-0 buffer, 12 units of KpnI was added, and the digestion reaction was conducted at 37° C. for 2 hours. Then, 1.5 μl of 2M NaCl and 8 units of HindIII were added, and the digestion reaction was further conducted at 37° C. for 2 hours. After 10 minutes of heat treatment at 65° C., a DNA fragment about 5.0 kb was purified using the AFT method. Separately, about 2 μg of the pSE1PA1-5 DNA was dissolved in 30 μl of Y-0 buffer, 12 units of KpnI was added, and the digestion reaction was conducted at 37° C. for 2 hours. Then, 1.0 μl of 2M NaCl and 10 units of NcoI were added, and the digestion reaction was further conducted at 37° C. for 2 hours. After 10 minutes of heat treatment at 65° C., a DNA fragment about 4.9 kb was purified using the AFT method. Furthermore, the following four synthetic DNAs (47 bases, 49 bases, 49 bases and 47 bases; these synthetic DNAs constituting a part of the 5'-nontranslational region of the t-PA cDNA)) were synthesized using an Applied Biosystems model 380A DNA synthesizer and individually 5'-phosphorylated in the same manner as mentioned above.

The thus-obtained pUC19-derived DNA fragments (about 1.55 kb and about 1.1 kb), and 5'-phosphorylated HindIII linker (2 picomoles) were dissolved in 20 μl of T4 ligase buffer, 50 units of T4 DNA ligase was added, and the ligation reaction was conducted at 4° C. for 18 hours.

The reaction mixture thus obtained was used to transform Escherichia coli MM294 to give Ap-resistant transformants. The plasmid DNA pUC19H isolated from one of these transformants was found to have the desired structure upon structural analysis comprising digestion with restriction enzymes (cf. FIG. 32).

(6) Construction of the recombinant plasmid pSE1PA1-9A (Insertion of Ap-resistance gene into pSE1PA1-9)

About 2 μg of the pUC19H plasmid DNA obtained as described above was dissolved in 30 μl of Y-50 buffer, 8 units of HindIII was added, and the digestion reaction was conducted at 37° C. for 2 hours. After phenol extraction and chloroform extraction, a DNA fragment was recovered by precipitation with ethanol. This DNA fragment was dissolved in a total of 40 μl of polymerase buffer, 6 units of Klenow fragment were added, and the reaction was conducted at 15° C. for 1

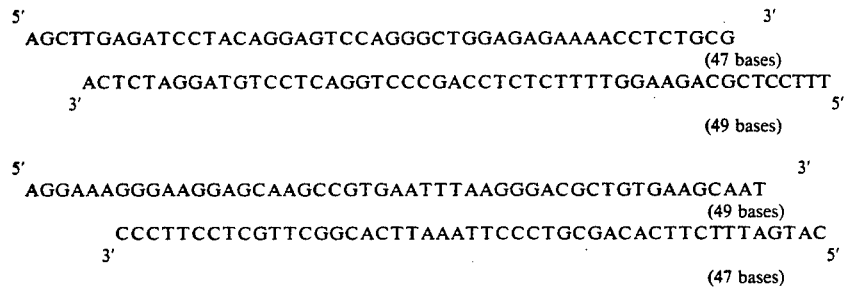

The thus-obtained pSE1PA1-5-derived 5.0 kb DNA fragment (about 0.1 μg), pSE1PA1-5-derived 4.9 kb DNA fragment (about 0.1 μg), and four 5'-phosphorylated synthetic DNAs (1 picomole each) were dissolved in 20 μl of T4 ligase buffer, 50 units of T4 DNA ligase was added, and the ligation reaction was conducted at 4° C. for 18 hours.

The thus-obtained reaction mixture was used to transform Escherichia coli MM294 to give Km-resistant transformants. The plasmid DNA pSE1PA1-9 isolated from one of these transformants was found to have the desired structure upon structural analysis comprising digestion with restriction enzymes and DNA sequence determination by the dideoxy method using M13 phage (cf. FIG. 31).

(5) Construction of the recombinant plasmid pUC19H (for rendering the Ap resistance gene portable)

About 2 μg of the plasmid DNA pUC19 constructed by Norrander et al. [Norrander, J. et al., Gene, 26, 101 (1983); available from Takara Shuzo] was dissolved in 30 μl of Y-50 buffer, 10 units of HindIII and 1 unit of DraI were added, and the digestion reaction was conducted at 37° C. for 1 hour. Under these conditions, the digestion of the DNA with HindIII was complete while that with DraI was partial. After 10 minutes of heat treatment at 65° C., two DNA fragments, namely a HindIII-DraI fragment about 1.55 kb and a DraI-HindIII fragment about 1.1 kb, were purified using the AFT method. Separately, 20 picomoles of the HindIII linker CAAGCTTG (Collaborative Research) was 5'-phosphorylated by the same method as mentioned hereinabove.

hour for converting the HindIII protruding ends to blunt ends. The reaction was terminated by phenol extraction and, after chloroform extraction, a DNA fragment was recovered by precipitation with ethanol. This DNA fragment was dissolved in 30 μl of Y-50 buffer, 8 units of PvuII was added, and the digestion reaction was conducted at 37° C. for 2 hours. After 10 minutes of heat treatment at 65° C., a DNA fragment about 1.4 kb was purified using the AFT method. Separately, about 2 μg of the t-PA expression plasmid pSE1-PA1-9 obtained as described above was dissolved in 30 μl of Y-150 buffer, 8 units of XhoI and 8 units of EcoRV were added, and the digestion reaction was conducted at 37° C. for 2 hours. After 10 minutes of heat treatment at 65° C., a DNA fragment about 5.9 kb was purified using the AFT method. Furthermore, about 3 μg of the pAGE28 plasmid DNA prepared as described hereinbefore was dissolved in 30 μl of Y-150 buffer, 10 units of XhoI and 10 units of EcoRV were added, and the digestion reaction was conducted at 37° C. for 2 hours. After 10 minutes of heat treatment at 65° C., a DNA fragment about 0.85 kb was purified using the AFT method.

The thus-obtained pUC19H-derived DNA fragment (about 1.4 kb, about 0.1 μg), pSE1PA1-9-derived DNA fragment (about 5.9 kb, about 0.1 μg) and pAGE28-derived DNA fragment (about 0.85 kb, about 0.05 μg) were dissolved in 20 μl of T4 ligase buffer, 100 units of T4 DNA ligase was added, and the ligation reaction was conducted at 4° C. for 18 hours.

The reaction mixture thus obtained was used to transform Escherichia coli MM294 to give transformants resistant to both Ap and Km. The plasmid DNA pSE1-

PA1-9A isolated from one of these transformants was found to have the desired structure upon structural analysis comprising digestion with restriction enzymes (cf. FIG. 33).

AFT method. Separately, the following six synthetic DNAs (39 bases, 41 bases, 41 bases, 39 bases, 17 bases and 17 bases) were synthesized and respectively 5'-phosphorylated following the procedure mentioned above.

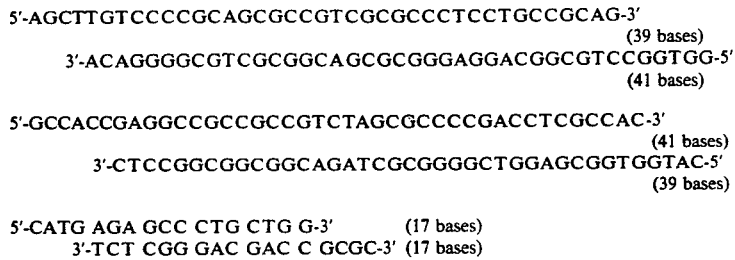

5'-CATG AGA GCC CTG CTG G-3'     (17 bases)
3'-TCT CGG GAC GAC C GCGC-3'     (17 bases)

REFERENCE EXAMPLE 13

Construction of the human pro-UK expression plasmid pSEUK1-1A (1) Construction of the recombinant plasmid pUKF2

About 3 μg of the pUK11 plasmid DNA obtained in Reference Example 3 was dissolved in 30 μl of Y-100 buffer, 12 units of NcoI and 12 units of HindIII were added, and the digestion reaction was conducted at 37° C. for 2 hours. After 10 minutes of heat treatment at 65° C., a DNA fragment about 0.45 kb was purified using the AFT method. Separately, about 2 μg of the pUKA2 plasmid DNA obtained in Reference Example 8-(1) was dissolved in 30 μl of Y-0 buffer, 10 units of KpnI was added, and the digestion reaction was conducted at 37° C. for 2 hours. Then, 1.5 μl of 2M NaCl and 10 units of NcoI were added, and the digestion reaction was further conducted at 37° C. for 2 hours. After 10 minutes of heat treatment at 65° C., a DNA fragment about 1.2 kb was purified using the AFT method. Furthermore, about 2 μg of the pTerm2 plasmid DNA obtained in Reference Example 5 was dissolved in 30 μl of Y-0 buffer, 10 units of KpnI was added, and the digestion reaction was conducted at 37° C. for 2 hours. Then, 1.5 μl of 2M NaCl and 8 units of HindIII were added, and the digestion reaction was further conducted at 37° C. for 2 hours. After 10 minutes of heat treatment at 65° C., a DNA fragment about 2.85 kb was purified using the AFT method.

The thus-obtained pUK11-derived DNA fragment (about 0.45 kb, about 0.02 μg), pUKA2-derived DNA fragment (about 1.2 kb, about 0.05 μg) and pTerm2-derived DNA fragment (about 2.85 kb, about 0.05 μg) were dissolved in 20 μl of T4 ligase buffer, 50 units of T4 DNA ligase was added, and the ligation reaction was conducted at 4° C. for 18 hours.

The reaction mixture thus obtained was used to transform Escherichia coli MM294 to give Ap-resistant transformants. The plasmid DNA pUKF2 isolated from one of these transformants was found to have the desired structure upon structural analysis comprising digestion with restriction enzymes (cf. FIG. 34).

(2) Construction of the recombinant plasmid pUKFpro

About 2 μg of the pUKF2 plasmid DNA obtained as described above was dissolved in 30 μl of Y-0 buffer containing 25 mM NaCl, 10 units of BssHII (New England Biolabs) was added, and the digestion reaction was conducted at 50° C. for 2 hours. Then, 1.0 μl of 2M NaCl and 10 units of HindIII were added, and the digestion reaction was further conducted at 37° C. for 2 hours. After 10 minutes of heat treatment at 65° C., a DNA fragment about 4.3 kb was purified using the AFT method.

The thus-obtained pUKF2-derived DNA fragment (about 4.3 kb, about 0.1 μg) and six 5'-phosphorylated synthetic DNAs (1 picomole each) were dissolved in 20 μl of T4 ligase buffer, 300 units of T4 DNA ligase was added, and the ligation reaction was conducted at 4° C. for 18 hours.

The reaction mixture thus obtained was used to transform Escherichia coli MM294 to give Ap-resistant transformants. The plasmid DNA pUKFpro isolated from one of these transformants was found to have the desired structure upon structural analysis comprising digestion with restriction enzymes and DNA sequence determination by the M13 dideoxy method (cf. FIG. 35).

(3) Construction of the recombinant plasmid pSEUK1-1A

About 2 μg of the pSE1PA1-9A plasmid DNA obtained in Reference Example 12 was dissolved in 30 μl of Y-0 buffer, 10. units of KpnI was added, and the digestion reaction was conducted at 37° C. for 2 hours. Then, 1.5 μl of 2M NaCl and 10 units of HindIII were added, and the digestion reaction was further conducted at 37° C. for 2 hours. After 10 minutes of heat treatment at 65° C., a DNA fragment about 6.3 kb was purified using the AFT method. Separately, about 3 μg of the pUKFpro plasmid DNA obtained as described above was dissolved in 30 μl of Y-0 buffer, 15 units of KpnI was added, and the digestion reaction was conducted at 37° C. for 2 hours. Then, 1.5 μl of 2M NaCl and 10 units of HindIII were added, and the digestion reaction was further conducted at 37° C. for 2 hours. After 10 minutes of heat treatment at 65° C., a DNA fragment about 1.55 kb was purified using the AFT method.

The thus-obtained pSE1PA1-9A-derived DNA fragment (about 6.3 kb, about 0.1 μg) and pUKFpro-derived DNA fragment (about 1.55 kb, about 0.05 μg) were dissolved in 20 μl of T4 ligase buffer, 100 units of T4 DNA ligase was added, and the ligation reaction was conducted at 4° C. for 18 hours.

The reaction mixture thus obtained was used to transform Escherichia coli MM294 to give Ap-resistant transformants. The plasmid DNA pSEUK1-1A isolated from one of these transformants was found to have the desired structure upon structural analysis comprising digestion with restriction enzymes (cf. FIG. 36).

REFERENCE EXAMPLE 14

Construction of the t-PA expression plasmid pSPAS1-9A (1) Construction of the recombinant plasmid pSE1dhfr1A About 2 μg of the pAGE106 plasmid DNA obtained in Reference Example 12-(2) was dissolved in 30 μl of Y-50 buffer, 12 units of Asp718 (Boehringer-Mannheim) was added, and the digestion reaction was conducted at 37° C. for 2 hours. After phenol extraction and chloroform extraction, a DNA fragment was recovered by precipitation with ethanol. This DNA fragment was dissolved in a total of 40 μl of polymerase buffer, 6 units of Klenow fragment was added, and the reaction was conducted at 15° C. for 1 hour to thereby convert the Asp718 protruding ends to blunt ends. Then, after phenol extraction and chloroform extraction, a DNA fragment was recovered by precipitation with ethanol and dissolved in a total of 30 μl of Y-150 buffer, 10 units of MluI was added, and the digestion reaction was conducted at 37° C. for 2 hours. After 10 minutes of heat treatment at 65° C., a DNA fragment about 3.3 kb was purified using the AFT method.

Separately, about 3 μg of the dhfr gene-containing pSV2dhfr plasmid DNA [Subramani et al., Mol. Cell. Biol. 1, 854 (1981)] was dissolved in 30 μl of Y-100 buffer, 12 units of BglII was added, and the digestion reaction was conducted at 37° C. for 2 hours. After phenol extraction and chloroform extraction, a DNA fragment was recovered by precipitation with ethanol. This DNA fragment was dissolved in a total of 40 μl of polymerase buffer, 6 units of Klenow fragment were added, and the reaction was conducted at 15° C. for 1 hour to thereby convert the BglII protruding ends to blunt ends. Then, after phenol extraction and chloroform extraction, a DNA fragment was recovered by precipitation with ethanol and dissolved in a total of 30 μl of Y-100 buffer, 12 units of HindIII was added, and the digestion reaction was conducted at 37° C. for 2 hours. After 10 minutes of heat treatment at 65° C., a DNA fragment about 0.75 kb was purified using the AFT method. Furthermore, about 3 μg of the pSE1-PA1-9A plasmid DNA obtained in reference Example 12 was dissolved in 30 μl of Y-100 buffer, 12 units of HindIII was added, and the digestion reaction was conducted at 37° C. for 2 hours. Then, 1.5 μl of 1M NaCl and 12 units of MluI were added, and the digestion reaction was further conducted at 37° C. for 2 hours. After 10 minutes of heat treatment at 65° C., a DNA fragment about 2.9 kb was purified using the AFT method.

The thus-obtained pAGE106-derived DNA fragment (about 0.1 μg), pSV2dhfr-derived DNA fragment (about 0.03 μg) and pSE1PA1-9A-derived DNA fragment (about 0.1 μg) were dissolved in 20 μl of T4 ligase buffer, 100 units of T4 DNA ligase was added, and the ligation reaction was conducted at 4° C. for 18 hours.

The reaction mixture thus obtained was used to transform Escherichia coli MM294 to give Ap-resistant transformants. The plasmid DNA pSE1dhfr1A isolated from one of these transformants was found to have the desired structure upon structural analysis comprising digestion with restriction enzymes (cf. FIG. 37).

(2) Construction of the recombinant plasmid pSPAS1-9A

About 3 μg of the pSE1dhfr1A plasmid DNA obtained as described above was dissolved in 30 μl of Y-100 buffer, 12 units of XhoI was added, and the digestion reaction was conducted at 37° C. for 2 hours. After phenol extraction and chloroform extraction, a DNA fragment was recovered by precipitation with ethanol. This DNA fragment was dissolved in 40 μl of polymerase buffer, 6 units of Klenow fragment was added, and the reaction was conducted at 15° C. for 1 hour to thereby convert the XhoI protruding ends to blunt ends. Then, after phenol extraction and chloroform extraction, a DNA fragment was recovered by precipitation with ethanol and dissolved in 30 μl of Y-150 buffer, 12 units of MluI was added, and the digestion reaction was conducted at 37° C. for 2 hours. After 10 minutes of heat treatment at 65° C., a DNA fragment about 4.4 kb was purified using the AFT method.

Separately, about 3 μg of the pSE1PA1-9A plasmid DNA obtained in reference Example 12 was dissolved in 30 μl of Y-50 buffer, 12 units of ClaI was added, and the digestion reaction was conducted at 37° C. for 2 hours. After phenol extraction and chloroform extraction, a DNA fragment was recovered by precipitation with ethanol. This DNA fragment was dissolved in 40 μl of polymerase buffer, 6 units of Klenow fragment was added, and the reaction was conducted at 15° C. for 1 hour to thereby convert the ClaI protruding ends to blunt ends. Then, after phenol extraction and chloroform extraction, a DNA fragment was recovered by precipitation with ethanol and dissolved in 30 μl of Y-150 buffer, 12 units of MluI was added, and the digestion reaction was conducted at 37° C. for 2 hours. After 10 minutes of heat treatment at 65° C., a DNA fragment about 6.75 kb was purified using the AFT method.

The thus-obtained pSE1dhfr1A-derived DNA fragment (about 0.1 μg) and pSE1PA1-9A-derived DNA fragment (about 0.1 μg) were dissolved in 20 μl of T4 ligase buffer, 100 units of T4 DNA ligase was added, and the ligation reaction was conducted at 4° C. for 18 hours.

The reaction mixture thus obtained was used to transform Escherichia coli MM294 to give Ap-resistant transformants. The plasmid DNA pSPAS1-9A isolated from one of these transformants was found to have the desired structure upon structural analysis comprising digestion with restriction enzymes (cf. FIG. 37).

REFERENCE EXAMPLE 15

Construction of the recombinant plasmid pUKT1 coding for the pro-UK derivative UK-T About 2 μg of the pUK11 plasmid DNA obtained in Reference Example 3-(3) was dissolved in 30 μl of Y-100 buffer, 16 units of EcoO109 and 10 units of HindIII were added, and the digestion reaction was conducted at 37° C. for 2 hours. After 10 minutes of heat treatment at 65° C., a DNA fragment about 0.75 kb was purified using the AFT method. Separately, about 2 μg of the phPA2 plasmid DNA obtained in Reference Example 10 was dissolved in 30 μl of Y-100 buffer, 10 units each of HindIII and EcoRI were added, and the digestion reaction was conducted at 37° C. for 2 hours. After 10 minutes of heat treatment at 65° C., a DNA fragment about 3.4 kb was purified using the AFT method. Furthermore, the following two synthetic DNAs (each having 43 bases) were synthesized and 5'-phosphorylated following the procedure already mentioned hereinbefore.

5'-GCCCCGGGAGAAGATTATTGGCGGAG-3'
3'-GGCCCTCTTCTAATAACCGCCTCTTAA-5'

The thus-obtained pUK11-derived DNA fragment (about 0.75 kb, about 0.1 μg), phPA2-derived DNA fragment (about 3.4 kb, about 0.1 μg) and two 5'-phosphorylated synthetic DNAs (1 picomole each) were dissolved in 20 μl of T4 ligase buffer, 300 units of T4 DNA ligase was added, and the ligation reaction was conducted at 4° C. for 18 hours.

The reaction mixture thus obtained was used to transform *Escherichia coli* MM294 to give Ap-resistant transformants. Plasmid DNAs were isolated from these transformants and subjected to structural analysis comprising digestion with restriction enzymes and to DNA sequence determination by the M13 dideoxy sequence method. As a result, it was confirmed that pUKT1 had the desired structure (cf. FIG. 38).

REFERENCE EXAMPLE 16

Construction of the UK-T expression plasmid DNA pSEUKT

About 2 μg of the pSPAS1-9A plasmid DNA obtained in Reference Example 14 was dissolved in 30 μl of Y-0 buffer, 10 units of KpnI was added, and the digestion reaction was conducted at 37° C. for 2 hours. Then, 1.5 μl of 2M NaCl and 10 units of XhoI were added, and the digestion reaction was further conducted at 37° C. for 1 hour. After 10 minutes of heat treatment at 65° C., a DNA fragment about 8.6 kb was purified using the AFT method. Separately, about 3 μg of the pSEUK1-1A plasmid DNA was dissolved in 30 μl of Y-100 buffer, 12 units of BglII and 12 units of XhoI were added, and the digestion reaction was conducted at 37° C. for 2 hours. After 10 minutes of heat treatment at 65° C., a DNA fragment about 0.75 kb was purified using the AFT method. Further, separately, about 3 μg of the pUKT1 plasmid DNA obtained as described above was dissolved in 30 μl of Y-0 buffer, 15 units of KpnI was added, and the digestion reaction was conducted at 37° C. for 2 hours. Then, 1.5 μl of 2M NaCl and 12 units of BglII were added, and the digestion reaction was further conducted at 37° C. for 1 hour. After 10 minutes of heat treatment at 65° C., a DNA fragment about 1.15 kb was purified using the AFT method.

The thus-obtained pSPAS1-9A-derived DNA fragment (about 8.6 kb, about 0.1 μg), pSEUK1-1A-derived DNA fragment (about 0.75 kb, about 0.02 μg) and pUKS1-derived DNA fragment (about 1.15 kb, about 0.02 μg) were dissolved in 20 μl of T4 ligase buffer, 100 units of T4 DNA ligase was added, and the ligation reaction was conducted at 4° C. for 18 hours.

The reaction mixture thus obtained was used to transform *Escherichia coli* MM294 to give Ap-resistant transformants. The plasmid DNA pSEUKT isolated from one of these transformants was found to have the desired structure upon structural analysis comprising digestion with restriction enzymes (cf. FIG. 39).

As detailedly described hereinabove, the present invention makes it possible to supply polypeptides usable as thrombolytic agents on a industrial scale utilizing the recombinant DNA technology and the use of these polypeptides for therapeutic benefit.

While the invention has been described in detail and with reference to specific embodiments thereof, it will be apparent to one skilled in the art that various changes and modifications can be made therein without departing from the spirit and scope thereof.

What is claimed is:

1. A plasminogen activator which is identical in peptide sequence to naturally occurring human prourokinase except that the 155th amino acid from serine, the N-terminal amino acid, is threonine and the 153rd amino acid is selected from leucine, serine and asparagine.

2. The plasminogen activator of claim 11, wherein the 153rd amino acid is asparagine.

3. The plasminogen activator of claim 1, wherein the 153rd amino acid is serine.

4. The plasminogen activator of claim 1 which has the peptide sequence shown in FIG. 40, FIG. 41, or FIG. 42.

5. A method of treating cerebral thrombosis or myocardial infarction comprising administering to a person requiring same an effective amount of the plasminogen activator of claim 1.

6. A pharmaceutical composition for the prevention or treatment of cerebral thrombosis or myocardial infarction comprising an effective amount of the plasminogen activator of claim 1 together with a pharmaceutically acceptable carrier or diluent.

* * * * *